(12) United States Patent
Xue et al.

(10) Patent No.: US 8,697,870 B2
(45) Date of Patent: *Apr. 15, 2014

(54) 3-CYCLOALKYLAMINOPYRROLIDINE DERIVATIVES AS MODULATORS OF CHEMOKINE RECEPTORS

(75) Inventors: Chu-Biao Xue, Hockessin, DE (US); Brian W. Metcalf, Moraga, CA (US); Amy Qi Han, Hockessin, DE (US); Darius J. Robinson, Wilmington, DE (US); Changsheng Zheng, Wilmington, DE (US); Anlai Wang, Wilmington, DE (US); Yingxin Zhang, New Castle, DE (US)

(73) Assignee: Incyte Corporation, Wilmington, DE (US)

( * ) Notice: Subject to any disclaimer, the term of this patent is extended or adjusted under 35 U.S.C. 154(b) by 850 days.

This patent is subject to a terminal disclaimer.

(21) Appl. No.: 12/274,045

(22) Filed: Nov. 19, 2008

(65) Prior Publication Data

US 2009/0286792 A1 Nov. 19, 2009

Related U.S. Application Data

(63) Continuation of application No. 11/014,322, filed on Dec. 16, 2004, now Pat. No. 7,576,089.

(60) Provisional application No. 60/531,270, filed on Dec. 18, 2003.

(51) Int. Cl.
*A61K 31/506* (2006.01)
*C07D 403/14* (2006.01)
*C07D 401/14* (2006.01)

(52) U.S. Cl.
USPC ........... 544/333; 514/256; 514/326; 514/422; 548/518

(58) Field of Classification Search
USPC ........... 544/333; 514/326, 256, 422; 548/518
See application file for complete search history.

(56) References Cited

U.S. PATENT DOCUMENTS 5,171,355 A * 12/1992 Negele et al. ................. 504/287

OTHER PUBLICATIONS

Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed.", Marcel Dekker, New York, 1996, pp. 451 and 596.*
Zhang et. al. "Overcoming hERG activity in the discovery of a series of 4-azetidinyl-1-aryl-cyclohexanes as CCR2 antagonists" Bioorg. Med. Chem. Lett. (2011), doi:10.1016/j.bmcl.2011.06.080 pp. 1-6.*
Michael Schnürch, "Cross-Coupling Reactions on Azoles with Two and More Heteroatoms" European Journal of Organic Chemistry 2006, 15, 3283-3307.*

* cited by examiner

*Primary Examiner* — David K O Dell
(74) *Attorney, Agent, or Firm* — Novak Druce Connolly Bove + Quigg LLP

(57) ABSTRACT

The present invention relates to 3-cycloalkylaminopyrrolidine derivatives of the formula I:

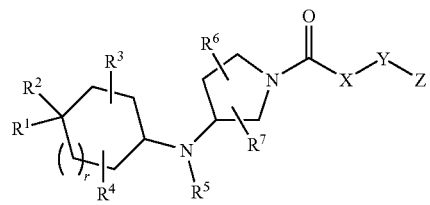

(wherein $R^1$, $R^2$, $R^3$, $R^4$, $R^5$, $R^6$, $R^7$, X, Y and Z are as defined herein) which are useful as modulators of chemokine receptor activity. In particular, these compounds are useful as modulators of chemokine receptors and more specifically as modulators of the CCR2 and/or CCR5 receptor. The compounds and compositions of the invention may bind to chemokine receptors, e.g., the CCR2 and/or CCR5 chemokine receptors, and are useful for treating diseases associated with chemokine, e.g., CCR2 and/or CCR5, activity, such as atherosclerosis, restenosis, lupus, organ transplant rejection and rheumatoid arthritis.

2 Claims, No Drawings

3-CYCLOALKYLAMINOPYRROLIDINE DERIVATIVES AS MODULATORS OF CHEMOKINE RECEPTORS

CROSS-REFERENCE TO RELATED APPLICATIONS

This application claims the benefit of U.S. Provisional Application Ser. No. 60/531,270, filed Dec. 18, 2003, the disclosure of which is incorporated herein by reference in its entirety.

FIELD OF THE INVENTION

The instant invention is directed to chemokine receptor modulators, e.g., antagonists, and their use as medicinal agents. The present invention further relates to novel compounds and medical methods of treatment of inflammation, and other disorders especially those associated with lymphocyte or monocyte accumulation such as rheumatoid arthritis, lupus, graft versus host diseases and/or transplant rejection. More particularly, the present invention relates to 3-cycloalkylaminopyrrolidine derivatives and their use as modulators of chemokine receptors.

More specifically, the instant invention relates to new anti-inflammatory and immunomodulatory bioactive compounds and pharmaceutical compositions thereof that act via antagonism of the CCR2 receptor, (also known as the MCP-1 receptor), and therefore leading to the inhibition of Monocyte Chemoattractant Protein-1 (MCP-1). The new compounds are 3-cycloalkylaminopyrrolidine derivatives. The invention further relates to novel compounds for use in the compositions, to processes for their preparation, to intermediates useful in their preparation and to their use as therapeutic agents.

The chemokine receptor modulators/antagonists of the invention may be effective as therapeutic agents and/or preventive agents for diseases such as atherosclerosis, asthma, pulmonary fibrosis, myocarditis, ulcerative colitis, psoriasis, asthma, ulcerative colitis, nephritis (nephropathy), multiple sclerosis, lupus, systemic lupus erythematosus, hepatitis, pancreatitis, sarcoidosis, organ transplantation, Crohn's disease, endometriosis, congestive heart failure, viral meningitis, cerebral infarction, neuropathy, Kawasaki disease, and sepsis in which tissue infiltration of blood leukocytes, such as monocytes and lymphocytes, play a major role in the initiation, progression or maintenance of the disease.

The present invention also provides immunomodulatory bioactive compounds and pharmaceutical compositions thereof that act via antagonism of the CCR5 receptor.

BACKGROUND OF THE INVENTION

The migration and transport of leukocytes from blood vessels into diseased tissues appears to be a critical component to the initiation of normal disease-fighting inflammatory responses. The process, also known as leukocyte recruitment, is also related to the onset and progression of life-threatening inflammatory, as well as debilitating autoimmune diseases. The resulting pathology of these diseases derives from the attack of the body's immune system defenses on normal tissues. Accordingly, preventing and blocking leukocyte recruitment to target tissues in inflammatory and autoimmune disease would be a highly effective approach to therapeutic intervention.

The different classes of leukocyte cells that are involved in cellular immune responses include monocytes, lymphocytes, neutrophils, eosinophils and basophils. In most cases, lymphocytes are the leukocyte class that initiates, coordinates, and maintains chronic inflammatory responses, and thus are generally the most important class of cells to block from entering inflammatory sites. Lymphocytes attract monocytes to the tissue sites, which, collectively with lymphocytes, are responsible for most of the actual tissue damage that occurs in inflammatory disease. Infiltration of the lymphocytes and/or monocytes is known to lead to a wide range of chronic, autoimmune diseases, and also organ transplant rejection. These diseases include, but are not limited to, rheumatoid arthritis, chronic contact dermatitis, inflammatory bowel disease, lupus, systemic lupus erythematosus, multiple sclerosis, atherosclerosis, psoriasis, sarcoidosis, idiopathic pulmonary fibrosis, dermatomyositis, skin pemphigoid and related diseases, (e.g., *pemphigus vulgaris, p. foliacious, p. erythematosis*), glomerulonephritides, vasculitides, hepatitis, diabetes, allograft rejection, and graft-versus-host disease.

The process, by which leukocytes leave the bloodstream and accumulate at inflammatory sites, and start a disease, has at least three steps which have been described as (1) rolling, (2) activation/firm adhesion and (3) transendothelial migration [Springer, T. A., Nature 346:425-433 (1990); Lawrence and Springer, Cell 65:859-873 (1991); Butcher, E. C., Cell 67:1033-1036 (1991)]. The second step is mediated at the molecular level by chemoattractant receptors. Chemoattractant receptors on the surface of leukocytes then bind chemoattractant cytokines which are secreted by cells at the site of damage or infection. Receptor binding activates leukocytes, increases the adhesiveness of the adhesion molecules that mediate transendothelial migration, and promotes directed migration of the cells toward the source of the chemoattractant cytokine.

Chemotactic cytokines (leukocyte chemoattractant/activating factors) also known as chemokines, also known as intercrines and SIS cytokines are a group of inflammatory/immunomodulatory polypeptide factors, of molecular weight 6-15 kDa, that are released by a wide variety of cells such as macrophages, monocytes, eosinophils, neutrophiles, fibroblasts, vascular endothelial cells, smooth muscle cells, and mast cells, at inflammatory sites (reviewed in Luster, New Eng. J. Med., 338, 436-445 (1998) and Rollins, Blood, 90, 909-928 (1997)). Also, chemokines has been described in Oppenheim, J. J. et al., Annu. Rev. Immunol., 9:617-648 (1991); Schall and Bacon, Curr. Opin. Immunol., 6:865-873 (1994); Baggiolini, M., et al., and Adv. Immunol., 55:97-179 (1994). Chemokines have the ability to stimulate directed cell migration, a process known as chemotaxis. Each chemokine contains four cysteine residues (C) and two internal disulfide bonds. Chemokines can be grouped into two subfamilies, based on whether the two amino terminal cysteine residues are immediately adjacent (CC family) or separated by one amino acid (CXC family). These differences correlate with the organization of the two subfamilies into separate gene clusters. Within each gene cluster, the chemokines typically show sequence similarities between 25 to 60%. The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

MCP-1 (also known as MCAF (abbreviation for macrophage chemotactic and activating factor) or JE) is a CC chemokine produced by monocytes/macrophages, smooth muscle cells, fibroblasts, and vascular endothelial cells and causes cell migration and cell adhesion of monocytes (see for example Valente, A. J., et al., Biochemistry, 1988, 27, 4162; Matsushima, K., et al., J. Exp. Med., 1989, 169, 1485; Yoshimura, T., et al., J. Immunol., 1989, 142, 1956; Rollins, B. J., et al., Proc. Natl. Acad. Sci. USA, 1988, 85, 3738; Rollins, B. J., et al., Blood, 1991, 78, 1112; Jiang, Y., et al., J. Immunol., 1992, 148, 2423; Vaddi, K., et al., J. Immunol., 1994, 153, 4721), memory T lymphocytes (see for example Carr, M. W., et al., Proc. Natl. Acad. Sci. USA, 1994, 91, 3652), T lymphocytes (see for example Loetscher, P., et al., FASEB J., 1994, 8, 1055) and natural killer cells (see for example Loetscher, P., et al., J. Immunol., 1996, 156, 322; Allavena, P., et al., Eur. J. Immunol., 1994, 24, 3233), as well as mediating histamine release by basophils (see for example Alam, R., et al., J. Clin. Invest., 1992, 89, 723; Bischoff, S. C., et al., J. Exp. Med., 1992, 175, 1271; Kuna, P., et al., J. Exp. Med., 1992, 175, 489). In addition, high expression of MCP-1 has been reported in diseases where accumulation of monocyte/macrophage and/or T cells is thought to be important in the initiation or progression of diseases, such as atherosclerosis (see for example Hayes, I. M., et al., Arterioscler. Thromb. Vase. Biol., 1998, 18, 397; Takeya, M. et al., Hum. Pathol., 1993, 24, 534; Yla-Herttuala, S., et al., Proc. Natl. Acad. Sci. USA, 1991, 88, 5252; Nelken, N. A., J. Clin. Invest., 1991, 88, 1121), rheumatoid arthritis (see for example Koch, A. E., et al., J. Clin. Invest., 1992, 90, 772; Akahoshi, T., et al., Arthritis Rheum., 1993, 36, 762; Robinson, E., et al., Clin. Exp. Immunol., 101, 398), nephritis (see for example Noris, M., et al., Lab. Invest., 1995, 73, 804; Wada, T., at al., Kidney Int., 1996, 49, 761; Gesualdo, L., et al., Kidney Int., 1997, 51, 155), nephropathy (see for example Saitoh, A., et al., J. Clin. Lab. Anal., 1998, 12, 1; Yokoyama, H., et al., J. Leukoc. Biol., 1998, 63, 493), pulmonary fibrosis, pulmonary sarcoidosis (see for example Sugiyama, Y., et al., Internal Medicine, 1997, 36, 856), asthma (see for example Karina, M., et al., J. Invest. Allergol. Clin. Immunol., 1997, 7, 254; Stephene, T. H., Am. J. Respir. Crit. Care Med., 1997, 156, 1377; Sousa, A. R., et al., Am. J. Respir. Cell Mol. Biol., 1994, 10, 142), multiple sclerosis (see for example McManus, C., et al., J. Neuroimmunol., 1998, 86, 20), psoriasis (see for example Gillitzer, R., et al., J. Invest. Dermatol., 1993, 101, 127), inflammatory bowel disease (see for example Grimm, M. C., et al., J. Leukoc. Biol., 1996, 59, 804; Reinecker, H. C., et al., Gastroenterology, 1995, 106, 40), myocarditis (see for example Seino, Y., et al., Cytokine, 1995, 7, 301), endometriosis (see for example Jolicoeur, C., et al., Am. J. Pathol., 1998, 152, 125), intraperitoneal adhesion (see for example Zeyneloglu, H. B., et al., Human Reproduction, 1998, 13, 1194), congestive heart failure (see for example Aurust, P., et al., Circulation, 1998, 97, 1136), chronic liver disease (see for example Marra, F., et al., Am. J. Pathol., 1998, 152, 423), viral meningitis (see for example Lahrtz, F., et al., Eur. J. Immunol., 1997, 27, 2484), Kawasaki disease (see for example Wong, M.; et al., J. Rheumatol., 1997, 24, 1179) and sepsis (see for example Salkowski, C. A.; et al., Infect. Immun., 1998, 66, 3569). Furthermore, anti-MCP-1 antibody has been reported to show an inhibitory effect or a therapeutic effect in animal models of rheumatoid arthritis (see for example Schimmer, R. C., et al., J. Immunol., 1998, 160, 1466; Schrier, D. J., J. Leukoc. Biol., 1998, 63, 359; Ogata, H., et al., J. Pathol., 1997, 182, 106), multiple sclerosis (see for example Karpus, W. J., et al., J. Leukoc. Biol., 1997, 62, 681), nephritis (see for example Lloyd, C. M., et al., J. Exp. Med., 1997, 185, 1371; Wada, T., et al., FASEB J., 1996, 10, 1418), Asthma (see for example Gonzalo, J.-A., et al., J. Exp. Med., 1998, 188, 157; Lukacs, N. W., J. Immunol., 1997, 158, 4398), atherosclerosis (see for example Guzman, L. A., et al., Circulation, 1993, 88 (suppl.), 1-371), delayed type hypersensitivity (see for example Rand, M. L., et al., Am. J. Pathol., 1996, 148, 855), pulmonary hypertension (see for example Kimura, H., et al., Lab. Invest., 1998, 78, 571), and intraperitoneal adhesion (see for example Zeyneloglu, H. B., et al., Am. J. Obstet. Gynecol., 1998, 179, 438). A peptide antagonist of MCP-1, MCP-1 (9-76), has been also reported to inhibit arthritis in the mouse model (see Gong, J.-H., J. Exp., 4ed., 1997, 186, 131), as well as studies in MCP-1-deficient mice have shown that MCP-1 is essential for monocyte recruitment in vivo (see Lu, B., et al., J. Exp. Med., 1998, 187, 601; Gu, L., et al., Moll. Cell, 1998, 2, 275).

The published literature indicate that chemokines such as MCP-1 and MIP-1 attract monocytes and lymphocytes to disease sites and mediate their activation and thus are thought to be intimately involved in the initiation, progression and maintenance of diseases deeply involving monocytes and lymphocytes, such as atherosclerosis, restenosis, rheumatoid arthritis, psoriasis, asthma, ulcerative colitis, nephritis (nephropathy), multiple sclerosis, pulmonary fibrosis, myocarditis, hepatitis, pancreatitis, sarcoidosis, Crohn's disease, endometriosis, congestive heart failure, viral meningitis, cerebral infarction, neuropathy, Kawasaki disease, and sepsis (see for example Rovin, B. H., et al., Am. J. Kidney. Dis., 1998, 31, 1065; Lloyd, C., et al., Curr. Opin. Nephrol. Hypertens., 1998, 7, 281; Conti, P., et al., Allergy and Asthma Proc., 1998, 19, 121; Ransohoff, R. M., et al., Trends Neurosci., 1998, 21, 154; MacDermott, R. P., et al., Inflammatory Bowel Diseases, 1998, 4, 54).

The chemokines bind to specific cell-surface receptors belonging to the family of G-protein-coupled seven-transmembrane-domain proteins (reviewed in Horuk, Trends Pharm. Sci., 15, 159-165 (1994)) which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, and promotion of cell migration.

Genes encoding receptors of specific chemokines have been cloned, and it is now known that these receptors are G protein-coupled seven-transmembrane receptors present on various leukocyte populations. So far, at least five CXC chemokine receptors (CXCR1-CXCR5) and eight CC chemokine receptors (CCR1-CCR8) have been identified. For example IL-8 is a ligand for CXCR1 and CXCR2, MIP-1α is that for CCR1 and CCR5, and MCP-1 is that for CCR2A and CCR2B (for reference, see for example, Holmes, W. E., et al., Science 1991, 253, 1278-1280; Murphy P. M., et al., Science, 253, 1280-1283; Neote, K. et al, Cell, 1993, 72, 415-425; Charo, I. F., et al., Proc. Natl. Acad. Sci. USA, 1994, 91, 2752-2756; Yamagami, S., et al., Biochem. Biophys. Res. Commun., 1994, 202, 1156-1162; Combadier, C., et al., The Journal of Biological Chemistry, 1995, 270, 16491-16494, Power, C. A., et al., J. Biol. Chem., 1995, 270, 19495-19500; Samson, M., et al., Biochemistry, 1996, 35, 3362-3367; Murphy, P. M., et al., Annual Review of Immunology, 1994, 12, 592-633). It has been reported that lung inflammation and granuroma formation are suppressed in CCR1-deficient mice (see Gao, J.-L., et al., J. Exp. Med., 1997, 185, 1959; Gerard, C., et al., J. Clin. Invest., 1997, 100, 2022), and that recruitment of macrophages and formation of atherosclerotic lesion decreased in CCR2-deficient mice (see Boring, L., et al., Nature, 1998, 394, 894; Kuziel, W. A., et al., Proc. Natl. Acad. Sci., USA, 1997, 94, 12053; Kurihara, T., et al., J. Exp. Med., 1997, 186, 1757; Boring, L., et al., J. Clin. Invest., 1997, 100, 2552).

Accordingly, drugs which inhibit the binding of chemokines such as MCP-1 and/or MIP-1α to these receptors, e.g., chemokine receptor antagonists, may be useful as pharmaceutical agents which inhibit the action of chemokines such as MCP-1 and/or MIP-1α on the target cells, but the prior art is silent regarding 3-cycloalkylaminopyrrolidine derivatives having such pharmacological effects. The identification of compounds that modulate the function of CCR2 and/or CCR5 represents an excellent drug design approach to the development of pharmacological agents for the treatment of inflammatory conditions and diseases associated with CCR2 and/or CCR5 activation, such as rheumatoid arthritis, lupus and other inflammatory diseases. The present invention provides solutions to a long felt need in the field of chemokine receptor modulators and antagonists.

OBJECTS OF THE INVENTION

With the foregoing in mind, it is an object of the present invention to provide chemokine receptor antagonists and chemokine receptor modulators for treating rheumatoid arthritis.

Another main object of the invention is to provide chemokine receptor antagonists and their use as medicinal agents.

An additional object of the invention is to provide chemokine receptor modulators and their use as medicinal agents.

A further object of the present invention is to provide 3-cycloalkylaminopyrrolidine derivatives.

Another object of the invention relates to novel compounds and medical methods of treatment of inflammation.

A still further object of the invention provides new anti-inflammatory and immunomodulatory bioactive compounds and pharmaceutical compositions thereof that act via antagonism of the CCR2 receptor.

An additional object of the invention provides 3-cycloalkylaminopyrrolidine derivatives and their use as modulators of chemokine receptors.

A still additional object of the invention provides 3-cycloalkylaminopyrrolidine derivatives and their use in treating and preventing atherosclerosis and restenosis.

A further object of the invention provides 3-cycloalkylaminopyrrolidine derivatives and their use as modulators of the CCR5 receptor.

Another main object of the invention provides 3-cycloalkylaminopyrrolidine bioactive compounds and pharmaceutical compositions thereof that act via antagonism of the CCR5 receptor.

Other objects and embodiments of the present invention will be discussed below. However, it is important to note that many additional embodiments of the present invention not described in this specification may nevertheless fall within the spirit and scope of the present invention and/or the claims.

SUMMARY OF THE INVENTION

The present invention is directed to compounds of formulas I and II:

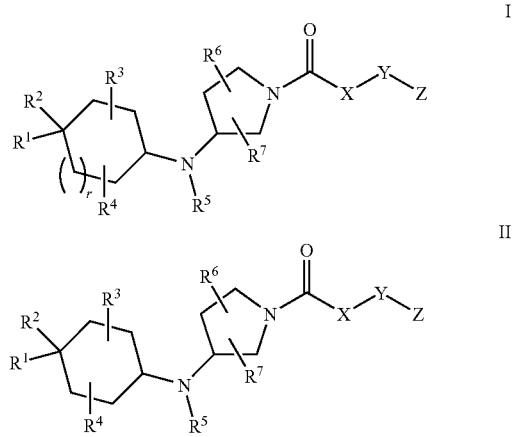

or enantiomers, diastereomers, enantiomerically enriched mixtures, racemic mixtures thereof, prodrugs, crystalline forms, non-crystalline forms, amorphous forms thereof, solvates thereof, metabolites thereof, and pharmaceutically acceptable salts thereof, wherein constituent variables are provided herein.

The instant invention also relates to pharmaceutical compositions which comprise anti-inflammatory and/or immunomodulatory compounds of formula I and II as shown above, that act via antagonism of the CCR2 receptor, (also known as the MCP-1 receptor), therefore inhibiting the Monocyte Chemoattractant Protein-1 (MCP-1).

The instant invention is also directed to pharmaceutical compositions which comprise anti-inflammatory and/or immunomodulatory compounds of formula I and II, as shown above, that act via antagonism of the CCR5 receptor (also known as the MCP-1 receptor), therefore inhibiting the Monocyte Chemoattractant Protein-1 (MCP-1).

The present invention is also directed to compounds of formula I and II which are modulators of CCR2 chemokine receptor function and are useful in the prevention or treatment of inflammatory conditions and diseases such as rheumatoid arthritis, allergic diseases, psoriasis, atopic dermatitis, lupus and asthma.

The present invention also describes compounds of formula I and II which are modulators of CCR5 chemokine receptor function and are useful in the prevention or treatment of inflammatory conditions and diseases such as rheumatoid arthritis, allergic diseases, psoriasis, atopic dermatitis, lupus and asthma.

The invention is also provides pharmaceutical compositions comprising compounds selected from the group of formula I and II, and the use of these compounds and compositions in the prevention or treatment of diseases in which CCR2 chemokine receptors are involved.

The invention further provides pharmaceutical compositions comprising compounds selected from the group of formula I and II, and the use of these compounds and compositions in the prevention or treatment of diseases in which CCR5 chemokine receptors are involved.

The invention additionally provides a method for the treatment of inflammation, rheumatoid arthritis, lupus, systemic lupus erythematosus, atherosclerosis, restenosis, immune disorders, and transplant rejection in a mammal in need thereof comprising administering to such mammal a therapeutically effective amount of a pharmaceutical composition containing a compound according to formula I and II in admixture with a pharmaceutically acceptable excipient, diluent, or carrier.

The present invention further provides compositions comprising a compound of the invention and a pharmaceutically acceptable carrier.

The present invention further provides methods of modulating activity of a chemokine receptor comprising contacting said chemokine receptor with a compound of the invention.

The present invention further provides methods of treating a disease associated with expression or activity of a chemokine receptor in a patient comprising administering to the patient a therapeutically effective amount of a compound of the invention.

DETAILED DESCRIPTION

The instant invention is directed to a compound of the formula I:

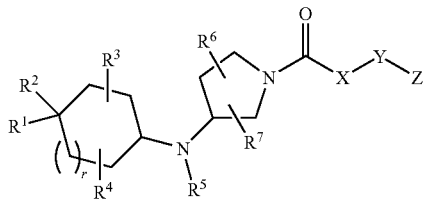

including its enantiomers, diastereomers, enantiomerically enriched mixtures, racemic mixtures thereof, prodrugs, crystalline forms, non-crystalline forms, amorphous forms thereof, solvates thereof, metabolites thereof, and pharmaceutically acceptable salts, wherein:

X is selected from the group consisting of a bond, aryl, mono or poly substituted aryl, heterocycle, mono or poly substituted heterocycle, heteroaryl, mono or poly substituted heteroaryl, carbocycle, mono or poly substituted carbocycle, and $(CR^8R^9)_n$, wherein n=0-5;

Y is a bond, or is selected from the group consisting of oxygen, sulfur, nitrogen, amide bond, thioamide bond, sulfonamide, ketone, —CHOH—, —CHO-alkyl-, -alkyl-O-alkyl, oxime, and a urea;

Z is selected from the group consisting of carbocycle, aryl, heterocycle and heteroaryl, each having 0-3 $R^{10}$ substituents, wherein $R^{10}$ is independently selected from the group consisting of: halogen, alkyl, alkenyl, alkynyl, alkoxy, cyclic alkoxy, heterocyclic alkoxy, alkoxyalkyl, cyclic alkoxyalkyl, heterocyclic alkoxyalkyl, alkylthioalkyl, cyclic alkylthioalkyl, heterocyclic alkylthioalkyl, thioalkyl, mono-, di- or tri-haloalkyl, mono-, di- or tri-haloalkoxy, nitro, amino, mono- or di-substituted amino, mono- or di-substituted aminoalkyl, carboxyl, esterified carboxyl, carboxamido, mono- or di-substituted carboxamido, carbamate, mono- or di-substituted carbamate, sulfonamide, mono- or di-substituted sulfonamide, alkylsulfonyl, cyclic alkylsulfonyl, heterocyclic alkylsulfonyl, arylsulfonyl, heteroarylsulfonyl, alkylcarbonyl, cyclic alkylcarbonyl, heterocyclic alkylcarbonyl, arylcarbonyl, heteroarylcarbonyl, thiocarboxamido, cyano, $R^{10a}$-carbocycle, $R^{10a}$-heterocycle, $R^{10a}$-aryl and $R^{10a}$-heteroaryl, wherein $R^{10a}$ is H, halogen, OH, amino, mono- or di-substituted amino, mono-, di- or tri-haloalkyl, alkoxy, mono-, di- or tri-haloalkoxy, carboxamide, sulfonamide, carbamate, urea or cyano;

$R^1$ is independently selected from the group consisting of: carbocycle, heterocycle, aryl, heteroaryl, arylalkyl, heteroarylalkyl, arylalkenyl, heteroarylalkenyl, arylalkynyl, heteroarylalkynyl, arylaminocarbonyl, heteroarylaminocarbonyl, arylcarboxamido, heteroarylcarboxamido, arylureido, heteroarylureido, aryloxy, heteroaryloxy, arylalkoxy, heteroarylalkoxy, arylamino and heteroarylamino, wherein said carbocycle, heterocycle, aryl or heteroaryl is substituted with 0-3 $R^{1a}$, wherein $R^{1a}$ is independently selected from the group consisting of: halogen, alkyl, alkenyl, alkynyl, alkoxy, cyclic alkoxy, heterocyclic alkoxy, alkoxyalkyl, cyclic alkoxyalkyl, heterocyclic alkoxyalkyl, alkylthioalkyl, cyclic alkylthioalkyl, heterocyclic alkylthioalkyl, hydroxyalkyl, mono-, di- or tri-haloalkyl, mono-, di- or tri-haloalkoxy, nitro, amino, mono- or di-substituted amino, mono- or di-substituted aminoalkyl, aminocarbonyl, mono- or di-substituted aminocarbonyl, cyclic aminocarbonyl, aminosulfonyl, mono- or di-substituted aminosulfonyl, alkylcarbonyl, cyclic alkylcarbonyl, heterocyclic alkylcarbonyl, arylcarbonyl, heteroarylcarbonyl, formyl, alkylsulfonyl, cyclic alkylsulfonyl, heterocyclic alkylsulfonyl, arylsulfonyl, heteroarylsulfonyl, carboxylic acid, esterified carboxylic acid, alkylcarbonylamino, cyclic alkylcarbonylamino, heterocyclic alkylcarbonylamino, arylcarbonylamino, heteroarylcarbonylamino, cyano, arylalkyl, heteroarylalkyl, aryloxyalkyl, heteroaryloxyalkyl, arylthioalkyl, heteroarylthioalkyl, carbamate, mono- or di-substituted carbamate, $R^{1b}$-carbocycle, $R^{1b}$-heterocycle, $R^{1b}$-aryl and $R^{1b}$-heteroaryl, wherein $R^{1b}$ is H, halogen, OH, amino, mono- or di-substituted amino, mono-, di- or tri-haloalkyl, alkoxy, mono-, di- or tri-haloalkoxy, hydroxyalkyl, alkoxyalkyl, aminoalkyl, mono- or di-substituted aminoalkyl, carboxamide, sulfonamide, carbamate, urea or cyano;

$R^2$ is independently selected from the group consisting of: H, amino, mono- or di-substituted amino, OH, carboxyl, esterified carboxyl, carboxamide, N-monosubstituted carboxamide, and N,N-disubstituted carboxamide, cyano, alkyl, alkenyl, alkynyl, cycloalkyl, cycloalkenyl, alkoxy, thioalkyl, mono-, di- or tri-haloalkyl, halogen, aryl and heteroaryl;

optionally $R^1$ and $R^2$ can be bonded to each other to form a spirocycle;

$R^3$ and $R^4$, are independently selected form the group consisting of: H, amino, OH, alkyl, haloalkyl, dihaloalkyl, trihaloalkyl, alkenyl, alkynyl, aryl, heteroaryl, arylalkyl, heteroarylalkyl, alkoxy and thioalkyl;

optionally $R^3$ and $R^4$ can occupy multiple positions in the cycloalkyl ring;

optionally $R^1$ and $R^3$ can be cyclized to form a carbocycle or heterocycle having 0-3 $R^a$ substituents, wherein $R^a$ is selected from the group consisting of halogen, alkyl, alkoxy, thioalkyl, mono-, di- or tri-haloalkyl, mono-, di- or tri-haloalkoxy, nitro, amino, carboxyl, esterified carboxyl, carboxamido, thiocarboxamido, cyano, mono-, di-, or poly-substituted aryl or mono-, di-, or poly-substituted heterocycle optionally, wherein said substituted aryl and substituted heterocycle are substituted with 0-3 $R^b$, wherein $R^b$ is selected from the group consisting of halogen, alkyl, alkoxy, thioalkyl, mono-, di- or trihaloalkyl, mono-, di- or trihaloalkoxy, nitro, amino, carboxyl, esterified carboxyl, carboxamido, thiocarboxamido and cyano;

optionally $R^3$ and $R^4$ can be cyclized to form a bridged bicyclic system having a methylene group or an ethylene group or a heteroatom selected form the group consisting of N, O and S;

optionally R³ and R⁴ can be cyclized to form a spirocycle;

R⁵ is independently selected from the group consisting of hydrogen, alkyl, and formyl; and when R⁵ is alkyl the nitrogen may optionally be in the N-oxide form;

R⁶ and R⁷ are each independently selected from the group consisting of H; $C_1$-$C_{10}$ alkyl, wherein said $C_1$-$C_{10}$ alkyl can be optionally interrupted by oxygen (O), nitrogen (NH), or sulfur (S); carbocycle; heterocycle; alkoxy; cycloalkoxy; heterocycloalkoxy; mono-, di- or tri-haloalkyl; mono-, di- or tri-haloalkoxy; aryloxy; heteroaryloxy; arylalkoxy; heteroarylalkoxy; aryloxyalkyl; heteroaryloxyalkyl; arylalkoxyalkyl; heteroarylalkoxyalkyl; aryl; heteroaryl; arylalkyl; heteroarylalkyl; hydroxyalkyl; alkoxyalkyl; cycloalkyloxyalkyl; heterocycloalkyloxyalkyl; aminoalkyl; mono- or di-substituted aminoalkyl; arylaminoalkyl; heteroarylaminoalkyl; alkylthioalkyl; cycloalkylthioalkyl; heterocycloalkylthioalkyl; arylthioalkyl; heteroarylthioalkyl; alkylsulfonylalkyl; cycloalkylsulfonylalkyl; heterocycloalkylsulfonylalkyl; arylsulfonylalkyl; heteroarylsulfonylalkyl; aminocarbonyl; mono- or di-substituted aminocarbonyl; aminocarbonylalkyl; mono- or di-substituted aminocarbonylalkyl; alkylcarbonylalkyl; cycloalkylcarbonylalkyl; heterocycloalkylcarbonylalkyl; alkylcarbonylaminoalkyl; cycloalkylcarbonylaminoalkyl; heterocycloalkylcarbonylaminoalkyl; arylcarbonylaminoalkyl; heteroarylcarbonylaminoalkyl; arylsulfonylaminoalkyl; and heteroarylsulfonylaminoalkyl;

optionally, R⁶ and R⁷ can be cyclized to form a carbocycle or heterocycle, or a spirocycle or spiroheterocycle;

R⁸ and R⁹ are independently selected from the group consisting of H, OH, amino, alkyl, arylalkyl, heteroarylalkyl, aryl, heteroaryl, alkoxy, alkenyl, alkynyl, alkoxyalkyl, mono- or di-substituted amino, a carbocycle and a heterocycle;

optionally R⁸ and R⁹ can be cyclized to form a 3-7 membered carbocycle or heterocycle; and r=0-3.

In a further embodiment, the invention relates to a compound of the formula II:

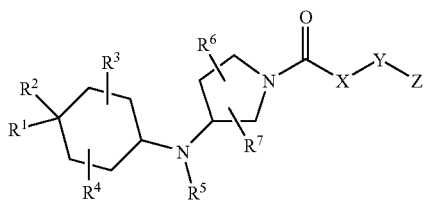

II including its enantiomers, diastereomers, enantiomerically enriched mixtures, racemic mixtures thereof, prodrugs, crystalline forms, non-crystalline forms, amorphous forms thereof, solvates thereof, metabolites thereof, and pharmaceutically acceptable salts, wherein constituent variables are provided hereinabove.

In some embodiments, X can be selected from aryl, mono or poly substituted aryl, heterocycle, heteroaryl, mono or poly substituted heteroaryl, carbocycle, mono or poly substituted carbocycle, and $(CR^8R^9)_n$ wherein n=0-5 (e.g., n is 0, 1, 2, 3, 4, or 5).

In some embodiments, X is a bond, heterocycle, mono or poly substituted heterocycle, heteroaryl, mono or poly substituted heteroaryl, or $(CR^8R^9)_n$ wherein n=0-3.

In some embodiments, X is a heterocycle, mono or poly substituted heterocycle, heteroaryl, or mono or poly substituted heteroaryl.

In some embodiments, X is $(CR^8R^9)_n$ wherein n=0-3.

In some embodiments, X is $CH_2$.

In some embodiments, Y is a bond or -alkyl-O-alkyl-.

In some embodiments, —X—Y— is —$(CR^8R^9)_n$—NH—CO—, -alkyl-O-alkyl-, heterocycle, or heteroaryl.

In some embodiments, —X—Y— is —$CH_2$—NH—CO—, —$CH_2$—O—$CH_2$—, azetidine, pyrrolidine, piperidine, imidazole, or 4,5-dihydroisoxazole.

In some embodiments, —X—Y— is —$CH_2$—NH—CO—.

In some embodiments, Z is aryl or heteroaryl, each substituted with 0-3 $R^{10}$ substituents.

In some embodiments, Z is 6-membered aryl or 6-membered heteroaryl, each substituted with 0-3 $R^{10}$ substituents.

In some embodiments, Z is phenyl, pyridyl or pyrimidinyl, each substituted with 0-3 $R^{10}$ substituents.

In some embodiments, Z is phenyl, pyridyl or pyrimidinyl, each substituted with at least one mono-, di- or tri-haloalkyl.

In some embodiments, Z is:

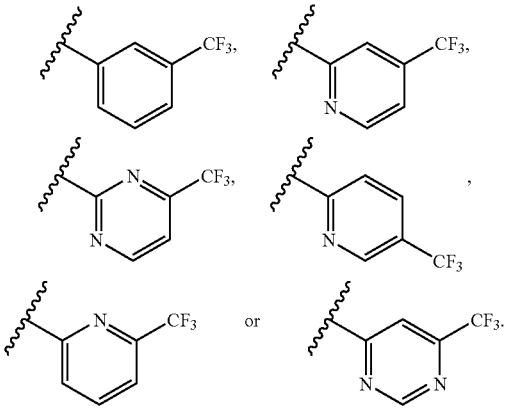

In some embodiments, Z is:

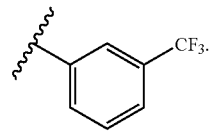 [SMILES: *c1cccc(C(F)(F)F)c1]

In some embodiments, the carbocycle substituent of $R_1$ is intended to include, for example, cycloalkyl of 3-10 carbon atoms, and bicyclic and multicyclic bridged systems such as norbornanyl, adamantyl and bicyclo[2.2.2]octyl. The carbocycle of $R^1$ may also be further substituted with a heterocycle or heteroaryl ring such as pyridyl, pyrrolidinyl, and all those defined under X above.

Specific examples of $R^1$ substituents include phenyl, pyridin-2-yl, 4-methylphenyl, 3-methyl-phenyl, 2-methylphenyl, 4-bromophenyl, 3-bromophenyl, 4-chlorophenyl, 3-chlorophenyl, 4-trifluoromethylphenyl, 3-trifluoromethylphenyl, 2-trifluoromethylphenyl, 2-methoxyphenyl, 3-pyridyl, 4-pyridyl, 2-methoxy-5-pyridyl, 2-ethoxy-5-pyridyl, 3,4-methylenedioxyphenyl, 4-fluorophenyl, 3-trifluoromethyl-1H-pyrazol-1-yl, 3-fluorophenyl, 4-methoxyphenyl, 3-methoxyphenyl, pyridin-4-yl, pyridin-3-yl, 5-methylpyridin-2-yl, 6-methylpyridin-2-yl, quinolin-4-yl, 3-methyl-1H-pyrazol-1-yl, 3,5-dimethyl-1H-pyrazol-1-yl, 4-trifluoromethylphenyl, 3-trifluoromethylphenyl, 3,4-methylenedioxyphenyl, 4-cyanophenyl, 4-(methylaminocarbonyl) phenyl, 1-oxidopyridin-4-yl, pyridin-2-yl, pyridin-3-yl, pyridin-4-yl, 4-methylpyridin-2-yl, 5-methyl-pyridin-2-yl, 6-methylpyridin-2-yl, 6-methoxypyridin-2-yl, 6-methoxypyridin-3-yl, 6-methylpyridin-3-yl, 6-ethylpyridin-3-yl, 6-isopropylpyridin-3-yl, 6-cyclopropylpyridin-3-yl, 1-oxidopyridin-3-yl, 1-oxidopyridin-2-yl, 3-cyanophenyl, 3-(methylaminocarbonyl)-phenyl, 4-(morpholin-4-ylcarbonyl)phenyl, 5-(morpholin-4-ylcarbonyl)pyridin-2-yl, 6-(morpholin-4-ylcarbonyl)pyridin-3-yl, 4-(4-methylpiperazin-1-yl-carbonyl)phenyl, 6-(azetin-1-yl)pyridin-3-yl, 5-cyanopyridin-2-yl, 6-cyanopyridin-3-yl, 5-(methoxy-methyl)pyridin-2-yl, 5-(1-hydroxy-1-methylethyl)pyridin-2-yl, 5-dimethylaminomethyl, 4-ethylaminocarbonylphenyl, 4-isopropylaminocarbonylphenyl, 4-tert-butylamino-carbonylphenyl, 4-dimethylaminocarbonyl-phenyl, 4-(azetidin-1-yl)carbonylphenyl, 4-(pyrrolidin-1-yl)carbonylphenyl, 4-(morpholin-4-yl)carbonylphenyl, 4-(dimethyl-aminocarbonyl)-2-methylphenyl, 2-methyl-4-(methylamino-carbonyl)phenyl, 3-methyl-4-(methylaminocarbonyl)phenyl, 4-(dimethylaminocarbonyl)-3-methylphenyl, 3-methyl-4-(pyrrolidin-1-ylcarbonyl)phenyl, 4-(dimethylaminocarbonyl)-3-fluorophenyl, 4-[(2,2,2-trifluoroethyl)aminocarbonyl]phenyl, 3-fluoro-4-methylaminocarbonyl-phenyl, 4-ethyl-aminocarbonyl-3-fluorophenyl, 3-methylaminocarbonylphenyl, 3-dimethyl-aminocarbonylphenyl, 5-dimethylaminocarbonyl-2-methoxyphenyl, 2-methoxy-5-methyl-aminocarbonylphenyl, 3-(methylaminocarbonylamino) phenyl, 6-(morpholin-4-yl)-pyridin-3-yl, 6-dimethylaminopyridin-3-yl, 6-isopropylaminopyrid-3-yl, 6-(pyrrolidin-1-yl)pyridin-3-yl, 6-cyclopropylaminopyridin-3-yl, 6-ethoxypyridin-3-yl, 6-(2-fluoroethoxy)pyridin-3-yl, 6-(2,2-difluoroethoxy)pyridin-3-yl, 6-(2,2,2-trifluoroethoxy)-pyridin-3-yl, 4-iodophenyl, 5-(pyrrolidin-1-ylcarbonyl)-2-pyridyl, 5-(morpholin-4-yl-carbonyl)-2-pyridyl, 5-dimethylaminocarbonyl-2-pyridyl, 4-methylaminocarbonyl-aminophenyl, 6-(1-hydroxy-1-methylethyl)pyridin-3-yl, 4-(1-hydroxy-1-methylethyl)-phenyl, 4-(methoxymethyl) phenyl, 3-fluoro-4-(methoxymethyl)phenyl, 4-(dimethylamino)phenyl, 4-(dimethylamino)-3-fluorophenyl, 1H-indazol-5-yl, 1-methyl-1H-indazol-5-yl, 2-methyl-1H-indazol-5-yl, 1,3-thiazol-2-yl, 5-ethyl-1,3-thiazol-2-yl, 5-(methyl-aminocarbonyl)-1,3-thiazol-2-yl, 1,3-thiazole-5-yl, 2-(methoxycarbonylamino)-1,3-thiazol-5-yl, 2-isopropyl-1,3-thiazol-5-yl, 5-(pyridin-3-yl)-1,3-thiazol-2-yl, 5-(morpholin-4-ylcarbonyl)-1,3-thiazol-2-yl, 5-aminocarbonyl-1,3-thiazol-2-yl, 5-dimethylaminocarbonyl-1,3-thiazol-2-yl, 5-(pyrrolidin-1-ylcarbonyl)-1,3-thiazol-2-yl, 5-allyl-1,3-thiazol-2-yl, 5-propyl-1,3-thiazol-2-yl, 5-ethylaminocarbonyl-1,3-thiazol-2-yl, 5-phenyl-1,3-thiazol-2-yl, 5-methyl-1,3-thiazol-2-yl, 5-hydroxymethyl-1,3-thiazol-2-yl, 5-(1-hydroxy-1-methylethyl)-1,3-thiazol-2-yl, 5-methoxymethyl-1,3-thiazol-2-yl, 5-(2-pyridyl)-1,3-thiazol-2-yl, 2-(pyrrolidin-1-yl)-1,3-thiazol-4-yl, 2-(morpholin-4-yl)-1,3-thiazol-4-yl, 2-methyl-1,3-thiazol-5-yl, 2-(1-hydroxy-1 methylethyl)-1,3-thiazol-5-yl, 2-(pyrrolidin-1-yl)-1,3-thiazol-5-yl, 2-ethoxy-1,3-thiazol-5-yl, 2-ethyl-1,3-thiazol-5-yl, 2-(pyrrolidin-1-ylmethyl)-1,3-thiazol-5-yl, 2-(morpholin-4-yl)-1,3-thiazol-5-yl, 2-methoxy-methyl-1,3-thiazol-5-yl, 2-isobutyl-1,3-thiazol-5-yl, 2-ethylaminocarbonyl-1,3-thiazol-5-yl, 2-(pyrrolidin-1-ylcarbonyl)-1,3-thiazol-5-yl, 2-(morpholin-4-ylcarbonyl)-1,3-thiazol-5-yl, 2-(3-pyridyl)-1,3-thiazol-5-yl, 2-(2-pyridyl)-1,3-thiazol-5-yl, 4-methyl-1,3-thiazol-2-yl, 1,3-benzo-thiazol-2-yl, pyrimidin-5-yl, pyrimidin-2-yl, pyridazin-4-yl, pyridazin-3-yl, pyrazin-2-yl, 2-methoxypyrimidin-5-yl, 2-ethoxypyrimidin-5-yl, 2-(2-fluoroethoxy)pyrimidin-5-yl, 2-methylpyrimidin-5-yl, 2-ethylpyrimidin-5-yl, 2-isopropylpyrimidin-5-yl, 2-cyclopropylpyrimidin-5-yl, pyrimidin-4-yl, 4-(pyrimidin-5-yl)phenyl, 4-(1,3-oxazol-2-yl)phenyl, 4-(1H-imidazol-1-yl)phenyl, 4-(morpholin-4-yl)phenyl, 5-(pyrazin-2-yl)pyridin-2-yl, 4-(1-methyl-1H-imidazol-5-yl)phenyl, 4-(4,6-dimethylpyrimidin-5-yl)phenyl, 6-bromopyridin-3-yl, 5-bromopyridin-2-yl, 4'-(methylsulfonyl)biphenyl-4-yl, 3'-(methylsulfonyl)biphenyl-4-yl, 3'-(methoxy-carbonyl)-biphenyl-4-yl, 4-(2,3-dihydro-1,4-benzodioxin-6-yl)phenyl, 4'-(dimethyl-amino)-biphenyl-4-yl, 4-(pyridin-3-yl)phenyl, 4-(1H-pyrazol-4-yl) phenyl, 4-(3,3'-bipyridin-6-yl), 4-(3,4'-bipyridin-6-yl), 5-(3-acetylphenyl)pyridin-2-yl, 5-[3-(dimethyl-amino)phenyl] pyridin-2-yl, 5-[3-(trifluoromethyl)phenyl]pyridin-2-yl, 5-[4-(methyl-sulfonyl)phenyl]pyridin-2-yl, 5-(4-methoxyphenyl)pyridin-2-yl, 5-(3-methoxy-phenyl)-pyridin-2-yl, 5-[3-(aminocarbonyl)-phenyl]pyridin-2-yl, 5-(4-fluoro-phenyl)pyridin-2-yl, 5-(3,4-difluorophenyl)pyridin-2-yl, 5-(3,5-dimethylisoxazol-4-yl)pyridin-2-yl, 5-(1-methyl-1H-pyrazol-4-yl)pyridin-2-yl, 5-(1H-pyrazol-4-yl)pyridin-2-yl, 5-(1-benzofuran-2-yl)pyridin-2-yl, 5-(1,3-benzodioxol-5-yl) pyridin-2-yl, 5-(2-formyl-phenyl)pyridin-2-yl, 4-(2'-formylbiphenyl-4-yl, 5-(1,3-oxazol-2-yl)pyridin-2-yl, 6-(1,3-oxazol-2-yl)pyridin-3-yl, 4-(1,3-thizol-2-yl)phenyl, 5-(1,3-thiazol-2-yl)pyridin-2-yl, 6-(1,3-thiazol-2-yl)pyridin-3-yl, 6-(1H-imidazol-1-yl)pyridin-3-yl], 5-(1H-imidazol-1-yl)pyridin-2-yl, 6-phenylpyridin-3-yl, 5-(pyrimidin-5-yl)pyridin-2-yl, 5-(pyrimidin-2-yl)pyridin-2-yl, 5-(3-aminocarbonylphenyl)pyridin-2-yl, 4-(1-methyl-1H-imidazol-4-yl) phenyl, 4-(1H-imidazol-4-yl)phenyl], 5-[2-(hydroxymethyl) phenyl]pyridin-2-yl, 2'-(hydroxymethyl)biphenyl-4-yl, 5-{2-[(dimethylamino)methyl]phenyl}pyridin-2-yl, 2'-[(dimethylamino)methyl]biphenyl-4-yl, 5-fluoromethylpyrazin-2-yl, 5-difluoro-methyl-pyrazin-2-yl, 5-methylpyrazin-2-yl, 2-methyl-pyrimidin-5-yl, 2-fluoromethylpyrimidin-5-yl, 2-difluoromethylpyrimidin-5-yl, 2-trifluoromethylpyrimidin-5-yl, 2-cyclopropylpyrimidin-5-yl, isothiazol-5-yl, 3-methylisothiazol-5-yl, 3-fluoromethylisothiazol-5-yl, 4-(dimethylamino-carbonyl)phenyl, 4-(methylaminocarbonyl)-phenyl, 4-(morpholin-4-ylcarbonyl) phenyl, 4-(piperidin-1-ylcarbonyl)phenyl, 3-fluoro-4-(pyrrolidin-1-ylcarbonyl)phenyl, 5-(pyrrolidin-1-ylcarbonyl)pyridin-2-yl, 5-(dimethyl-aminocarbonyl)pyridin-2-yl, 5-(morpholin-4-yl-carbonyl)-pyridin-2-yl, quinolin-4-yl, 6-methoxypyridin-3-yl, 6-(morpholin-4-yl)pyridin-3-yl, 4-(dimethyl-aminomethyl)phenyl, 5-(dimethylaminomethyl)pyridin-2-yl, 5-(dimethyl-aminocarbonyl)-pyridin-2-yl, 4-[hydroxyl-(pyridin-3-yl)methyl]phenyl, 6-[(hydroxy-(pyridin-3-yl)methyl]pyridin-3-yl, 6-(dimethyl-aminocarbonyl)pyridin-3-yl, 4-(4-hydroxypiperidin-1-ylcarbonyl)phenyl, 4-(4-methoxy-piperidin-1-ylcarbonyl) phenyl, 5-(4-methoxypiperidin-1-ylcarbonyl)-pyridin-2-yl, 6-(4-methoxy-piperidin-1-ylcarbonyl)pyridin-3-yl, phenoxy, benzyloxy, 2-thienyl, 5-(methoxy-methyl)-1,3-thiazol-2-yl, 5-(morpholin-4-ylcarbonyl)-1,3-thiazol-2-yl, 2-isopropyl-1,3-thiazol-5-yl, 2-(methoxymethyl)-1,3-thiazol-5-yl, 5-(methoxymethyl)-1,3-thiazol-2-yl, 4-(pyrimidin-2-yl)phenyl, 4-(pyrimidin-4-yl)phenyl, and 5-(methoxymethyl)pyridin-2-yl.

In some embodiments, $R^1$ is aryl or heteroaryl, each substituted with 0-3 $R^{1a}$.

In some embodiments, $R^1$ is phenyl, pyridyl, pyrimidinyl, pyridazinyl, or thiazolyl, each substituted with 0-3 $R^{1a}$.

In some embodiments, $R^1$ is aryl or heteroaryl, each substituted with 0-3 $R^{1a}$ alkyl, alkoxy, alkoxyalkyl, hydroxyalkyl, mono- or di-substituted aminoalkyl, aminocarbonyl, mono- or di-substituted aminocarbonyl, cyclic aminocarbonyl, alkylcarbonyl, formyl, carboxylic acid, carbamate, mono- or di-substituted carbamate, $R^{1b}$-aryl or $R^{1b}$-heteroaryl.

In some embodiments, $R^1$ is aryl or heteroaryl, each substituted with 0-1 $R^{1b}$-aryl or $R^{1b}$-heteroaryl.

In some embodiments, $R^1$ is aryl or heteroaryl, each substituted with phenyl, pyridyl, pyrimidinyl, oxazolyl, thiazolyl, or imidazolyl.

In some embodiments, $R^1$ is heteroaryl substituted with phenyl, pyridyl, pyrimidinyl, oxazolyl, thiazolyl, or imidazolyl.

In some embodiments, the $R^2$ group can be selected from H, amino, mono- or di-substituted amino, OH, carboxyl, esterified carboxyl, carboxamide, $N(C_1-C_5)$-monosubstituted carboxamide, and $N(C_1-C_5)$, $N(C_1-C_5)$-disubstituted carboxamide, cyano, $(C_1-C_8)$alkyl, $(C_2-C_8)$-alkenyl, $(C_2-C_8)$ alkynyl, $(C_5-C_7)$-cycloalkyl, $(C_5-C_7)$-cycloalkenyl, alkoxy, alkoxyalkyl, thioalkyl, mono-, di- or trihaloalkyl, halogen, aryl or heteroaryl.

In some embodiments, $R^2$ is H or OH.

In some embodiments, $R^2$ is OH.

In some embodiments, $R^1$ is aryl or heteroaryl, each substituted with 0-1 $R^{1b}$-aryl or $R^{1b}$-heteroaryl; and $R^2$ is OH.

In some embodiments, the $R^3$ and $R^4$ group substituents can be independently selected form the group consisting of: H, amino, OH, $(C_1-C_8)$alkyl, halo$(C_1-C_5)$alkyl, dihalo$(C_1-C_5)$alkyl, trihalo$(C_1-C_5)$alkyl, $(C_2-C_8)$alkenyl, $(C_2-C_8)$alkynyl, aryl, heteroaryl, arylalkyl, heteroarylalkyl, $(C_1-C_5)$ alkoxy and thio$(C_1-C_5)$alkyl.

In some embodiments, $R^3$ and $R^4$ are both H.

In some embodiments, the $R^5$ substituent can be independently selected from hydrogen, $(C_1-C_8)$alkyl, formyl; and when $R^5$ is alkyl, the nitrogen may optionally be in the N-oxide form.

In some embodiments, $R^5$ is H.

In some embodiments, the $R^6$ and $R^7$ substituents are each independently selected from the group consisting of H, $C_1-C_{10}$ alkyl, optionally $C_1-C_{10}$ alkyl can be interrupted by oxygen, nitrogen or sulfur, carbocycle, heterocycle, alkoxy, mono-, di- or tri-haloalkyl, mono-, di- or tri-haloalkoxy, cycloalkoxy, heterocycloalkoxy, aryloxy, heteroaryloxy, arylalkoxy, heteroarylalkoxy, aryloxyalkyl, heteroaryloxyalkyl, arylalkoxyalkyl or heteroarylalkoxyalkyl; aryl, heteroaryl, arylalkyl, heteroarylalkyl, hydroxyalkyl, alkoxyalkyl, cycloalkyloxyalkyl, heterocycloalkyloxyalkyl, aminoalkyl, mono- or di-substituted aminoalkyl, arylaminoalkyl, heteroarylaminoalkyl, alkylthioalkyl, cycloalkylthioalkyl, heterocycloalkylthioalkyl, arylthioalkyl, heteroarylthioalkyl, alkylsulfonylalkyl, cycloalkylsulfonylalkyl, heterocycloalkylsulfonylalkyl, arylsulfonylalkyl, heteroarylsulfonylalkyl, aminocarbonyl, mono- or di-substituted aminocarbonyl, aminocarbonylalkyl, mono- or di-substituted aminocarbonylalkyl, alkylcarbonylalkyl, cycloalkylcarbonylalkyl, heterocycloalkylcarbonylalkyl, alkylcarbonylaminoalkyl, cycloalkylcarbonylaminoalkyl, heterocycloalkylcarbonylaminoalkyl, arylcarbonylaminoalkyl, heteroarylcarbonylaminoalkyl, arylsulfonylaminoalkyl, and heteroarylsulfonylaminoalkyl. Specific examples of $R^6$ and $R^7$ substituents are the same as those defined for $R^1$ above.

In some embodiments, $R^6$ and $R^7$ are independently selected from H, $C_1-C_{10}$ alkyl, hydroxyalkyl, and alkoxyalkyl.

In some embodiments, one of $R^6$ and $R^7$ is H and the other is H, $C_1-C_{10}$ alkyl, hydroxyalkyl, or alkoxyalkyl.

In some embodiments, $R^6$ and $R^7$ are both H.

In some embodiments, the $R^8$ and $R^9$ substituents are independently selected from the group consisting of H, OH, amino, $(C_1-C_8)$-alkyl, arylalkyl, heteroarylalkyl, aryl, heteroaryl, $(C_1-C_8)$-alkoxy, $(C_2-C_8)$-alkenyl, $(C_2-C_8)$-alkynyl, $(C_1-C_8)$alkoxyalkyl, mono$(C_1-C_8)$— or di$(C_1-C_8)$-substituted amino, a carbocycle, and a heterocycle. When $R^8$ and $R^9$ are cyclized to form a 3-7 membered carbocycle or heterocycle, such groups can be, for example, cyclopropyl, cyclobutyl, cyclopentyl, cyclohexyl, cyclcopentyl, isoxazolyl thiazolyl, dihydrooxazolyl, pyridyl, pyrimidyl, or imidazolyl.

In some embodiments, $R^8$ and $R^9$ are both H.

In some embodiments, r is 0, 1, 2, or 3. In further embodiments, r is 1.

In some embodiments:

X is a bond, heterocycle, mono or poly substituted heterocycle, heteroaryl, mono or poly substituted heteroaryl, or $(CR^8R^9)_n$, wherein n=0-3;

Y is a bond or -alkyl-O-alkyl-;

Z is aryl or heteroaryl, each substituted with 0-3 $R^{10}$ substituents;

$R^1$ is aryl or heteroaryl, each substituted with 0-3 $R^{1a}$;

$R^2$ is H or OH;

$R^3$ and $R^4$ are both H;

$R^5$ is hydrogen, alkyl, or formyl;

$R^6$ and $R^7$ is H, $C_1-C_{10}$ alkyl, hydroxyalkyl, or alkoxyalkyl;

$R^8$ and $R^9$ both H; and r is 1.

In some embodiments:

—X—Y— is —$(CR^8R^9)_n$—NH—CO—, -alkyl-O-alkyl-, heterocycle, or heteroaryl;

Z is aryl or heteroaryl, each substituted with 0-3 $R^{10}$ substituents;

$R^1$ is aryl or heteroaryl, each substituted with 0-3 $R^{1a}$;

$R^2$ is H or OH;

$R^3$ and $R^4$ are both H;

$R^5$ is hydrogen;

$R^6$ and $R^7$ are both H;

$R^8$ and $R^9$ both H; and r is 1.

In some embodiments:

—X—Y— is —$CH_2$—NH—CO—;

Z is phenyl, pyridyl or pyrimidinyl, each substituted with at least one mono-, di- or tri-haloalkyl;

$R^1$ is aryl or heteroaryl, each substituted with phenyl, pyridyl, pyrimidinyl, oxazolyl, thiazolyl, or imidazolyl;

$R^2$ is OH;

$R^3$ and $R^4$ are both H;

$R^5$ is hydrogen;

$R^6$ and $R^7$ are both H;

$R^8$ and $R^9$ both H; and r is 1.

In some embodiments:

—X—Y— is —$CH_2$—NH—CO—;

Z is phenyl substituted with at least one mono-, di- or tri-haloalkyl;

$R^1$ is heteroaryl substituted with pyridyl, pyrimidinyl, oxazolyl, thiazolyl, or imidazolyl;

$R^2$ is OH;

$R^3$ and $R^4$ are both H;

$R^5$ is hydrogen;

$R^6$ and $R^7$ are both H;

$R^8$ and $R^9$ both H; and r is 1.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term aryl groups is intended to include aromatic carbocyclic groups such as phenyl, biphenylyl, indenyl, naphthyl as well as aromatic carbocycles fused to a heterocycle such as benzothienyl, benzofuranyl, indolyl, quinolinyl, benzothiazole, benzooxazole, benzimidazole, isoquinolinyl, isoindolyl, benzotriazole, indazole, and acridinyl.

The term heteroaryl is intended to include mono- and polycyclic aromatic rings containing from 3 to 20, preferably from 4 to 10 ring atoms, at least one of which is a heteroatom such as oxygen, sulphur, phosphorus or nitrogen. Examples of such groups include furyl, thienyl, pyrrolyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, iosquinolinyl, quinoxalinyl, benzthiazolyl, benzoxazolyl, benzothienyl or benzofuryl.

The terms "cyclic alkyl," "cycloalkyl," and "carbocycle" are used interchangably herein to refer to non-aromatic, cyclized hydrocarbons (mono and polycyclic) such as cyclized alkyl, alkenyl, or alkynyl groups. In some embodiments, the cycloalkyl group is $C_{3-14}$, $C_{3-10}$, $C_{3-8}$, $C_{3-7}$, $C_{3-6}$, or $C_{3-5}$. In some embodiments, cycloalkyl moieties each have from 3 to 14, from 3 to 10, or from 3 to 7 ring-forming carbon atoms. In some embodiments, the cycloalkyl group has 0, 1 or 2 double or triple bonds. Examples of cycloalkyl groups include cyclopropyl, cyclobutyl, cyclopentyl, cyclohexyl, cycloheptyl, cyclopentenyl, etc. In the present application, cycloalkyl is also intended to include bridged cyclic hydrocarbons such as adamantyl groups and the like.

Heterocycles are non-aromatic carbocyclic rings (mono or polycyclic) which include one or more heteroatoms such as nitrogen, oxygen or sulfur in the ring. In some embodiments, the ring can be three, four, five, six, seven or eight-membered. In some embodiments, the heterocycle contains 1, 2 or 3 heteroatoms. Heterocycles can be saturated or unsaturated. In some embodiments, heterocycles contain 0, 1 or 2 double bonds or triple bonds. Ring-forming carbon atoms and heteroatoms can also bear oxo or sulfide substituents (e.g., CO, CS, SO, $SO_2$, NO, etc.). Examples of heterocycles include tetrahydrofuranyl, tetrahydrothiophenyl, morpholino, thiomorpholino, azetidinyl, pyrrolidinyl, piperazinyl, piperidinyl, pyrane, dioxane, and thiazolidinyl.

Additionally, when the heteroaryl or heterocyclic groups are nitrogen containing heterocycles, the nitrogen may be modified to exist in the form of the N→O (N oxides) and such oxides are intended to be included within the scope of the instant invention. In the cases of sulfur containing heterocycles, the sulfur oxides are also intended to be included within the scope of the present invention.

Monosubstituted aryl refers to an aryl group having one substituent. Polysubstituted aryl refers to aryl having 2 or more substitutents (such as 2-4 substituents). Monosubstituted heteroaryl refers to a heteroaryl group having one substituent. Polysubstituted heteroaryl refers to heteroaryl having 2 or more substitutents (such as 2-4 substituents). Monosubstituted cycloalkyl (or carbocycle) refers to a cycloalkyl group having one substituent. Polysubstituted cycloalkyl (or carbocycle) refers to cycloalkyl having 2 or more substitutents (such as 2-4 substituents). Monosubstituted heterocycle refers to a heterocycle having one substituent. Polysubstituted heterocycle refers to heterocycle having 2 or more substitutents (such as 2-4 substituents).

The substituents on the aryl groups, arylalkyl groups, heteroaryl groups, heteroarylalkyl groups, carbocycle (cycloalkyl) groups and heterocyclic groups of the invention can be selected from the group consisting of halogen, alkyl, alkoxy, monohaloalkoxy, dihaloalkoxy, trihaloalkoxy, thioalkyl and monohaloalkyl, dihaloalkyl, trihaloalkyl, nitro, amino, carboxyl, esterified carboxyl, carboxamide, thiocarboxamido and cyano. More in particular, the substituents can also be selected from the group consisting of trifluoromethyl, $C_{1-4}$ alkyl, halo, trifluoromethoxy, fluoromethoxy, difluoromethoxy, $C_{1-5}$ alkoxy, $C_{1-5}$ alkanoyl, $C_{1-5}$ alkanoyloxy, $C_{1-5}$ alkylamino, di($C_{1-5}$ alkyl)-amino, $C_{1-5}$ alkanoylamino, nitro, carboxy, carbamoyl, $C_{1-5}$ alkoxycarbonyl, thiol, $C_{1-5}$, sulphon-amido, carbamoyl $C_{1-5}$ alkyl, N—($C_{1-5}$ alkyl)carbamoyl $C_{1-5}$ alkyl, N—($C_{1-5}$ alkyl)$_2$ carbamoyl-$C_{1-5}$ alkyl, hydroxy $C_{1-5}$ alkyl, and $C_{1-5}$ alkoxy $C_{1-4}$ alkyl.

The terms halo or halogen, by themselves or as part of another substituent, mean, unless otherwise stated, a fluorine, chlorine, bromine, or iodine. Similarly, terms such as haloalkyl, are meant to include monohaloalkyl and polyhaloalkyl. For example, the term haloalkyl, such as halo($C_1$-$C_4$) alkyl, is meant to include trifluoromethyl, 2,2,2-trifluoroethyl, 4-chlorobutyl, 3-bromopropyl, and the like.

The term alkyl when used either alone or as a suffix includes straight chain and branched structures such as primary alkyl groups, secondary alkyl groups and tertiary alkyl groups. These groups may contain up to 15, preferably up to 8 and more preferably up to 4 carbon atoms. In some embodiments, the alkyl group is $C_{1-10}$, $C_{1-8}$, $C_{1-6}$, $C_{1-5}$, $C_{1-4}$, or $C_{1-3}$. Examples of alkyl radicals include groups such as methyl, ethyl, n-propyl, isopropyl, n-butyl, t-butyl, isobutyl, and sec-butyl. Similarly the terms alkenyl and alkynyl refer to unsaturated straight or branched structures containing for example from 2 to 12, preferably from 2 to 6 carbon atoms. In some embodiments, the alkenyl or alkynyl group is $C_{2-10}$, $C_{2-8}$, $C_{2-6}$, $C_{2-5}$, $C_{2-4}$, or $C_{2-3}$. Examples of alkenyl and alkynyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

Aralkyl or arylalkyl is meant to refer to an alkyl group substituted by an aryl group. An example arylalkyl group is benzyl. Arylalkenyl refers to an alkenyl group substituted by aryl. Arylalkynyl refers to an alkynyl group substituted by an aryl group. Heteroarylalkyl is meant to refer to an alkyl group substituted by heteroaryl. Heteroarylalkenyl refers to an akenyl group substituted by a heteroaryl. Heteroarylalkynyl refers to an alkynyl group substituted by heteroaryl. Heterocycloalkyl or heterocyclicalkyl is meant to refer to an alkyl group substituted by a heterocycle. Cycloalkylalkyl or cyclic alkyl alkyl is meant to refer to an alkyl group substituted by a cycloalkyl group. Examples of cycloalkylalkyl groups include (cyclohexyl)methyl, cyclopropylmethyl, and the like.

The terms alkoxy, alkylamino and alkylthio (or thioalkoxy) are used in their conventional sense, and refer to those alkyl groups attached to the remainder of the molecule via an oxygen atom, an amino group, or a sulfur atom, respectively.

Therefore, terms such as alkoxy and thioalkyl comprise alkyl moieties as defined above, attached to the appropriate functionality.

Other suitable substituents which can be used in the many carbon rings of the present invention such as cycloaliphatic, aromatic, non-aromatic heterocyclic ring or benzyl group include, for example, —OH, halogen (—Br, —Cl, —I and —F) —O (aliphatic, substituted aliphatic, benzyl, substituted benzyl, phenyl, substituted phenyl, aromatic or substituted aromatic group), —CN, —NO$_2$, —COOH, —NH$_2$, —NH (aliphatic group, substituted aliphatic, benzyl, substituted benzyl, phenyl, substituted phenyl, aromatic or substituted aromatic group), —N(aliphatic group, substituted aliphatic, benzyl, substituted benzyl, phenyl, substituted phenyl, aromatic or substituted aromatic group)$_2$, —COO (aliphatic group, substituted aliphatic, benzyl, substituted benzyl, phenyl, substituted phenyl, aromatic or substituted aromatic group), —CONH$_2$, —CONH (aliphatic, substituted aliphatic group, benzyl, substituted benzyl, phenyl, substituted phenyl, aromatic or substituted aromatic group)), —SH, —S (aliphatic, substituted aliphatic, benzyl, substituted benzyl, phenyl, substituted phenyl, aromatic or substituted aromatic group) and —NH—C=NH)—NH$_2$. A substituted non-aromatic heterocyclic ring, benzylic group or aromatic group can also have an aliphatic or substituted aliphatic group as a substituent. A substituted alkyl or aliphatic group can also have a non-aromatic heterocyclic ring, benzyl, substituted benzyl, aromatic or substituted aromatic group as a substituent. A substituted non-aromatic heterocyclic ring can also have =O, =S, =NH or =N(aliphatic, aromatic or substituted aromatic group) as a substituent. A substituted aliphatic, substituted aromatic, substituted non-aromatic heterocyclic ring or substituted benzyl group can have more than one substituent.

For bivalent moieties such as X and Y, the term "amide bond" refers to —NHCO—; the term "thiamide bond" refers to —NHCS—; the term "sulfonamide" refers to —NHSO$_2$—; the term "ketone" refers to —OC—; the term "oxime" refers to —C(=N—OH)—; and the term "urea" refers to —NHCONH—.

"Cyclic alkoxy" refers to —O-(cycloalkyl). "Heterocyclic alkoxy" refers to —O— (heterocycle). "Alkoxyalkyl" refers to alkyl substituted by alkoxy. "Cyclicalkoxyalkyl" refers to alkyl substituted by —O-(cycloalkyl). "Heterocyclic alkoxy alkyl" refers to alkyl substituted by —O-(heterocycle). "Alkylthioalkyl" refers to alkyl substituted by thioalkyl. "Cyclic alkyl thioalkyl" refers to alkyl substituted by —S-(cycloalkyl). "Heterocyclic alkyl thioalkyl" refers to alkyl substituted by —S-(heterocycle). "Mono- or di-substituted amino" refers to —NH$_2$ wherein either one (e.g., mono) or both (e.g., di) hydrogens are replaced with a substituent such as C$_{1-8}$ alkyl, OH, CO—(C$_{1-4}$ alkyl), etc. "Mono- or di-substituted aminoalkyl" refers to alkyl substituted by mono or di-substituted amino. "Esterified carboxyl" refers to COOH where the hydrogen atom is replaced by a substituent such as C$_{1-8}$ alkyl, carbocycle, heterocycle, aryl or heteroaryl. "Carboxamido" refers to —CONH$_2$. "Mono or di-substituted carboxamide" refers to —CONH$_2$ wherein either one (e.g., mono) or both (e.g., di) hydrogens are replaced with a substituent such as C$_{1-8}$ alkyl, OH, CO—(C$_{1-4}$ alkyl), etc. "Carbamate" refers to —OCONH$_2$ and "mono or di-substituted carbamate" refers to —OCONH$_2$ where either one (e.g., mono) or both (e.g., di) hydrogens are replaced with a substituent such as C$_{1-8}$ alkyl, OH, CO—(C$_{1-4}$ alkyl), etc. "Sulfonamide" refers to —SO$_2$NH$_2$ and "mono or di-substituted sulfonamide" refers to —SO$_2$NH$_2$ wherein either one (e.g., mono) or both (e.g., di) hydrogens are replaced with a substituent such as C$_{1-8}$ alkyl, OH, CO—(C$_{1-4}$ alkyl), etc. "Alkylsulfonyl" refers to —SO$_2$— (alkyl). "Cyclic alkylsulfonyl" refers to —SO$_2$-(carbocycle). "Heterocyclic sulfonyl" refers to —SO$_2$— (heterocycle). "Aryl sulfonyl" refers to —SO$_2$— (aryl). "Heteroaryl sulfonyl" refers to —SO$_2$— (heteroaryl). "Alkylcarbonyl" refers to —CO-(alkyl). "Cyclic alkylcarbonyl" refers to —CO-(cycloalkyl). "Heterocyclic alkylcarbonyl" refers to —CO-(heterocycle). "Arylcarbonyl" refers to —CO-(aryl). "Heteroarylcarbonyl" refers to —CO-(heteroaryl). "Thiocarboxamido" refers to —CSNH$_2$. "Arylaminocarbonyl" refers to —CO—NH-(aryl). "Heteroarylaminocarbonyl" refers to —CO—NH-(heteroaryl). "Arylcarboxamido" refers to —CO—NH-(aryl). "Heteroarylcarboxamido" refers to —CO—NH-(heteroaryl). "Arylureido" refers to ureido substituted by aryl. "Heteroarylureido" refers to ureido substituted by heteroaryl. "Aryloxy" refers to —O-(aryl). "Heteroaryloxy" refers to —O-(heteroaryl). "Arylalkoxy" refers to alkoxy substituted by aryl. "Heteroarylalkoxy" refers to alkoxy substituted by heteroaryl. "Arylamino" refers to —NH-(aryl). "Heteroarylamino" refers to —NH-(heteroaryl). "Hydroxylalkyl" refers to alkyl substituted by hydroxyl (OH). "Aminocarbonylalkyl" refers to alkyl substituted by aminocarbonyl. "Mono- or di-substituted aminocarbonlyalkyl" refers to alkyl substituted by mono- or di-substituted aminocarbonyl. "Alkylcarbonlyalkyl" refers to alkyl substituted by alkylcarbonyl. "Cycloalkylcarbonylalkyl" refers to alkyl substituted by —CO-(cycloalkyl). "Heterocycloalkylcarbonylalkyl" refers to alkyl substituted by —CO-(heterocyle). "Alkylcarbonylaminoalkyl" refers to alkyl substituted by —NH—CO-(alkyl). "Cycloalkylcarbonylaminoalkyl" refers to alkyl substituted by —NH—CO-(cycloalkyl). "Heterocycloalkylcarbonylaminoalkyl" refers to alkyl substituted by —NH—CO-(heterocycle). "Arylcarbonylaminoalkyl" refers to alkyl substituted by —NH—CO-(aryl). "Heteroarylcarbonylaminoalkyl" refers to alkyl substituted by —NH—CO-(heteroaryl). "Arylsulfonylaminoalkyl" refers to alkyl substituted by —NH—SO$_2$— (aryl). "Heteroaylsulfonylaminoalkyl" refers to alkyl substituted by —NH—SO$_2$— (heteroaryl). "Spirocycle" refers to a cycloalkyl group sharing one of its ring-forming atoms with another cycloalkyl or heterocyclyl group. "Spiroheterocycle" refers to a heterocycle group sharing one of its ring-forming atoms with another cycloalkyl or heterocyclyl group.

The phrase "optionally R$^3$ and R$^4$ can be cyclized to form a bridged bicyclic system having a methylene group or an ethylene group or a heteroatom selected form the group consisting of N, O and S" refers to when R$^3$ and R$^4$, residing on different atoms, together form a divalent bridging moiety such as, for example, methylene, ethylene, NH, O, S, methylene-O, methylene-S, or methylene-NH.

Unless otherwise indicated, the compounds provided in the above formula are meant to include pharmaceutically acceptable salts, prodrugs thereof, enantiomers, diastereomers, racemic mixtures thereof, crystalline forms, non-crystalline forms, amorphous forms thereof and solvates thereof.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, phosphoric, partially neutralized phosphoric acids, sulfuric, partially neutralized sulfuric, hydroiodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention may contain both basic and acidic functionalities that allow the compounds to be converted into either base or acid addition salts. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

The neutral forms of the compounds of the present invention may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As noted above, some of the compounds of the present invention possess chiral or asymmetric carbon atoms (optical centers) or double bonds; the racemates, diastereomers, geometric isomers and individual optical isomers are all intended to be encompassed within the scope of the present invention.

Some of the compounds of formula I or II can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are substantially equivalent for the uses contemplated by the present invention and are intended to be within the scope of the present invention.

In addition to salt forms, the present invention provides compounds that may be in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex-vivo environment. For example, prodrugs can be slowly converted to the compounds of the present invention when placed in a transdermal patch reservoir with a suitable enzyme or chemical reagent. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Compounds of the invention, including salts, hydrates, and solvates thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Preparation of compounds of the invention can involve the protection and deprotection of various chemical groups. The need for protection and deprotection, and the selection of appropriate protecting groups can be readily determined by one skilled in the art. The chemistry of protecting groups can be found, for example, in T. W. Greene and P. G. M. Wuts, *Protective Groups in Organic Synthesis*, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

A variety of 4,4-disubstituted cyclohexanone derivatives can be synthesized using the protocols described in Schemes 1. Compounds of formula 1-2 can be prepared by addition of arylMgX or ArX/BuLi to 1,4-cyclohexanedione 1-1. Alternatively, compounds of formula 1-2 can be prepared by treatment of 1,4-cyclohexanedione mono-ethylene ketal 1-3 with arylMgX, ArX/BuLi or heteroarylH/lithium tetramethylpiperidine followed by converting the ketal in 1-4 to a ketone using an acid such as HCl in aqueous solution.

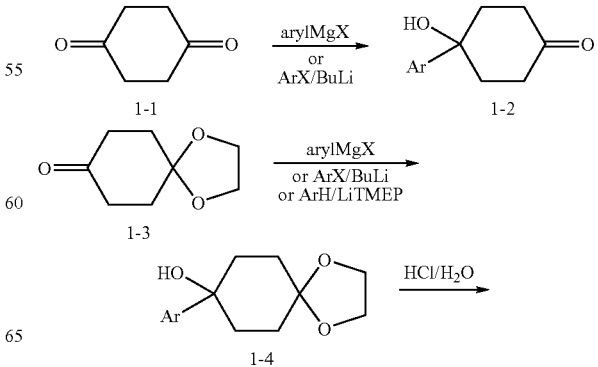

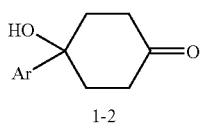

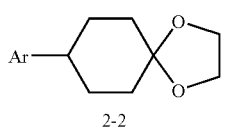

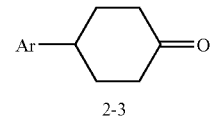

Ar = substituted pyrazole, imidazole, triazole or tetrazole

4-Arylcyclohexanone derivatives of formula 2-3 can be synthesized following the procedures shown in Scheme 2. The intermediate 1-4 is subjected to a treatment with a dehydrating agent such as thionyl chloride/pyridine followed by reduction of the resulting olefin by hydrogenation using a catalyst such as Pd—C or PtO$_2$. Conversion of the ketal in 2-2 by treatment with an acid provides the ketones of formula 2-3.

Scheme 2

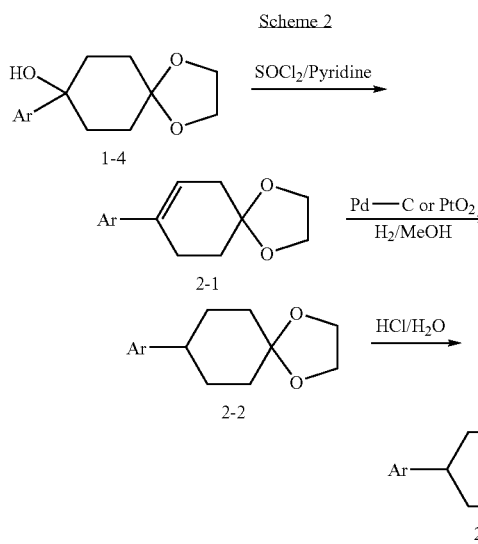

Alternatively, compounds of formula 2-3 can be synthesized according to Scheme 3. Reduction of ketone 1-3 using a reducing agent such as sodium borohydride produces the alcohol 3-1 which is converted to a mesylate 3-2 by treating with methanesulfonyl chloride. Displacement of the mesylate 3-2 with a heterocycle such as pyrazole, imidazole, triazole or tetrazole provides the intermediate 2-2 which is converted to compounds of formula 2-3 by treatment with an acid such as HCl.

Scheme 3

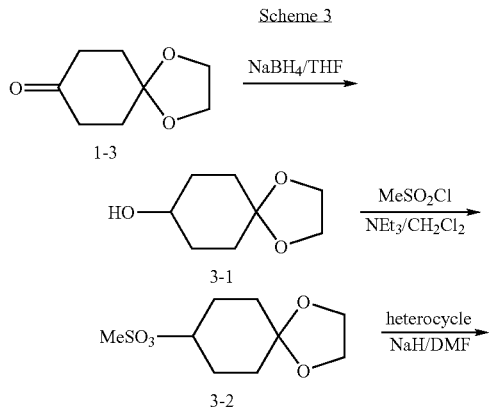

Introduction of a substituent on the aromatic ring in ketones of formula 1-2 or 2-3 can be accomplished starting from the ketal intermediate 1-4 or 2-2 using the methods described in Schemes 4-8. When the aromatic ring in 1-4 or 2-2 bears a cyano group, the ketal 4-1 is subjected to a hydrolysis using a base such as sodium or potassium hydroxide to give the carboxylic acid 4-2. Coupling of 4-2 with an amine using a coupling agent such as BOP provides the amide 4-3. Treatment of 4-3 with an acid such as HCl affords the ketones of formula 4-4.

Scheme 4

When the aromatic ring in the ketal intermediate 1-4 or 2-2 bears a halide such as bromo or iodo, the halide can be transformed to a substitutent using the procedures described in Scheme 5. Treatment of 5-1 with butyl lithium followed by quenching with an electrophile such as alkyl halide, aldehyde, ketone, chloroformate, or carbonate provides the R-substituted ketal 5-2. Suzuki coupling of 5-1 with a boronic acid ArB(OH)$_2$ (Ar=aryl or heteroaryl) or coupling of 5-1 with ArZnCl which can be generated in situ by treating ArX (X=Br, I) with butyl lithium followed by quenching with zinc chloride or treating 5-1 with iPrMgCl followed by coupling with ArX (X—Br, I) in the presence of a catalyst such as Ni(CH$_3$COCH(OH)CH$_3$)$_2$-1,2-bis(diphenylphosphino) ethane provides the Ar-substituted ketal intermediate 5-4. Treatment of 5-2 and 5-4 with an acid affords their corresponding ketones 5-3 and 5-5.

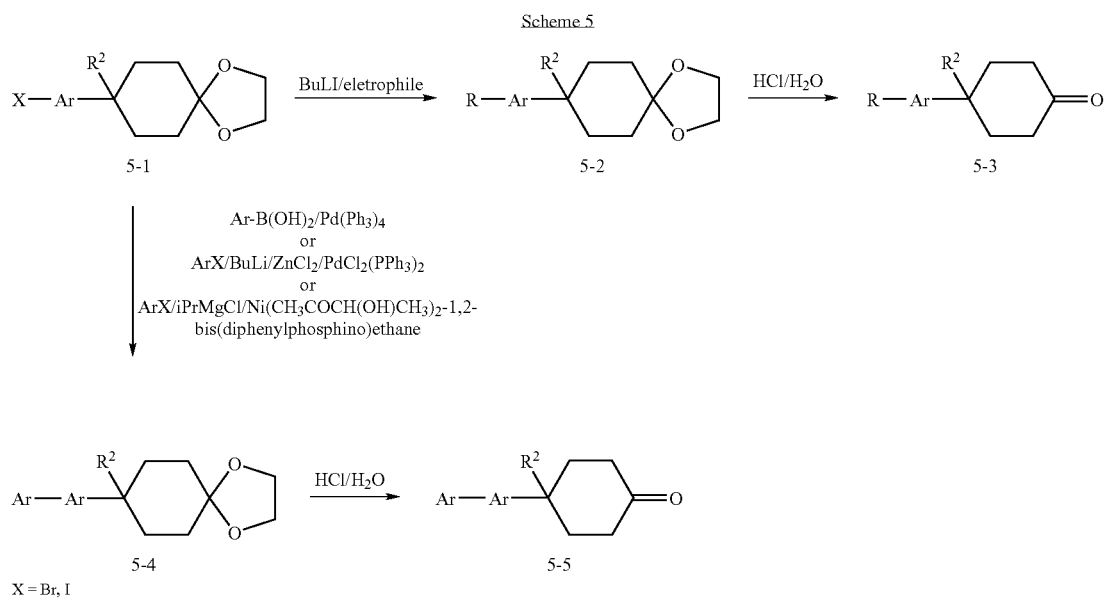

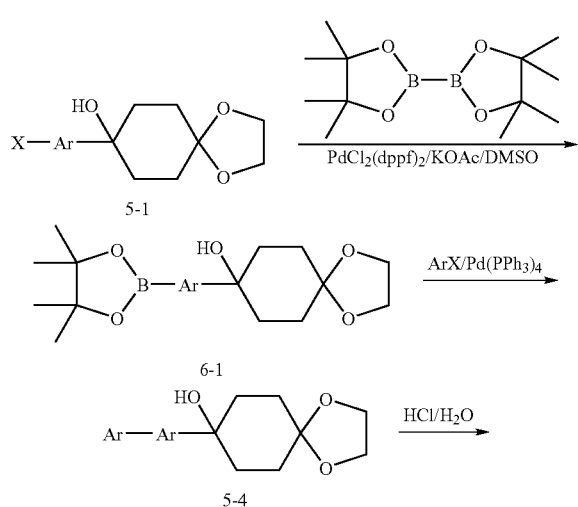

Alternatively, ketones of formula 5-5 can be obtained using the protocol depicted in Scheme 6. Following conversion of 5-1 to a boronic acid ester, the resulting boronic acid ester 6-1 is coupled with ArX (X=Br, I) using a palladium catalyst such as Pd(PPh₃)₄ to give the Ar-substituted ketal 5-4 from which ketones of formula 5-5 are obtained by treatment with an acid such as HCl.

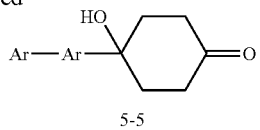

When the Ar group in ketones of formula 1-2 or 2-3 is a 2-thiazole residue, introduction of a substituent at the 5-position on the thiazole can be accomplished using the sequence outlined in Scheme 7. Treatment of thiazole 7-1 with butyl lithium followed by quenching with 1,4-cyclohexanedione mono-ethylene ketal 1-3 gives rise to the tertiary alcohol 7-2. Treatment of 7-2 with butyl lithium followed by quenching the anion 7-3 with an electrophile such as alkyl halide, aldehyde, ketone, chloroformate or carbonate produces the ketal 7-4 with an R substituent at the 5-position on thiazole. Alternatively, the anion 7-3 can be quenched with zinc chloride and the resulting intermediate is coupled with ArX (X=Br, I) using a palladium catalyst such as PdCl₂(PPh₃)₂ to give the ketal 7-6 with an Ar residue at the 5-position on thiazole. Ketals 7-4 and 7-6 are then converted to their corresponding ketones of formula 7-5 and 7-7 by treatment with an acid such as HCl.

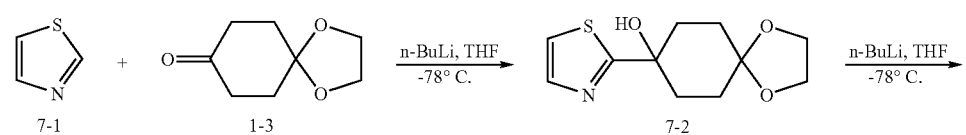

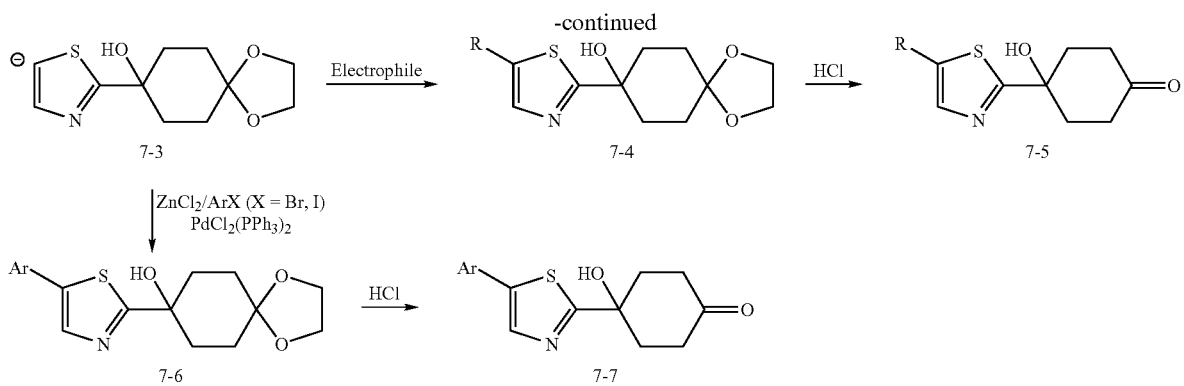

When the Ar group in ketones of formula 1-2 or 2-3 is a 5-thiazole residue, introduction of a substituent at the 2-position on the thiazole can be accomplished using the sequence outlined in Scheme 7. Lithiation of 2-trimethylsilyl protected thiazole 8-1 followed by quenching with 1-3 gives rise to the intermediate 8-2. Following removal of the trimethylsilyl group using TBAF, lithiation of 8-3 followed by quenching with an electrophile such as alkylhalide, aldehyde, ketone, isocyanate, chloroformate or carbonate provides the 5-R-substituted thiazole derivative 8-4. Treatment of 8-4 with an acid such as HCl affords the ketones of formula 8-5.

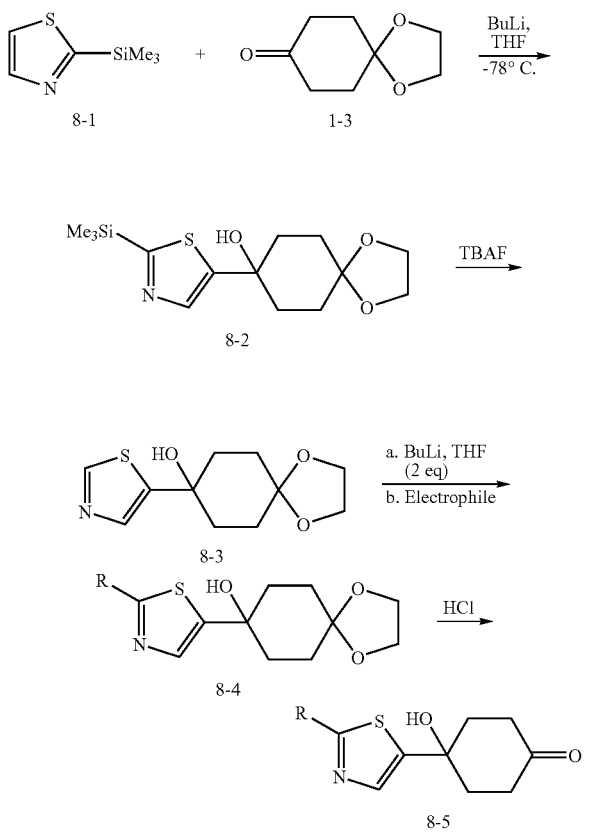

A variety of 3-aminopyrrolidine intermediates can be prepared as shown in Schemes 6-17. Coupling of a carboxylic acid of formula 9-1 with a commercially available pyrrolidine derivative of formula 9-2 using a coupling agent such as BOP gives rise to the amide 9-3. Removal of the protecting group P (P=Boc, benzyl or Cbz) using an acid such as TFA or HCl or by hydrogenation using a palladium catalyst provides the pyrrolidine intermediates of formula 9-4.

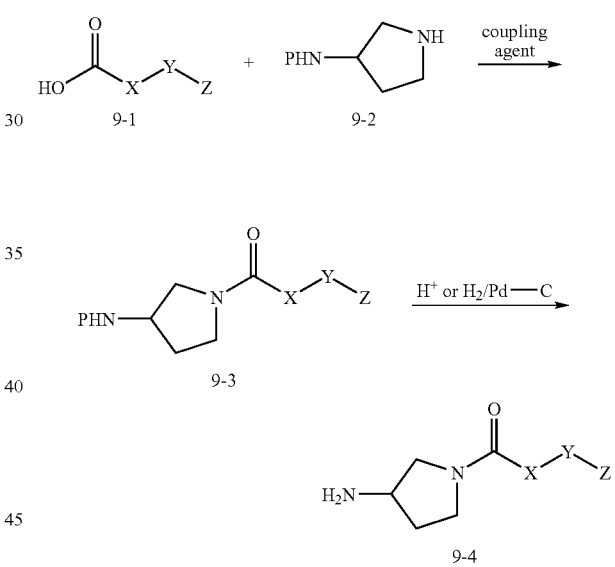

P = Boc, Bn, Cbz

4-Amino-2-methylpyrrolidine derivatives of formula 10-8 can be prepared using the sequence described in Scheme 10. Following Boc protection at the amine and TBS protection at the hydroxyl of trans-4-hydroxy-L-proline methyl ester 10-1, the ester in 10-2 is reduced to an alcohol and the resulting alcohol is converted to a tosylate. Detosylation in 10-3 can be achieved by reduction using lithium triethylborohydride (LiEt$_3$BH). The resulting intermediate 10-4 is subjected to a deprotection using an acid such as HCl to remove the Boc and the TBS groups. Following coupling of the resulting amine 10-5 with a carboxylic acid of formula 9-1 using a coupling agent such as EDC, conversion of the hydroxyl to a mesylate is followed by displacement with sodium azide. The resulting azido group is then reduced to an amine by hydrogenation to give the pyrrolidine intermediates of formula 10-8.

27

Scheme 10

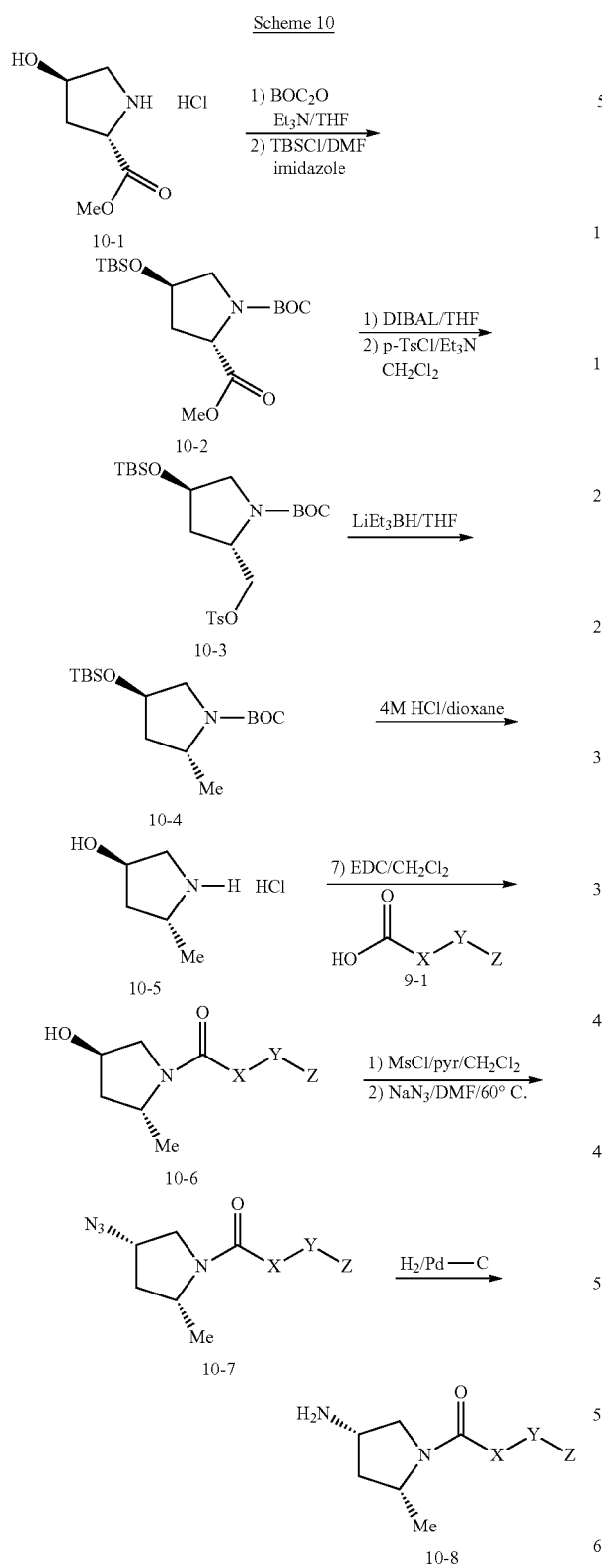

28

(DIBAL), the alcohol is converted to a tosylate and the resulting tosylate is reduced using $LiEt_3BH$ to give 11-2. Intermediate 11-2 is then converted to compounds of formula 11-6 in a manner similar to that described in Scheme 10.

Scheme 11

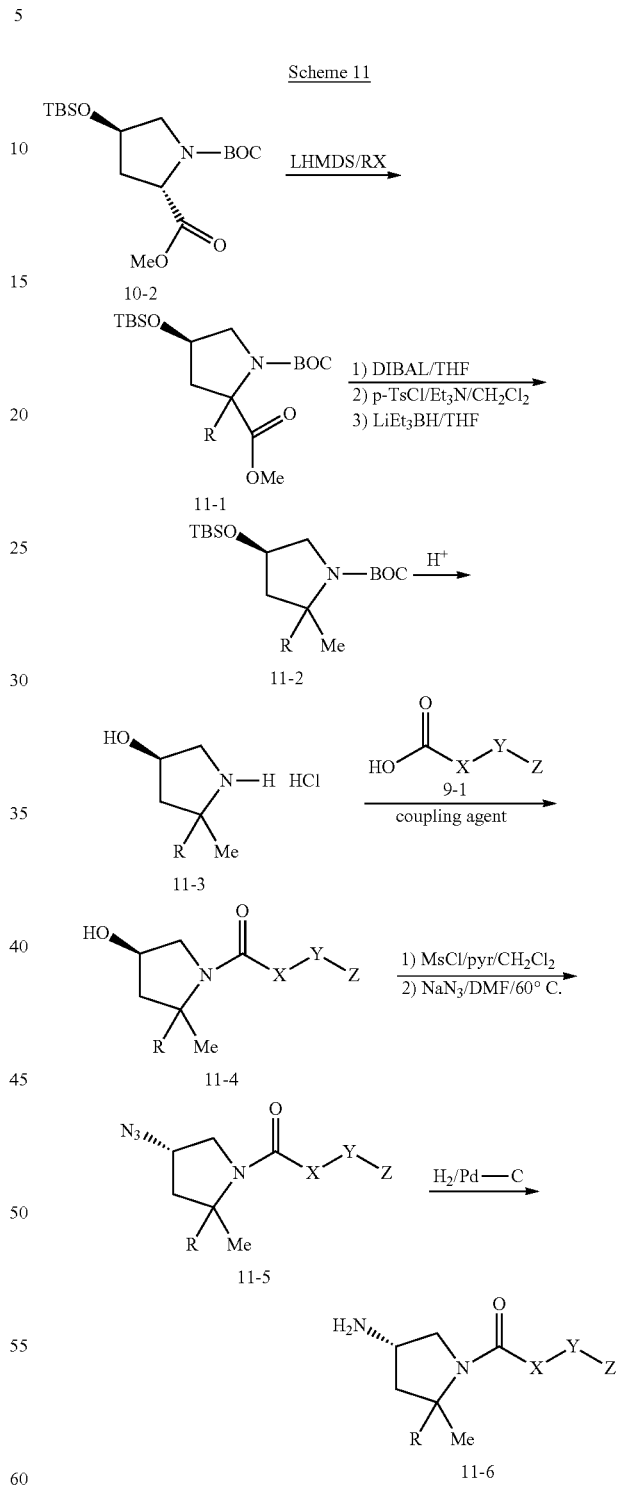

4-Aminopyrrolidine derivatives of formula 11-6 can be prepared according to Scheme 11. Alkylation of the intermediate 10-2 with an alkyl halide (RX) using LHMDS provides the R-substituted intermediate 11-1. Following reduction of the ester to an alcohol using diisobutylaluminum hydride 4-Aminopyrrolidine derivatives of formula 12-5 can be synthesized using the method shown in Scheme 12. The intermediate 10-2 is reduced to an alcohol using a reducing agent such as DIBAL and the resulting alcohol is alkylated with an alkyl halide (RX) using sodium hydride to give intermediate 12-1. Using procedures similar to those described in Scheme 10, compounds of formula 12-5 are obtained from the intermediate 12-1.

protecting groups in 13-2 or 13-3 using an acid such as HCl, the resulting amine 13-4 is condensed with a carboxylic acid of formula 9-1. Mesylation at the 4-hydroxy on the pyrrolidine followed by displacement of the resulting mesylate with sodium azide and reduction of the azido by hydrogenation provides compounds of formula 13-7.

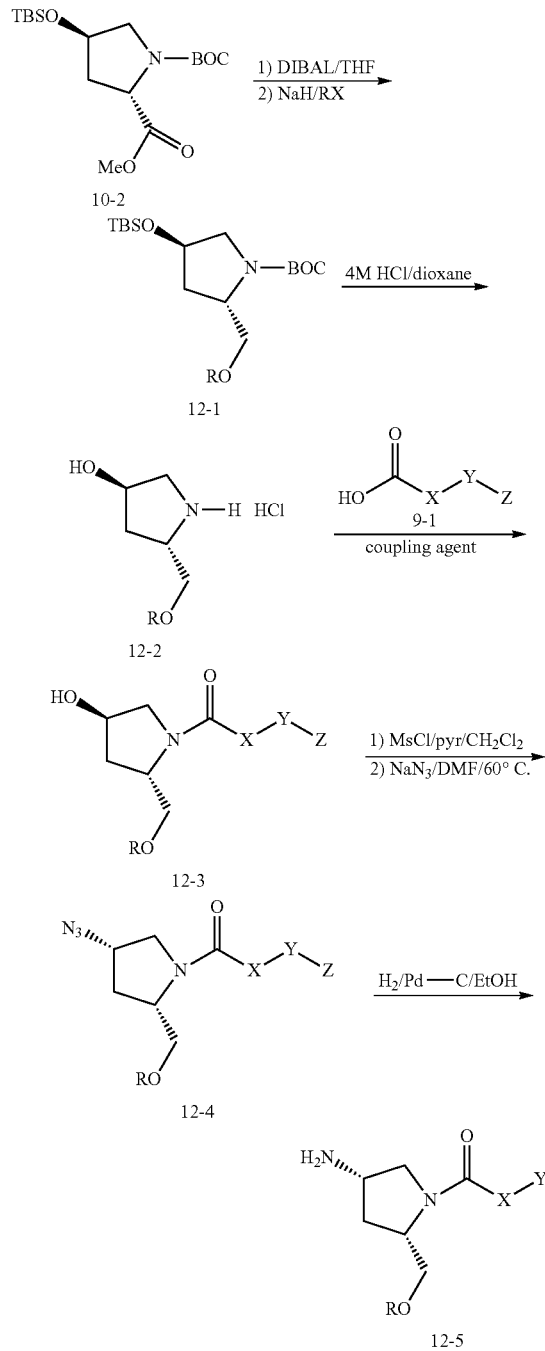

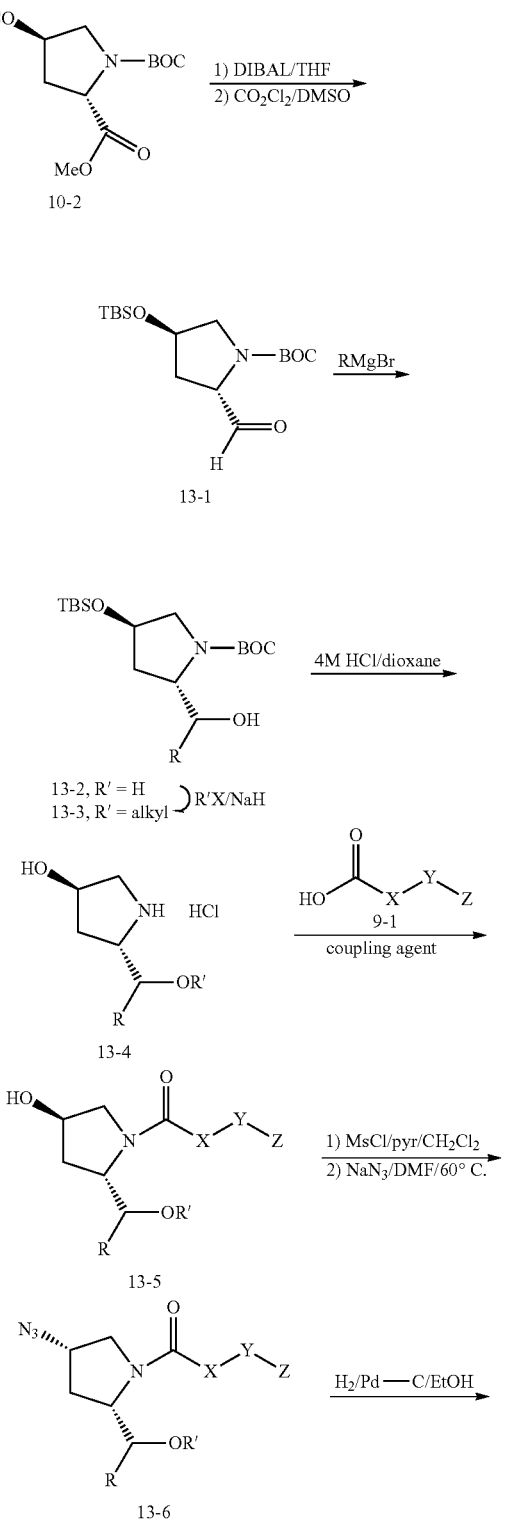

4-Aminopyrrolidine derivatives of formula 13-7 can be generated according to Scheme 13. The intermediate 10-2 is reduced to an alcohol using a reducing agent such as DIBAL and the resulting alcohol is oxidized to an aldehyde using a oxidizing agent such as Swern oxidation. Addition of a Grignard reagent RMgX to the aldehyde 13-1 is followed by alkylation of the resulting alcohol with an alkyl halide (RX) using sodium hydride. After removal of the Boc and TBS

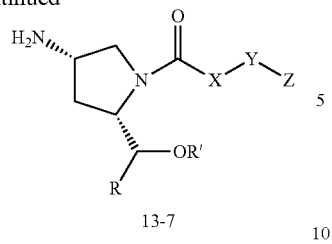

13-7

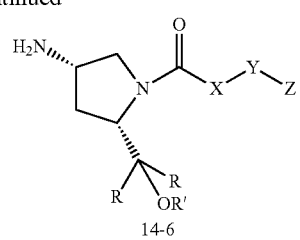

14-6

4-Aminopyrrolidine derivatives of formula 14-6 can be synthesized using a protocol depicted in Scheme 14. After double addition of a Grignard reagent RMgX to the intermediate 10-2, the resulting tertiary alcohol 14-1 is subjected to an alkylation with an alkyl halide (R'X) to give 14-2. Intermediates 14-1 and 14-2 are then converted to compounds of formula 14-6 in a manner similar to that described in Scheme 13.

The synthesis of 4-aminopyrrolidine derivatives of formula 15-5 is given in Scheme 15. After dehydration of the intermediate 14-1 followed by reduction of the olefin by hydrogenation, the resulting intermediate 15-1 is converted to compounds of formula 15-5 in a fashion similar to that described in Scheme 10.

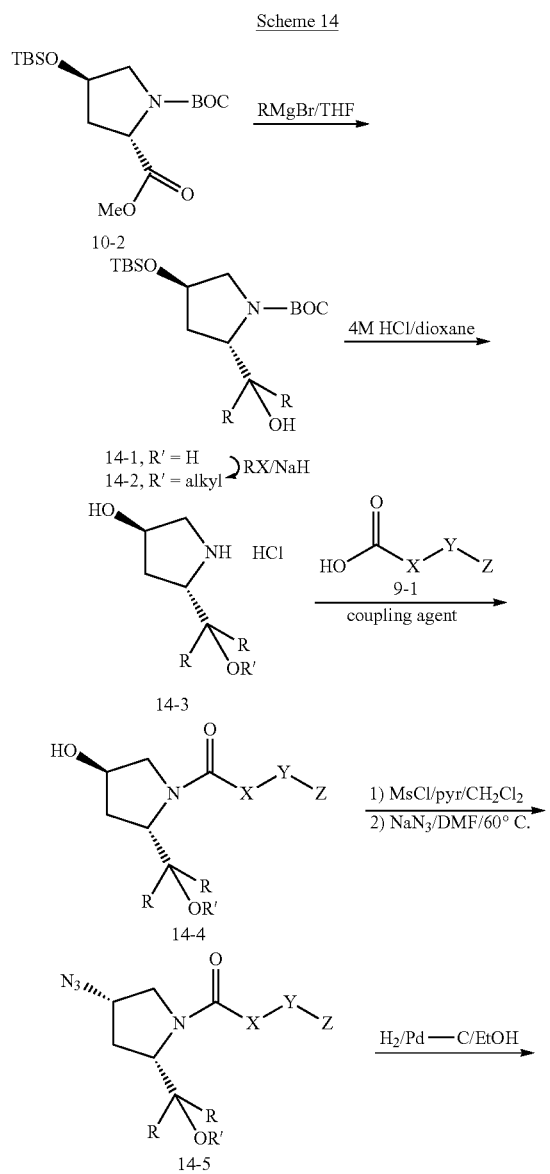

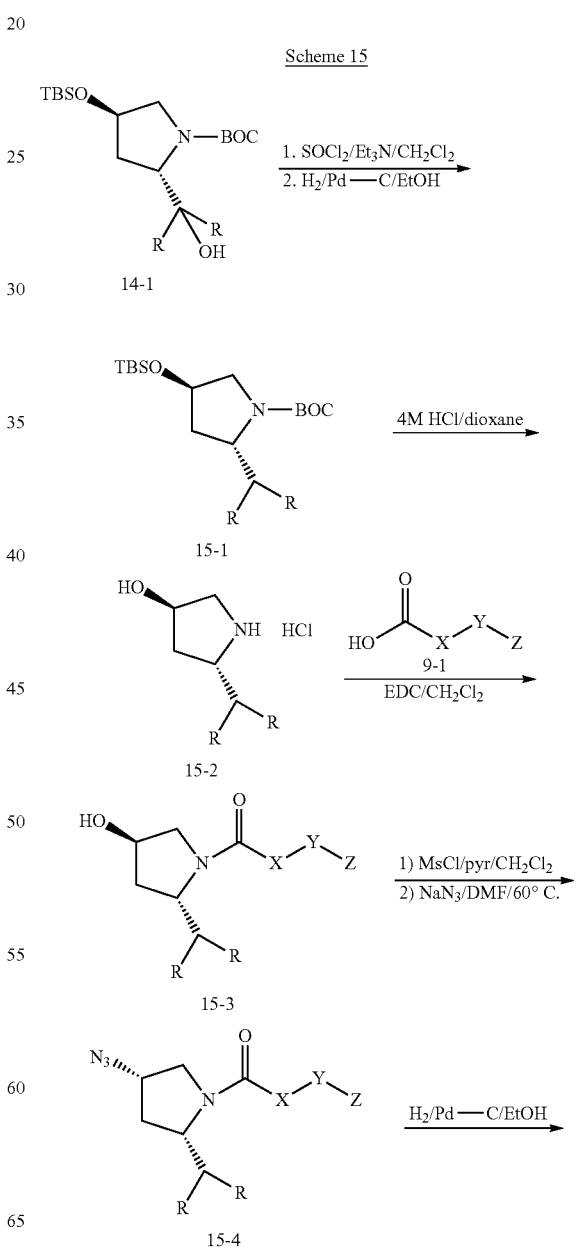

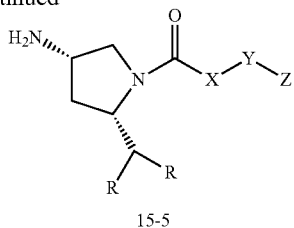

15-5

Compounds of formula I can be obtained by assembling the aminopyrrolidine derivatives of formula 16-1 with a ketone of formula 16-2 by reductive amination using a reducing agent such as sodium triacetoxyborohydride or through hydrogenation followed by treating the resulting secondary amine 16-3 via reductive amination with an aldehyde or by alkylation with an alkyl halide (RX).

Scheme 16

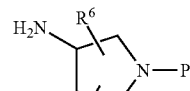

16-1

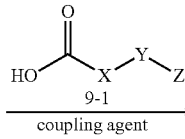

16-2
reducing agent

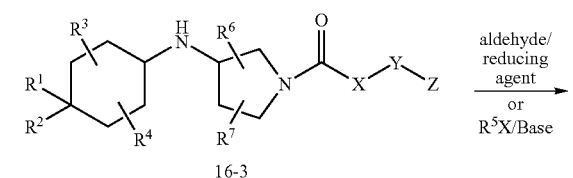

16-3 aldehyde/
reducing
agent
or
R⁵X/Base

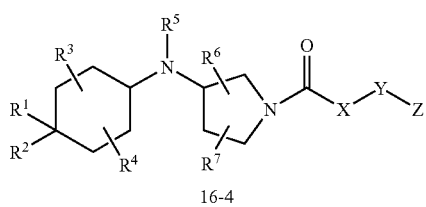

16-4

Alternatively, compounds of formula I can be prepared using a sequence outlined in Scheme 17. Reductive amination of the aminopyrrolidine derivatives of formula 17-1 with a ketone of formula 16-2 gives rise to the secondary amine 17-2. After removal of the protecting group P (P=Boc, benzyl or Cbz) using an acid or through hydrogenation using a catalyst such as Pd—C, the resulting amine 17-3 is condensed with a carboxylic acid of formula 9-1 to provide compounds of formula 17-4.

Scheme 17

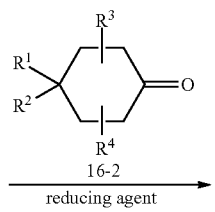

17-1

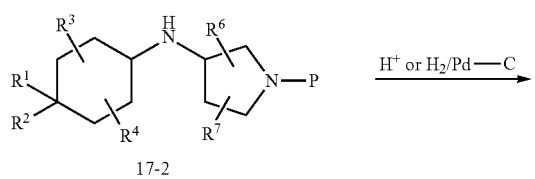

17-2

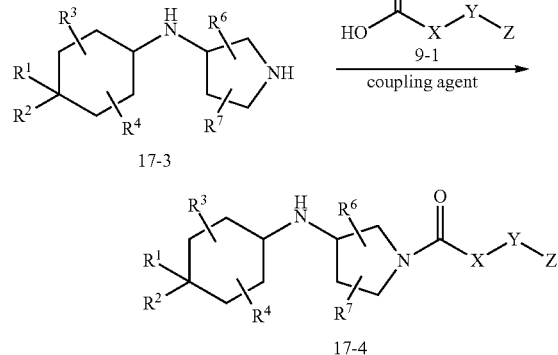

17-3

17-4

P = Boc, Bn, Cbz

Alternatively, compounds of formula I can be prepared using a sequence outlined in Scheme 18. Reduction of the cyclohexanone 1-2 with a reducing agent such as lithium aluminum hydride produces the cis diol 18-1. After converting the secondary alcohol to a mesylate, the resulting mesylate 18-2 is displaced with an aminopyrrolidine derivative of formula 17-1 to give the trans 4-amino-1-cyclohexanol derivative of formula 18-3. Removal of the protecting group using an acid or through hydrogenation followed by coupling of the resulting amine with a carboxylic acid of formula 9-1 affords compounds of formula 18-5.

Scheme 18

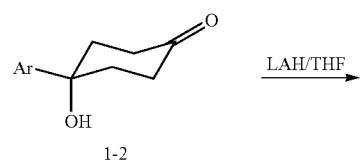

1-2

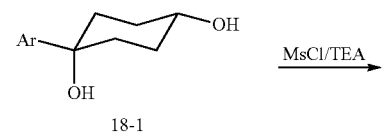

18-1

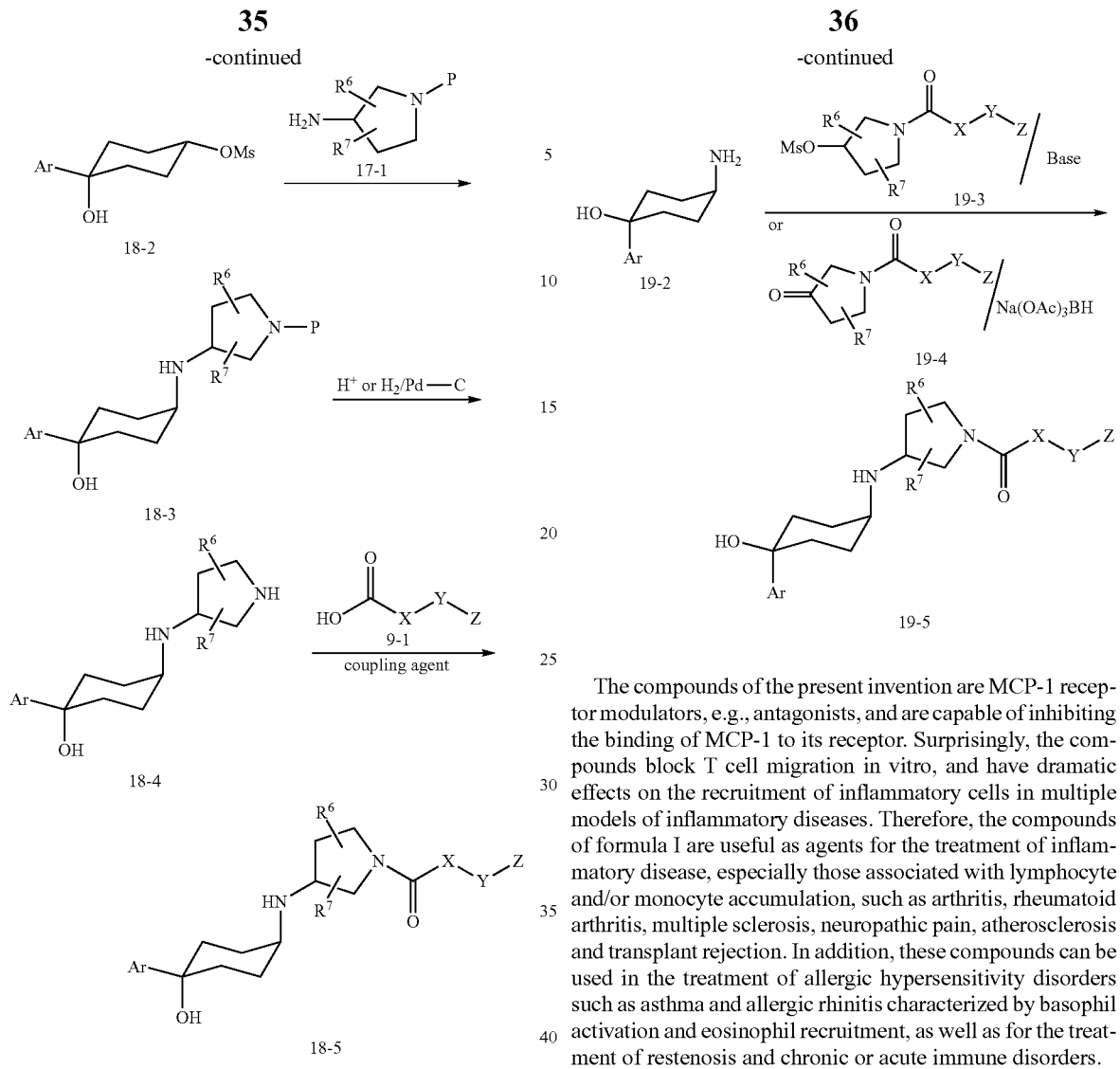

Alternatively, compounds of formula I can be synthesized according to Scheme 19. Displacement of the mesylate 18-2 with sodium azide gives rise to the azido intermediate 19-1 which is reduced to an amine by hydrogenation using a catalyst such as Pd—C. Displacement of the mesylate of formula 19-3 with the resulting amine 19-2 or reductive amination of 19-2 with a ketone of formula 19-4 affords compounds of formula 19-5.

Scheme 19

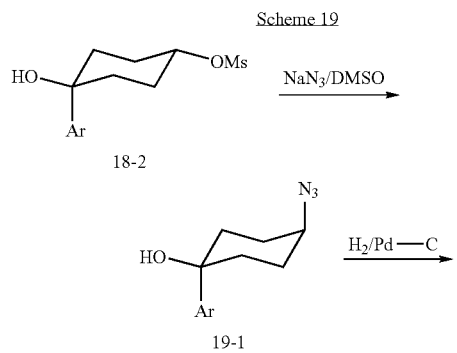

The compounds of the present invention are MCP-1 receptor modulators, e.g., antagonists, and are capable of inhibiting the binding of MCP-1 to its receptor. Surprisingly, the compounds block T cell migration in vitro, and have dramatic effects on the recruitment of inflammatory cells in multiple models of inflammatory diseases. Therefore, the compounds of formula I are useful as agents for the treatment of inflammatory disease, especially those associated with lymphocyte and/or monocyte accumulation, such as arthritis, rheumatoid arthritis, multiple sclerosis, neuropathic pain, atherosclerosis and transplant rejection. In addition, these compounds can be used in the treatment of allergic hypersensitivity disorders such as asthma and allergic rhinitis characterized by basophil activation and eosinophil recruitment, as well as for the treatment of restenosis and chronic or acute immune disorders.

Modulation of chemokine receptor activity, as used in the context of the present invention, is intended to encompass antagonism, agonism, partial antagonism and/or partial agonism of the activity associated with a particular chemokine receptor, preferably the CCR2 receptor. The term composition as used herein is intended to include a product comprising the specified ingredients in the specified amounts, as well as any product which results, directly or indirectly, from combination of the specified ingredients in the specified amounts. By pharmaceutically acceptable it is meant the carrier, diluent or excipient must be compatible with the other ingredients of the formulation and not deleterious to the recipient thereof.

The compounds of formula I of the present invention, and compositions thereof are useful in the modulation of chemokine receptor activity, particularly CCR2. Accordingly, the compounds of the present invention are those which inhibit at least one function or characteristic of a mammalian CCR2 protein, for example, a human CCR2 protein. The ability of a compound to inhibit such a function can be demonstrated in a binding assay (e.g., ligand binding or promotor binding), a signalling assay (e.g., activation of a mammalian G protein, induction of rapid and transient increase in the concentration of cytosolic free calcium), and/or cellular response function (e.g., stimulation of chemotaxis, exocytosis or inflammatory mediator release by leukocytes).

The invention is illustrated by the following examples, which are not intended to be limiting in any way.

EXAMPLES

Reagents and solvents used below can be obtained from commercial sources such as Aldrich Chemical Co. (Milwaukee, Wis., USA). Mass spectrometry results are reported as the ratio of mass over charge, followed by the relative abundance of each ion (in parentheses). In tables, a single m/e value is reported for the M+H (or, as noted, M−H) ion containing the most common atomic isotopes. Isotope patterns correspond to the expected formula in all cases.

Example 1

Step A

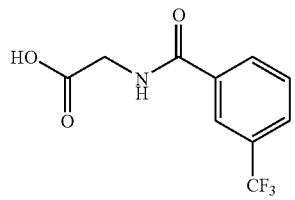 [SMILES: O=C(O)CNC(=O)c1cccc(C(F)(F)F)c1]

(3-Trifluoromethyl-benzoylamino)acetic acid

To a rapid stirring solution of glycine (15.014 g, 0.20 mol) in MeCN (400 mL) and 2 M NaOH (250 mL) at 0° C. was slowly added a solution of 3-(trifluoromethyl)-benzoyl chloride (41.714 g, 0.20 mol) in 75 mL of MeCN over 30 min. The cloudy yellow solution was stirred at 0° C. for 30 min. The reaction mixture was acidified with 3 M HCl to pH=3, followed by removal of MeCN on rotary evaporator. The resulting mixture was then extracted with EtOAc (400 mL×3). The combined organic layers were dried, filtered and concentrated to give a light yellow solid (48.53 g), which was triturated with toluene (500 mL). After filtration, the solid product was washed with cold toluene until the filtrate was colorless. After dried under high vacuum over the weekend, a white powder product: 44.60 g (90%) was afforded. MS (M+H$^+$)=248.1. $^1$H NMR (DMSO-d$_6$) δ 12.70 (br s, 1H), 9.17 (m, 1H), 8.20 (dd, 2H), 7.94 (dd, 1H), 7.78 (m, 1H), 3.97 (d, 2H).

Step B

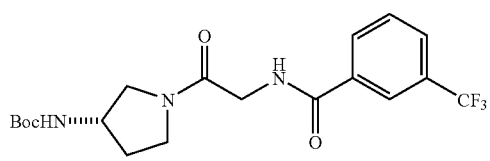 [SMILES: CC(C)(C)OC(=O)N[C@H]1CCN(C(=O)CNC(=O)c2cccc(C(F)(F)F)c2)C1]

tert-Butyl [(3S)-1-({[3-(Trifluoromethyl)benzoyl]amino}acetyl)pyrrolidin-3-yl]carbamate To a solution of the carboxylic acid (2.7 g, 11 mmol) from step A and tert-butyl (3S)-pyrrolidin-3-ylcarbamate (2.0 g, 11 mmol) in DMF (30 mL) cooled in an ice bath was added BOP (5 g, 11 mmol) followed by triethylamine (3 mL, 22 mmol). The mixture was allowed to warm to temperature and stirred overnight. Ethyl acetate (150 mL) was added. The resulting solution was washed with NaHCO$_3$ and brine each three times, dried over MgSO$_4$ and concentrated. Chromatography on silica gel eluting with EtOAc provided 4.4 g (96%) of the desired product. MS (M-Boc+H)$^+$ 316.

Step C

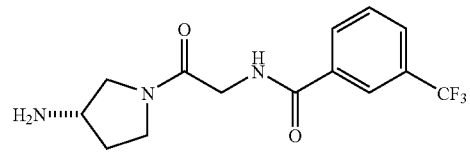 [SMILES: N[C@H]1CCN(C(=O)CNC(=O)c2cccc(C(F)(F)F)c2)C1]

N-{2-[(3S)-3-Aminopyrrolidin-1-yl]-2-oxoethyl}-3-(trifluoromethyl)benzamide

The above product (4.2 g) was dissolved in 4 N HCl/dioxane (30 mL). After being stirred for 1 hour at room temperature, the solution was concentrated to provide 4.0 g of the title compound. MS (M+H)$^+$ 316.

Step D

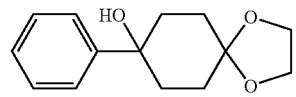 [SMILES: OC1(c2ccccc2)CCC2(CC1)OCCO2]

8-Phenyl-1,4-dioxaspiro[4.5]decan-8-ol

To a solution of 1,4-cyclohexanone mono-ethylene ketal (8.1 g, 50 mmol) in THF (20 mL) at 10° C. was added a 1 M solution of phenyl magnesium bromide in THF (70 mL, 70 mmol). The resulting mixture was stirred at room temperature for 2 hours before quenching with saturated NH$_4$Cl solution. The solution was extracted with EtOAc 3 times. The combined organic phase was washed with brine, dried over MgSO$_4$ and concentrated. Chromatography on silica gel eluting with 40% EtOAc/hexanes provided 9.5 g (81%) of the desired product. MS (M+H)$^+$ 234.

Step E

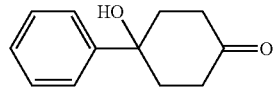

4-Hydroxy-4-phenylcyclohexanone

The above product was dissolved in THF (50 mL). To it was added 10% HCl/H$_2$O (50 mL). The solution was stirred at room temperature overnight and extracted with EtOAc three times. The combined extracts were washed with brine, dried over MgSO₄ and concentrated to give the title compound as a white solid. MS (M+H)⁺ 191.

Step F

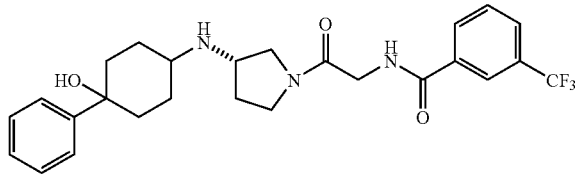 [SMILES: O=C(NCC(=O)N1CC[C@H](NC2CCC(O)(c3ccccc3)CC2)C1)c1cccc(C(F)(F)F)c1]

N-(2-{(3S)-3-[(4-Hydroxy-4-phenylcyclohexyl)amino]pyrrolidin-1-yl}-2-oxoethyl)-3-(trifluoromethyl)benzamide To a solution of the pyrrolidine intermediate from step C (0.3 g, 0.85 mmol) and the ketone from step E (0.16 g, 0.85 mmol) in THF (5 mL) was added Na(OAc)₃BH (0.35 g, 2.5 mmol) followed by triethylamine (0.2 mL, 1.5 mmol). The reaction was continued at room temperature overnight and quenched by addition of a saturated NaHCO₃ solution. The resulting solution was extracted with EtOAc and the EtOAc layer was dried over MgSO₄ and concentrated. Separation on silica gel eluting with 10% to 30% MeOH/EtOAc provided the cis (fast moving spot) and trans (slow moving spot) isomers of the title compound. MS (M+H)⁺ 490.0.

Example 2

Step A

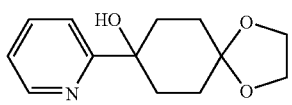

8-Pyridin-2-yl-1,4-dioxaspiro[4.5]decan-8-ol

To a solution of 2-bromopyridine (14 g, 88.6 mmol) in anhydrous ether (300 mL) cooled at −78° C. was slowly added a solution of 2.5 M n-butyl lithium (36 mL). After the addition, stirring was continued at −78° C. for 1 hour. To it was slowly added a solution of 1,4-cyclohexanedione monoethylene ketal (15 g, 96 mmol) in anhydrous ether (300 mL). When the addition was complete, the mixture was allowed to warm to 0° C. and stirring was continued for 1 hour. The reaction was quenched by the addition of an aqueous solution (100 mL) of ammonium chloride (4.5 g). The organic phase was separated and the aqueous phase was extracted with methylene chloride 4 times. The combined organic phases were dried over MgSO₄ and concentrated. Crystallization from EtOAc provided 7 g of the desired product. The mother liquid was purified on silica gel eluting with 10% MeOH/EtOAc to give 3 g of the desired product. MS (M+H)⁺ 236.0.

Step B

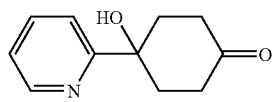

4-Hydroxy-4-(pyridin-2-yl)cyclohexanone

The above product was dissolved in THF (30 mL) and a 3 N solution of HCl in water (30 mL). The mixture was stirred at 50° C. for 3 hours. After cooling to room temperature, NaHCO₃ was added to the solution with stirring until no bubbling occurred. The organic phase was separated and the aqueous layer was extracted with EtOAc three times. The combined organic phase was dried over MgSO₄ and concentrated. The residue was triturated with EtOAc to give 5.5 g of the title compound. MS (M+H)⁺ 192.

Step C

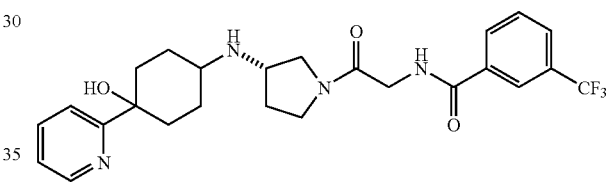

N-(2-{(3S)-3-[(4-Hydroxy-4-pyridin-2-ylcyclohexyl)amino]pyrrolidin-1-yl}-2-oxoethyl)-3-(trifluoromethyl)benzamide The title compound was prepared by reductive amination of the ketone obtained above with the pyrrolidine derivative obtained from step C in Example 1 using a procedure analogous to that described in step F, Example 1. MS (M+H)⁺ 491.

Example 3

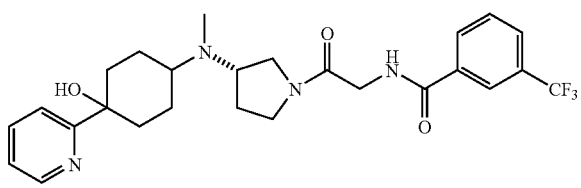

N-(2-{(3S)-3-[(4-Hydroxy-4-pyridin-2-ylcyclohexyl)(methyl)amino]pyrrolidin-1-yl}-2-oxoethyl)-3-(trifluoromethyl)benzamide To a solution of N-(2-{(3S)-3-[(4-hydroxy-4-pyridin-2-ylcyclohexyl)amino]pyrrolidin-1-yl}-2-oxoethyl)-3-(trifluoromethyl)benzamide (49 mg, 0.1 mmol) and formaldehyde (0.3 mL, 37% water solution) in THF (2 mL) was added Na(OAc)$_3$BH (64 mg, 0.3 mmol). After being stirred at room temperature overnight, the reaction was quenched by addition of a saturated NaHCO$_3$ solution. The resulting solution was extracted with EtOAc and the EtOAc layer was dried (MgSO$_4$) and concentrated. Purification by prep HPLC provided the title compound as a TFA salt. MS (M+H)$^+$ 505.

Example 4

Step A

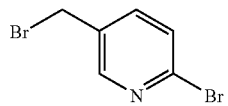

2-Bromo-5-bromomethylpyridine

2-Bromo-5-methylpyridine (5.00 g, 29.1 mmoles) and N-bromosuccinimide (5.22 g, 29.3 mmoles) were dissolved in carbon tetrachloride (40 mL) under nitrogen. Benzoyl peroxide (0.35 g, 1.4 mmoles) was added and the mixture heated at reflux for four hours. The mixture was cooled to room temperature, filtered, and washed with NaHCO$_3$/H$_2$O. The mixture was adsorbed onto silica gel and then chromatographed. eluting with a gradient of hexane to 10% ethyl acetate/hexane. Pure fractions were combined and concentrated to provide the desired mono-brominated product as a pale yellow solid, 3.60 g (49%). LC/MS (M+H)$^+$ m/z=249.8, 251.8, 253.8.

Step B

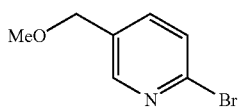

2-Bromo-5-(methoxymethyl)pyridine

2-Bromo-5-bromomethyl-pyridine, 4 (3.58 g, 14.3 mmoles) was dissolved in methanol (20 mL) under nitrogen. Sodium methoxide (0.89 g, 15.7 mmoles, 95%) was added and the mixture stirred at room temperature. After 3 hours, the methanol was rotovapped off and the residue dissolved in dichloromethane and washed with water. The organic extract was adsorbed onto silica gel and chromatographed. The column was eluted with a gradient of hexane to 20% ethyl acetate/hexane. Pure fractions were combined and concentrated to provide the title compound as a colorless oil, 2.62 g (90%). LC/MS (M+H)$^+$ m/z=202.0.

Step C

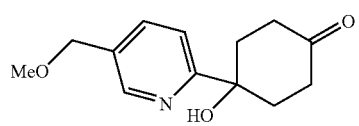

4-Hydroxy-4-[5-(methoxymethyl)pyridin-2-yl]cyclohexanone

A solution of 2-bromo-5-(methoxymethyl)pyridine (2.61 g, 12.9 mmoles) was dissolved in dry THF (40 mL) under nitrogen and cooled to −78° C. n-Butyllithium (6.20 mL, 15.5 mmoles, 2.5 M in hexane) was added dropwise over 10 minutes to form a black solution. After 15 minutes, a solution of 1,4-dioxa-spiro[4.5]decan-8-one (2.21 g, 14.1 mmoles) in THF was added dropwise over 2 minutes and the mixture was gradually warmed to room temperature over 3 hours. TLC (50% ethyl acetate/hexane) and LC/MS indicated complete conversion. Aqueous HCl (14 mL, 6.0 M) was added and the mixture was stirred for 3 hours at room temperature and then neutralized with NaHCO$_3$/H$_2$O. The mixture was extracted 3 times with ethyl acetate and the combined extracts were adsorbed onto silica gel and chromatographed. The column was eluted with a gradient of hexane to 40% ethyl acetate/hexane. Pure fractions were combined and concentrated to provide the title compound as a pale yellow solid, 1.00 g (33%). LC/MS (M+H)$^+$ m/z=236.1.

Step D

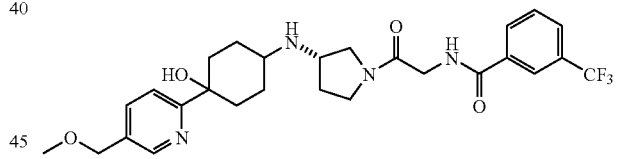

N-{2-[(3S)-3-({4-Hydroxy-4-[5-(methoxymethyl)pyridin-2-yl]cyclohexyl}amino)pyrrolidin-1-yl]-2-oxoethyl}-3-(trifluoromethyl)benzamide The title compound was prepared from the ketone of step C using a procedure analogous to that described for Example 1. MS (M+H)$^+$ 535.

Example 5

Step A

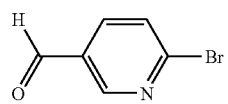

6-Bromo-pyridine-3-carbaldehyde 2,5-Dibromopyridine 9.48 g (40 mmol) was dissolved in 60 mL of THF and 150 mL of anhydrous ether. After the solution was cooled to −78° C., 16 mL of n-butyllithium (2.5 M, 40 mmol) was slowly dropped through a syringe in 30 min. After being stirred at −78° C. for 30 minutes, N,N-dimethylformamide (3.5 g, 48 mmol) was added. The reaction mixture was warmed up to room temperature during two hours and then quenched by addition of 10 ml water. The mixture was extracted twice using EtOAc. The combined extracts were dried and concentrated. After flash column using 30-40% EtOAc in hexane, 2.80 g white solid was obtained (28% yield), MS: (M+H)$^+$ 186.0, 188.0.

Step B

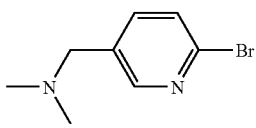

1-(6-Bromopyridin-3-yl)-N,N-dimethylmethanamine

To a solution of titanium tetraisopropoxide (6.4 g, 22 mmol) and 2.0 M of dimethylamine in methanol (22 mL, 44 mmol), 6-bromo-pyridine-3-carbaldehyde (2.10 g, 11 mmol) in 20 mL of methanol was added. After being stirred at r.t. for 5 hrs, sodium borohydride (0.43 g, 11 mmol) was added and the mixture was stirred overnight. The reaction was quenched by addition of 10 mL of water and extracted twice using EtOAc. The combined extracts were dried and concentrated.

After flash column using 20-40% methanol in EtOAc and 0.5% NH$_4$OH, 1.15 g oil was obtained (47% yield), MS: (M+H)$^+$ 214.0, 216.0.

Step C

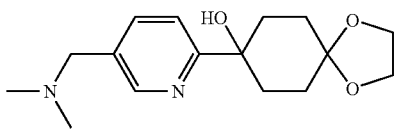 [SMILES: CN(C)Cc1ccc(C2(O)CCC3(CC2)OCCO3)nc1]

8-{5-[(Dimethylamino)methyl]pyridin-2-yl}-1,4-dioxaspiro[4,5]decan-8-ol 1-(6-Bromopyridin-3-yl)-N,N-dimethylmethanamine (1.15 g, 5.4 mmol) was dissolved in 30 mL of THF and 80 mL of anhydrous ether. After the solution was cooled to −78° C., 2.60 mL of n-butyllithium (2.5 M, 6.40 mmol) was slowly dropped through a syringe in 10 min. After being stirred at −78° C. for 30 minutes, 1,4-cyclohexanedione mono-ethylene ketal (1.01 g, 6.4 mmol) was added. The reaction mixture was allowed to warm up to room temperature during two hours and then quenched by addition of 10 mL of water. The mixture was extracted twice using EtOAc. The combined extracts were dried and concentrated. After flash column using 20-40% methanol in EtOAc and 0.5% NH$_4$OH, 0.85 g oil was obtained (54% yield), MS: (M+H)$^+$ 293.2.0.

Step D

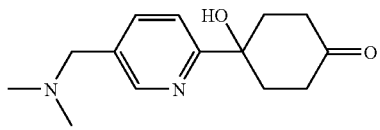 [SMILES: CN(C)Cc1ccc(C2(O)CCC(=O)CC2)nc1]

4-{5-[(Dimethylamino)methyl]pyridin-2-yl}-4-hydroxycyclohexanone

8-{5-[(Dimethylamino)methyl]pyridin-2-yl}-1,4-dioxaspiro[4,5]decan-8-ol (0.85 g, 2.9 mmol) was dissolved in 10 mL of THF and 10 mL of 2 N HCl solution was added. After being stirred for two hours, the reaction mixture was neutralized to pH~8-9 by addition of a saturated NaHCO$_3$ aqueous solution and extracted twice using EtOAc. The combined extracts were dried and concentrated to obtain 0.37 g white solid (51% yield), MS: (M+H)$^+$ 249.2.

Step E

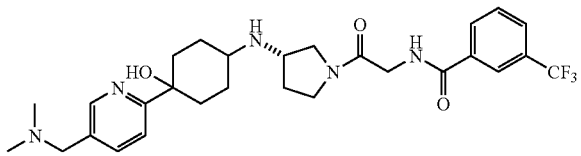

N-(2-{(3S)-3-[(4-{5-[(Dimethylamino)methyl]pyridin-2-yl}-4-hydroxycyclohexyl)amino]pyrrolidin-1-yl}-2-oxoethyl)-3-(trifluoromethyl)benzamide The title compound was prepared from the above ketone following the procedure described for Example 1. MS (M+H)$^+$ 548.

The following Examples 6-13 were prepared in a fashion similar to the previous 5 examples.

Example 6

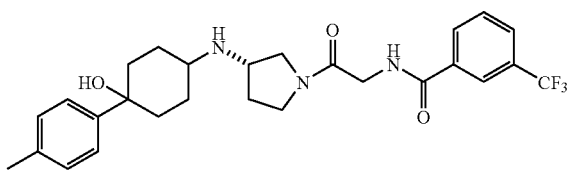

45

N-[2-((3S)-3-{[4-Hydroxy-4-(4-methylphenyl)cyclo-hexyl]amino}pyrrolidin-1-yl)-2-oxoethyl]-3-(trifluoromethyl)benzamide

MS (M+H)+ 504.

Example 7

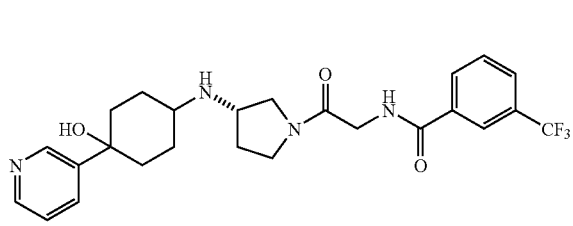

N-(2-{(3S)-3-[(4-Hydroxy-4-pyridin-3-ylcyclohexyl)amino]pyrrolidin-1-yl}-2-oxoethyl)-3-(trifluoromethyl)benzamide

MS (M+H)+ 491.

Example 8

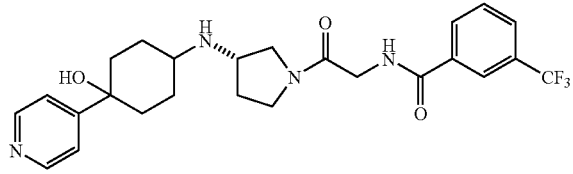

N-(2-{(3S)-3-[(4-Hydroxy-4-pyridin-4-ylcyclohexyl)amino]pyrrolidin-1-yl}-2-oxoethyl)-3-(trifluoromethyl)benzamide

MS (M+H)+ 491.

Example 9

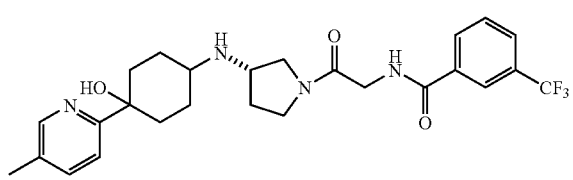

46

N-[2-((3S)-3-{[4-Hydroxy-4-(5-methylpyridin-2-yl)cyclohexyl]amino}pyrrolidin-1-yl)-2-oxoethyl]-3-(trifluoromethyl)benzamide

MS (M+H)+ 505.

Example 10

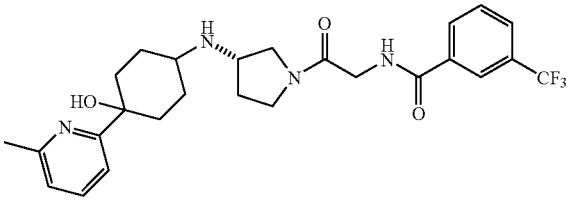 [SMILES: Cc1cccc(C2(O)CCC(N[C@H]3CCN(C(=O)CNC(=O)c4cccc(C(F)(F)F)c4)C3)CC2)n1]

N-[2-((3S)-3-{[4-Hydroxy-4-(4-methylpyridin-2-yl)cyclohexyl]amino}pyrrolidin-1-yl)-2-oxoethyl]-3-(trifluoromethyl)benzamide

MS (M+H)+ 505.

Example 11

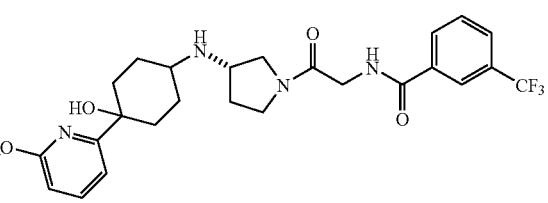

N-[2-((3S)-3-{[4-Hydroxy-4-(6-methylpyridin-2-yl)cyclohexyl]amino}pyrrolidin-1-yl)-2-oxoethyl]-3-(trifluoromethyl)benzamide

MS (M+H)+ 505.

Example 12

N-[2-((3S)-3-{[4-Hydroxy-4-(6-methoxypyridin-2-yl)cyclohexyl]amino}pyrrolidin-1-yl)-2-oxoethyl]-3-(trifluoromethyl)benzamide

MS (M+H)+ 521.

Example 13

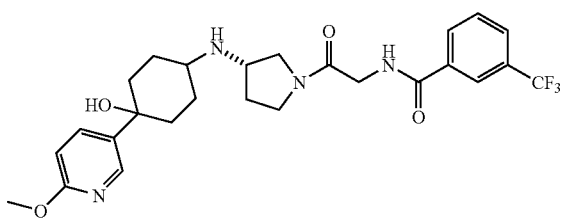 [SMILES: COc1ccc(C2(O)CCC(N[C@H]3CCN(C(=O)CNC(=O)c4cccc(C(F)(F)F)c4)C3)CC2)cn1]

N-[2-((3S)-3-{[4-Hydroxy-4-(6-methoxypyridin-3-yl)cyclohexyl]amino}pyrrolidin-1-yl)-2-oxoethyl]-3-(trifluoromethyl)benzamide

MS (M+H)+ 521.

Example 14

Step A

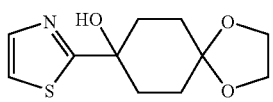

8-(1,3-Thiazol-2-yl)-1,4-dioxaspiro[4.5]decan-8-ol

A solution of n-butyllithium (8.1 mL of 1.6 M solution in hexane, 12.92 mmol) was added to thiazole (1.0 g, 11.75 mmol) in THF (10 mL) at −78° C. with stirring under N$_2$. After being stirred at −78° C. for 1 h, a solution of 1,4-cyclohexanedione mono-ethylene ketal (1.84 g, 11.75 mmol) in THF (10 mL) was added to the lithiated compound solution via syringe and stirred for 3 h at −78° C. Water (5 mL) was added, and the reaction mixture was warmed to room temperature and extracted using EtOAc (3×). The combined organic layers were dried (MgSO$_4$), filtered, concentrated in vacuo and chromatographed to yield 2.531 g of 8-(1,3-thiazol-2-yl)-1,4-dioxaspiro[4.5]decan-8-ol in 89% yield. MS (EI) (M+H)+=242.2.

Step B

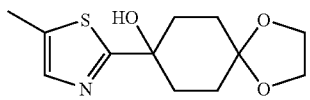

8-(5-Methyl-1,3-thiazol-2-yl)-1,4-dioxaspiro[4.5]decan-8-ol

A solution of n-butyllithium (5.70 mL of 1.6 M solution in hexane, 9.12 mmol) was added to 8-(1,3-thiazol-2-yl)-1,4-dioxaspiro[4.5]decan-8-ol (1.00 g, 4.14 mmol) in THF (10 mL) at −78° C. with stirring under N$_2$. After being stirred at −78° C. for 1 h, methyl iodide (0.71 mL, 9.12 mmol) was added to the lithiated compound solution via syringe at −78° C. The reaction mixture was allowed to warm to room temperature slowly and stirred overnight. Water and EtOAc were added. The aqueous layer was extracted with EtOAc (3×). The combined organic layers were washed with saturated NaCl, dried (MgSO$_4$), concentrated and flash chromatographed using 20% EtOAc/hexane to give 0.77 g of the title compound in 71% yield. MS (EI) (M+H)+=256.1.

Step C

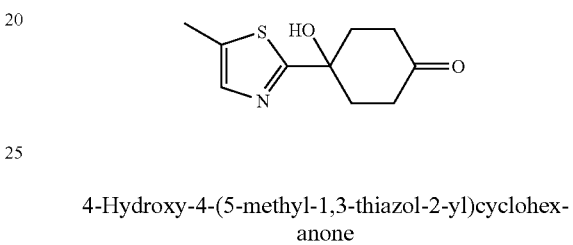

4-Hydroxy-4-(5-methyl-1,3-thiazol-2-yl)cyclohexanone

A solution of 8-(5-Methyl-1,3-thiazol-2-yl)-1,4-dioxaspiro[4.5]decan-8-ol (1.10 g, 4.14 mmol) in 20 mL of THF/3 N HCl (1:1) was stirred for 1 h at 50° C. After cooling to room temperature, the mixture was treated with Na$_2$CO$_3$ to pH 8 and extracted with EtOAc (3×). The combined organic layers were washed with saturated NaCl solution, dried (MgSO$_4$), and concentrated to give 0.82 g of 4-hydroxy-4-(5-methyl-1,3-thiazol-2-yl)cyclohexanone in 99% yield. MS (EI) (M+H)+= 212.2.

Step D

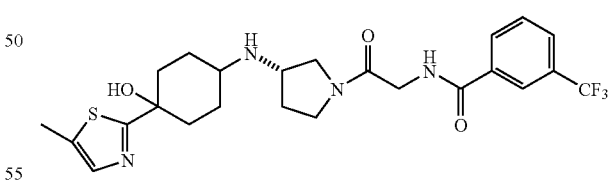

3-(Trifluoromethyl)-N-[2-((3S)-3-{[4-hydroxy-4-(5-methyl-1,3-thiazol-2-yl)cyclohexyl]amino}pyrrolidin-1-yl)-2-oxoethyl]benzamide The title compound was prepared from the ketone of step C using a procedure similar to that described for Example 1. MS (EI): (M+H)+ 511.1.

The following Examples 15-16 were prepared in a fashion similar to Example 14.

Example 15

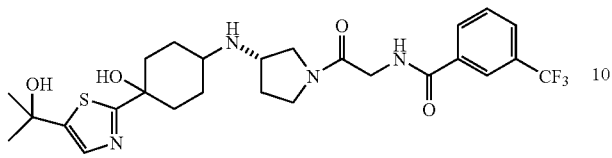

3-(Trifluoromethyl)-N-{2-[(3S)-3-({4-hydroxy-4-[5-(1-hydroxy-1-methylethyl)-1,3-thiazol-2-yl]cyclohexyl}amino)pyrrolidin-1-yl]-2-oxoethyl}benzamide

MS (EI): (M+H)$^+$ 555.2.

Example 16

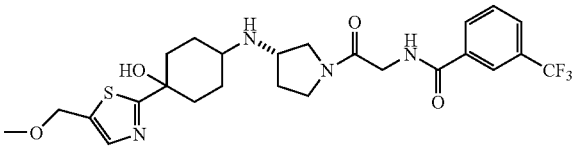 [SMILES: COCc1cnc(C2(O)CCC(N[C@H]3CCN(C(=O)CNC(=O)c4cccc(C(F)(F)F)c4)C3)CC2)s1]

3-(Trifluoromethyl)-N-{2-[(3S)-3-({4-hydroxy-4-[5-(methoxymethyl)-1,3-thiazol-2-yl]cyclohexyl}amino)pyrrolidin-1-yl]-2-oxoethyl}benzamide

MS (EI): (M+H)$^+$ 541.1.

Example 17

Step A

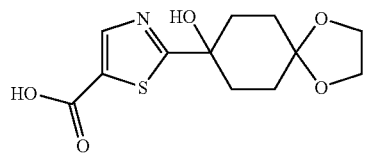 [SMILES: O=C(O)c1cnc(C2(O)CCC3(CC2)OCCO3)s1]

2-(8-Hydroxy-1,4-dioxaspiro[4.5]dec-8-yl)-1,3-thiazole-4-carboxylic acid

A solution of n-butyllithium (17.1 mL of 1.6 M solution in hexane, 27.35 mmol) was added to 8-(1,3-thiazol-2-yl)-1,4-dioxaspiro[4.5]decan-8-ol (3.00 g, 12.43 mmol) in THF (50 mL) at −78° C. with stirring under N$_2$. After being stirred at −78° C. for 1 h, dry ice (10 g, 227 mmol) was added to the lithiated compound solution and stirred for 2 h at −78° C. Water was added and the solution was warmed to room temperature. The mixture was then treated with 1N HCl to pH 3 to 4 and extracted with EtOAc (3×). The combined organic layers were washed with saturated NaCl solution, dried (MgSO$_4$), and concentrated and chromatographed (EtOAc to 1% AcOH/EtOAc) to give 3.23 g of 2-(8-hydroxy-1,4-dioxaspiro[4.5]dec-8-yl)-1,3-thiazole-4-carboxylic acid. MS (EI) (M+H)$^+$=286.0.

Step B

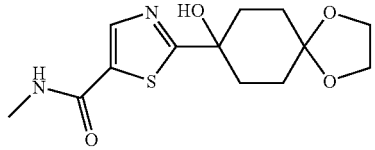 [SMILES: CNC(=O)c1cnc(C2(O)CCC3(CC2)OCCO3)s1]

2-(8-Hydroxy-1,4-dioxaspiro[4.5]dec-8-yl)-N-methyl-1,3-thiazole-4-carboxamide

To a stirred solution of 2-(8-hydroxy-1,4-dioxaspiro[4.5]dec-8-yl)-1,3-thiazole-4-carboxylic acid (0.30 g, 1.05 mmol) and methylamine (2M in THF, 2 mL, 4 mmol) in CH$_2$Cl$_2$ (10 mL) was added Et$_3$N (0.5 mL, 3.6 mmol) followed by EDC (0.242 g, 1.262 mmol) and HOBt (0.193 g, 1.26 mmol). The mixture was stirred at room temperature overnight. Then the reaction mixture was diluted with EtOAc and washed with saturated Na$_2$CO$_3$ and brine. The organic layer was dried (MgSO$_4$), concentrated and flash chromatographed (50% EtOAc/hexanes) to give 0.16 g of the title compound in 50% yield. MS (EI) (M+H)$^+$=299.0.

Step C

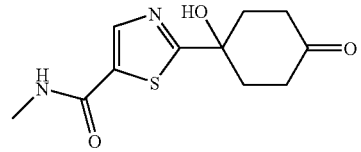 [SMILES: CNC(=O)c1cnc(C2(O)CCC(=O)CC2)s1]

2-(1-Hydroxy-4-oxocyclohexyl)-N-methyl-1,3-thiazole-4-carboxamide

The title compound was prepared by conversion of the ketal of step B to a ketone using a procedure similar to that described in step C of Example 14. MS (EI) (M+H)$^+$=255.0.

Step D

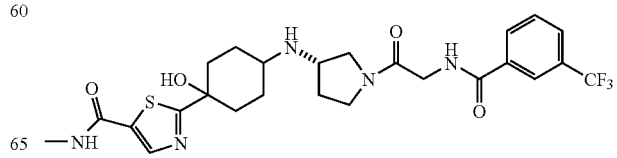

2-(1-Hydroxy-4-{[(3S)-1-({[3-(trifluoromethyl)benzoyl]amino}acetyl)pyrrolidin-3-yl]amino}cyclohexyl)-N-methyl-1,3-thiazole-5-carboxamide The title compound was prepared from the ketone of step C using the method described for Example 1. MS (EI): (M+H)+ 553.

The following Examples 18-19 were prepared in fashion similar to Example 17.

Example 18

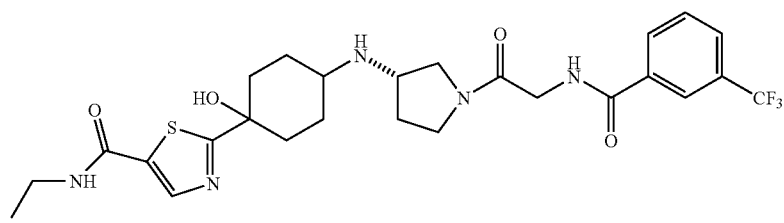 [SMILES: CCNC(=O)c1cnc(C2(O)CCC(N[C@H]3CCN(C(=O)CNC(=O)c4cccc(C(F)(F)F)c4)C3)CC2)s1]

N-Ethyl-2-(1-hydroxy-4-{[(3S)-1-({[3-(trifluoromethyl)benzoyl]amino}acetyl)pyrrolidin-3-yl]amino}cyclohexyl)-1,3-thiazole-5-carboxamide

MS (EI): (M+H)$^+$ 567.1.

Example 19

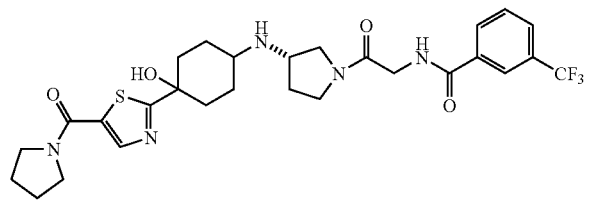

N-{2-[(3S)-3-({4-Hydroxy-4-[5-(pyrrolidin-1-ylcarbonyl)-1,3-thiazol-2-yl]cyclohexyl}-amino)pyrrolidin-1-yl]-2-oxoethyl}-3-(trifluoromethyl)benzamide

MS (EI): (M+H)$^+$ 594.1.

Example 20

Step A

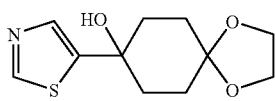 [SMILES: OC1(c2cncs2)CCC2(CC1)OCCO2]

8-(1,3-Thiazol-5-yl)-1,4-dioxaspiro[4,5]decan-8-ol

2-TMS-thiazole (2.5 g, 15.89 mmol) was added to a solution of n-butyllithium (11.9 mL of 1.6 M solution in hexane, 19.07 mmol) in THF (20 mL) at −78° C. with stirring under N$_2$. After being stirred at −78° C. for 0.5 h, a solution of 1,4-cyclohexanedione mono-ethylene ketal (2.48 g, 15.89 mmol) in THF (20 mL) was added to the lithiated compound solution via syringe and stirred for 1 h at −78° C. Water (5 mL) and EtOAc were added, and the reaction mixture was warmed to room temperature and extracted using EtOAc (3×). The combined organic layers were dried (MgSO$_4$), filtered, and crystallized from EtOAc to yield 3.4 g of 8-(1,3-thiazol-5-yl)-1,4-dioxaspiro[4,5]decan-8-ol in 90% yield. MS (EI) (M+H)$^+$=242.1.

Step B

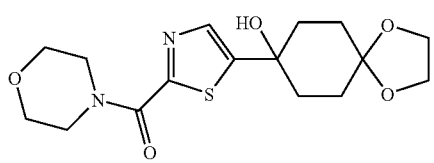 [SMILES: O=C(c1ncc(C2(O)CCC3(CC2)OCCO3)s1)N1CCOCC1]

4-Hydroxy-4-[2-(morpholin-4-ylcarbonyl)-1,3-thiazol-5-yl]cyclohexanone

A solution of n-butyllithium (2.90 mL of 1.6 M in hexane, 4.64 mmol) was added to 8-(1,3-thiazol-5yl)-1,4-dioxaspiro[4,5]decan-8-ol (1.00 g, 4.10 mmol) in THF (20 ml) at −78° C. under N$_2$. After being stirred at −78° C. for 1 h, 4-morpholinecarbonyl chloride (0.93 g, 6.15 mmol) was added to the lithiated compound solution via syringe and stirred for 2 h at −78° C. Water (5 mL) was added, and the reaction mixture was warmed to room temperature. The reaction mixture was diluted with water and EtOAc. The aqueous layer was extracted with EtOAc (3×). The combined organic layers were washed with brine, dried (Na$_2$SO$_4$), and concentrated to give the ketal intermediate. Then this intermediate was treated with 20 mL of THF/1N HCl (1:1) overnight at room temperature. The reaction solution was justified to pH 10 with Na$_2$CO$_3$ and extracted with EtOAc (3×). The combined organic layers were washed with brine, dried (Na$_2$SO$_4$), concentrated and flash chromatographed using 20% EtOAc/hexanes to yield 309 mg of the title compound. MS (EI) (M+H)$^+$= 311.0.

Step C

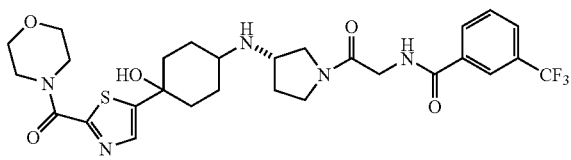

3-(Trifluoromethyl)-N-{2-[(3S)-3-({4-hydroxy-4-[2-(methoxymethyl)-1,3-thiazol-5-yl]cyclohexyl}amino)pyrrolidin-1-yl]-2-oxoethyl}benzamide The title compound was prepared from the ketone of step B using procedures similar to that for Example 14. MS (EI): (M+H)$^+$ 541.1.

The following Examples 21-23 were prepared in fashion similar to Example 20.

Example 21

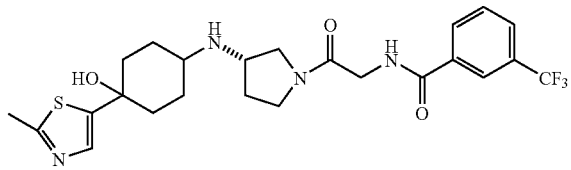

3-(Trifluoromethyl)-N-[2-((3S)-3-{[4-hydroxy-4-(2-methyl-1,3-thiazol-5-yl)cyclohexyl]amino}pyrrolidin-1-yl)-2-oxoethyl]benzamide

MS (EI): (M+H)$^+$ 511.1.

Example 22

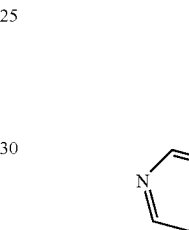

3-(Trifluoromethyl)-N-[2-((3S)-3-{[4-(2-ethyl-1,3-thiazol-5-yl)-4-hydroxycyclohexyl]amino}pyrrolidin-1-yl)-2-oxoethyl]benzamide

MS (EI): (M+H)$^+$ 525.2.

Example 23

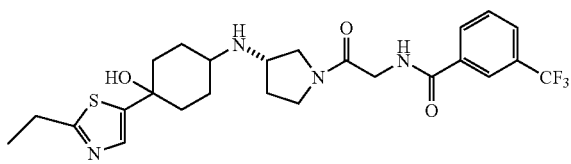

N-[2-((3S)-3-{[4-Hydroxy-4-(2-isopropyl-1,3-thiazol-5-yl)cyclohexyl]amino}pyrrolidin-1-yl)-2-oxoethyl]-3-(trifluoromethyl)benzamide

MS (EI): (M+H)$^+$ 539.2.

Example 24

Step A 8-(5-Pyridin-3-yl-1,3-thiazol-2-yl)-1,4-dioxaspiro[4.5]decan-8-ol

A solution of n-butyllithium (7.8 mL of 1.6 M solution in hexane, 12.45 mmol) was added to 8-(1,3-thiazol-5-yl)-1,4-dioxaspiro[4,5]decan-8-ol (1.0 g, 4.15 mmol) in THF (20 mL) at −78° C. with stirring under N$_2$. After being stirred at −78° C. for 0.5 h, 12.5 mL of 0.5 M solution of ZnCl$_2$ (6.23 mmol) in THF was added. The resulting mixture was stirred at room temperature for 0.5 h and a mixture of 3-bromopyridine (0.40 mL, 4.15 mmol) and PdCl$_2$(PPh$_3$)$_2$ (0.11 g, 0.16 mmol) in 5 mL of THF was added via syringe. After refluxing overnight the reaction was quenched with 10 mL of saturated NH$_4$Cl solution. The aqueous layer was extracted using EtOAc (3×). The combined organic layers were dried (MgSO$_4$), filtered, concentrated in vacuo and chromatographed to yield 0.68 g of the title compound in 52% yield. MS (EI) calcd: (M+H)$^+$=319.1; found: 319.1.

Step B

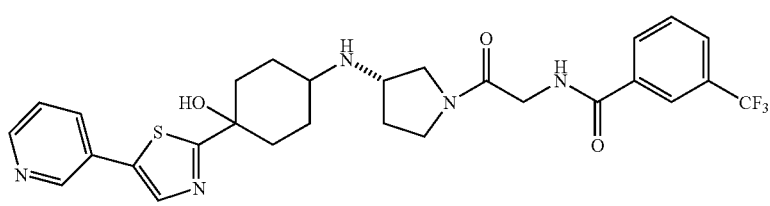

N-[2-(3S)-(3-{[4-Hydroxy-4-(5-pyridin-3-yl-1,3-thiazol-2-yl)cyclohexyl]methyl}-pyrrolidin-1-yl)-2-oxoethyl]-3-(trifluoromethyl)benzamide The title compound was prepared from the ketal of step A following the procedures described for Example 14. MS (EI): (M+H)+ 574.2.

Example 25

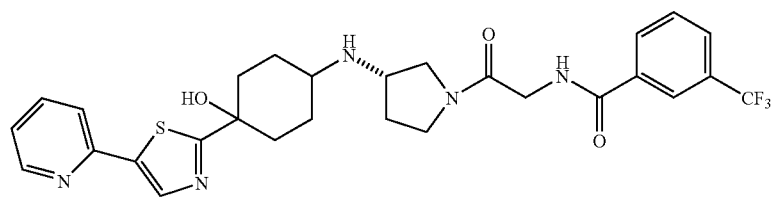

N-[2-({(3S)-1-[4-Hydroxy-4-(5-pyridin-2-yl-1,3-thiazol-2-yl)cyclohexyl]pyrrolidin-3-yl}amino)-2-oxoethyl]-3-(trifluoromethyl)benzamide The title compound was prepared following the procedures described for Example 24. MS (EI): (M+H)+ 574.2.

Example 26

Step A

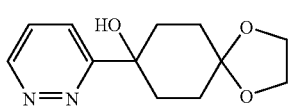

8-Pyridazin-3-yl-1,4-dioxaspiro[4.5]decan-8-ol

To a solution of pyridazine (17.7 mmol, 1.28 mL) in THF (60 mL) was added lithium 2,2,6,6-tetramethylpiperidine (71 mmol, 10 g) at −78° C. The reaction was then stirred for 6 min and 1,4-dioxa-spiro[4.5]decan-8-one (71 mmol, 11 g) was added. The reaction was stirred for 5 h at −78° C. at which point the reaction was quenched using a solution of ethanol, hydrochloric acid and THF (30 mL, 1:1:1). The resulting solution was extracted using EtOAc. The organic layers were combined, dried over MgSO4 and concentrated. The residue was purified using flash chromatography to afford the desired alcohol (44%, 1.84 g). MS (M+H)+ 237.1.

Step B

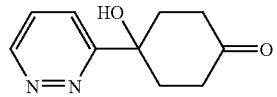

4-Hydroxy-4-pyridazin-3-ylcyclohexanone

To the product from step A (7.79 mmol, 1.84 g) in THF (15 mL) was added HCl (45 mmol, 15 mL). The reaction was stirred overnight and subsequently quenched using Na2CO3. The solution was then extracted using EtOAc (3×100 mL). The organic layers were combined, dried and concentrated in vacuo to afford the desired ketone (780 mg, 52%). MS (M+H)+ 193.1.

Step C

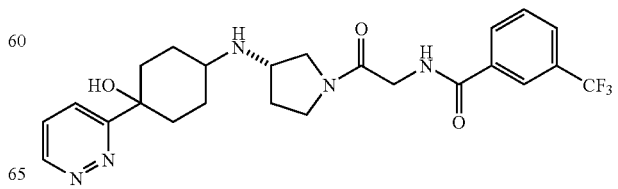

N-(2-{(3S)-3-[(4-Hydroxy-4-pyridazin-3-ylcyclohexyl)amino]pyrrolidin-1-yl}-2-oxoethyl)-3-(trifluoromethyl)benzamide The title compound was prepared from the ketone of step B using a procedure similar to that described for Example 1. MS (M+H)+ 492.2.

Example 27

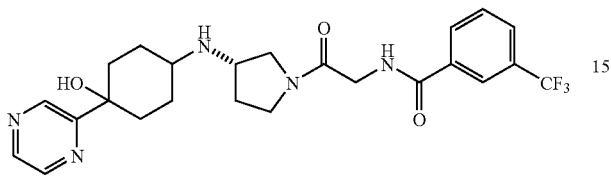

N-(2-{(3S)-3-[(4-hydroxy-4-pyrazin-2-ylcyclohexyl)amino]pyrrolidin-1-yl}-2-oxoethyl)-3-(trifluoromethyl)benzamide The title compound was prepared in a manner similar to that for Example 26. MS (M+H)+ 492.2.

Example 28

Step A

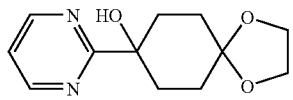

8-Pyrimidin-2-yl-1,4-dioxa-spiro[4.5]decan-8-ol (1a)

To a solution of 2-bromopyrimidine (0.20 g, 1.258 mmol) in dry methylene chloride (3.0 mL) was dropwise added 1.6 M of n-butyllithium in hexane (0.86 mL) at −78° C. The reaction mixture was stirred for 29 min at −78° C. and 1,4-dioxa-spiro[4.5]decan-8-one (0.196 g, 1.26 mmol) in $CH_2Cl_2$ (3 mL) was added dropwise. The reaction was stirred at −78° C. for 50 min and quenched with an aqueous solution of $NH_4Cl$. After being warmed to room temperature, the mixture was extracted with $CH_2Cl_2$ three times. The combined extracts were dried over $MgSO_4$, filtered and concentrated in vacuo to provide 0.50 g of crude product. Purification by column chromatography on silica gel eluting with 0→50% EtOAc in hexanes provided 0.159 g (54%) of desired product as a light brown-yellow solid. MS (M+H)+ 237.2.

Step B

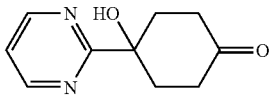

4-Hydroxy-4-pyrimidin-2-ylcyclohexanone

To the product from step A (190 mmol, 44 g) in THF (200 mL) was added HCl solution (300 mmol, 100 mL). The reaction was stirred over 2 days after which the reaction was washed using diethyl ether. The aqueous layer was then quenched using NaOH (50%) to obtain a pH of 11. The aqueous layer was extracted using EtOAc (6×300 mL). The organic layers were combined and dried over $MgSO_4$ and concentrated in vacuo. The reaction was purified via flash chromatography to afford the desired ketone (18 g, 49%). MS (M+H)+ 193.1.

Step C

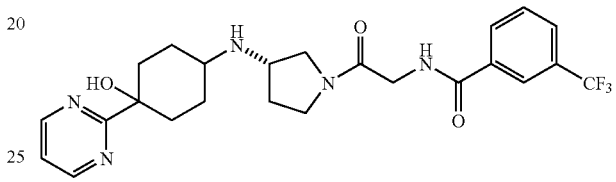

N-(2-{(3S)-3-[(4-Hydroxy-4-pyrimidin-2-ylcyclohexyl)amino]pyrrolidin-1-yl}-2-oxoethyl)-3-(trifluoromethyl)benzamide The title compound was prepared from the ketone of step B using a procedure similar to that for Example 1. MS (M+H)+ 492.2.

Example 29

Step A

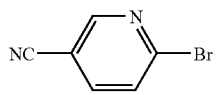

6-Bromonicotinonitrile

6-Chloronicotinonitrile (13.8 g, 100 mmol) was heated at 145° C. in phosphorus tribromide (150 mL) for 32 h. After cooling, the mixture was concentrated in vacuo. To the residue was added phosphorus tribromide (150 mL), and the mixture was heated at 145° C. for another 32 h. After cooling, the mixture was concentrated in vacuo, and an ice-water mixture (500 mL) was added. Sodium bicarbonate was added to neutralize the mixture, and the product was extracted with ethyl acetate (3×250 mL). The combined organic extracts were washed with brine and dried over magnesium sulfate. The solvent was removed in vacuo, and the residue was chromatographed (hexanes-ethyl acetate) to give 14.9 g (81%) of 6-bromonicotinonitrile as a white solid: $^1$H NMR (400 MHz, CDCl$_3$) δ7.66 (d, J=11.0 Hz, 1H), 7.80 (dd, J=3.1, 11.0 Hz, 1H), 8.67 (d, J=3.1 Hz, 1H); MS (M+H)$^+$ m/z=183.0, 185.0.

Step B

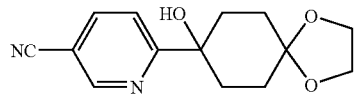

6-(8-hydroxy-1,4-dioxaspiro[4.5]dec-8-yl)nicotinonitrile

A solution of 6-bromonicotinonitrile (2 g, 11 mmol) in 50 mL of dry THF and 15 mL of dry hexane under argon was cooled to −100° C. in a liquid nitrogen-Et$_2$O bath. n-Butyllithium (7.5 mL, 11 mmol, 1.6 M solution in hexane) was added dropwise so that the internal temperature did not exceed −95° C. The orange solution was stirred for an additional 10 min at −100° C. to −95° C. and then treated dropwise over 10 min with a solution of 1,4-cyclohexanedione monoethylene ketal (1.8 g, 11 mmol) in 55 mL of dry THF, again carefully maintaining the temperature below −95° C. The reaction mixture was stirred for 10 min at −100° C. to −95° C., allowed to warm to 20° C. and poured into ice water (400 mL). The organic layer was separated, and the aqueous layer was extracted twice with Et$_2$O (200 mL). The combined organic extracts were dried over MgSO$_4$ and evaporated to give 2.8 g of white crystalline solid. Trituration with Et$_2$O afforded 1.9 g (67% yield) of white crystals: MS: (M+H)$^+$ 261.

Step C

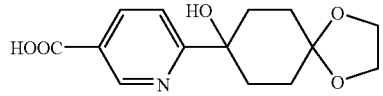

6-(8-hydroxy-1,4-dioxaspiro[4.5]dec-8-yl)nicotinic acid

A mixture of 6-(8-hydroxy-1,4-dioxaspiro[4.5]dec-8-yl)nicotinonitrile (1.9 g, 7.3 mmol) in 50 mL of 2-methoxyethanol and 50 mL of 2.5 N NaOH was heated on a steam bath for 15 h. The solution was cooled in an ice bath, adjusted to pH 7-8 with concentrated HCl, and evaporated to driness. Water (375 mL) was added, and the pH was adjusted to 2 with HCl. The tan solid was filtered off and washed with water to give 1.92 g (6.9 mmol, 94% yield) of 6-(8-hydroxy-1,4-dioxaspiro[4.5]dec-8-yl)nicotinic acid: MS: (M+H)$^+$ 280.

Step D

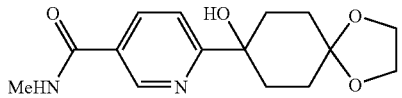

6-(8-Hydroxy-1,4-dioxaspiro[4.5]dec-8-yl)-N-methylnicotinamide 6-(8-Hydroxy-1,4-dioxaspiro[4.5]dec-8-yl)nicotinic acid (560 mg, 2 mmol), methylamine (1.2 mL, 2.0 M THF solution), BOP reagent (1.07 g, 2.4 mmol) and 0.8 mL (6 mmol) of triethylamine were dissolved in 15 mL of DMF at room temperature. The reaction mixture was stirred at room temperature overnight. Direct chromatography on silica gel (flash chromatography grade) with 50% ethyl acetate-hexane gave 410 mg (70%) of the desired product, 6-(8-hydroxy-1,4-dioxaspiro[4.5]dec-8-yl)-N-methylnicotinamide: MS: (M+H)$^+$ 293.

Step E

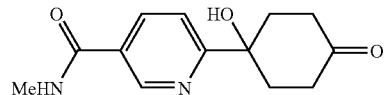

6-(1-Hydroxy-4-oxocyclohexyl)-N-methylnicotinamide 6-(8-Hydroxy-1,4-dioxaspiro[4.5]dec-8-yl)-N-methylnicotinamide (410 mg, 1.4 mmol) was dissolved in the mixture solvent of 7 mL of THF and 7 mL of 1 N HCl aqueous solution at room temperature. The reaction mixture was then stirred at 60° C. for 1 h. The solution was cooled down to room temperature, adjusted to pH 7-8 with saturated NaHCO$_3$ aqueous solution. The organic layer was separated, and the aqueous layer was extracted twice with EA (20 ml×2). The combined organic extracts were dried over MgSO$_4$ and evaporated to give an oil residue. Chromatography on silica gel (flash chromatography grade) with 40% ethyl acetate-hexane gave 410 mg (90%) of the desired product, 6-(1-hydroxy-4-oxocyclohexyl)-N-methylnicotinamide: MS: (M+H)$^+$ 249.

Step F

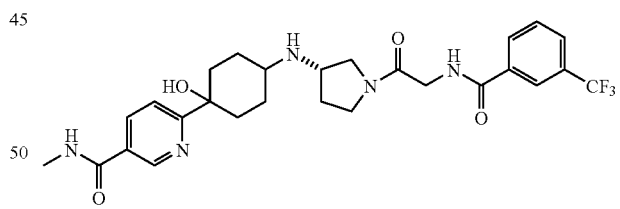

6-(1-Hydroxy-4-{[(3S)-1-({[3-(trifluoromethyl)benzoyl]amino}acetyl)pyrrolidin-3-yl]amino}cyclohexyl)-N-methylnicotinamide 6-(1-Hydroxy-4-oxocyclohexyl)-N-methylnicotinamide (100 mg, 0.4 mmol) and 126 mg (0.4 mmol) of N-{2-[(3S)-3-aminopyrrolidin-1-yl]-2-oxoethyl}-3-(trifluoromethyl)benzamide were dissolved in 10.0 mL of methylene chloride. To the solution was added 170 mg (0.8 mmol) of sodium triacetoxyborohydride. The reaction mixture was stirred at room temperature for 2 h. Direct chromatography on silica gel gave 48 mg (23%) of the final desired product (top spot on TLC and first peak on HPLC). MS: (M+H)$^+$ 547.

The following Examples 30-31 were prepared in fashion similar to Example 29.

Example 30

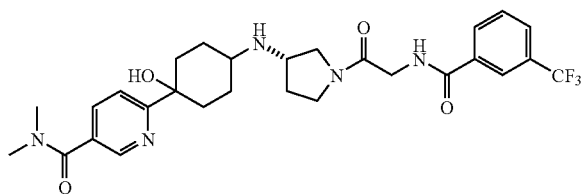

6-(1-Hydroxy-4-{[(3S)-1-({[3-(trifluoromethyl)benzoyl]amino}acetyl)pyrrolidin-3-yl]amino}cyclohexyl)-N,N-dimethylnicotinamide

MS (M+H)⁺ 562.

Example 31

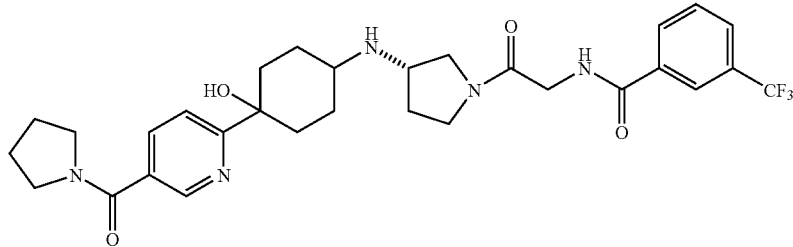

N-{2-[(3S)-3-({4-Hydroxy-4-[5-(pyrrolidin-1-ylcarbonyl)pyridin-2-yl]cyclohexyl}-amino)pyrrolidin-1-yl]-2-oxoethyl}-3-(trifluoromethyl)benzamide

MS (M+H)⁺ 588.

Example 32

Step A

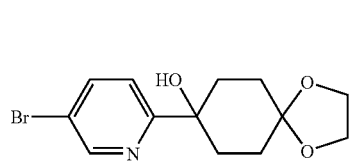

8-(5-Bromopyridin-2-yl)-1,4-dioxaspiro[4.5]decan-8-ol

To a solution of 2,5-dibromopyridine (4.10 g, 17 mmol) in anhydrous toluene (250 mL) at −78° C. was dropwise added n-BuLi (1.6 M, 12 mL). After stirred at −78° C. for 2.5 hours, a solution of 1,4-dioxa-spiro[4.5]decan-8-one (2.73 g, 17 mmol) in methylene chloride (25 mL) was added into the reaction mixture, and the resulting mixture was stirred for additional one hour and allowed to warm up to room temperature slowly. The reaction mixture was poured into aqueous NaHCO₃ (200 mL) and then extracted with EtOAc (2×50 mL). The organic extracts were combined, washed with saline solution (2×50 mL), dried over MgSO₄, and concentrated in vacuo. The resulting solid was triturated with ether and the solid was collected by filtration. The ether solution was concentrated and the solid was chromatographed on silica gel, eluting with hexane/ethyl acetate (2 to 1) to give a pale yellow solid. Weight of combined solids: 4.26 g. LCMS: 316.10/314.10 (M+H⁺, 100%). ¹HNMR: δ 8.6 (s, 1H), 7.82 (d, 1H), 7.38 (d, 1H), 4.6 (s, 1H), 4.0 (m, 4H), 2.2 (m, 4H), 1.7 (m, 4H).

Step B

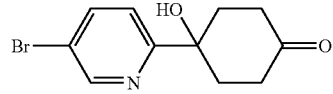

4-(5-Bromopyridin-2-yl)-4-hydroxycyclohexanone

The title compound was prepared by treating the ketal of step A with HCl in water following the procedure described in step B of Example 2. MS (M+H)⁺ 271.

Step C

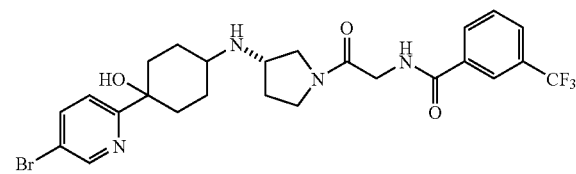

N-[2-((3S)-3-[4-(5-bromopyridin-2-yl)-4-hydroxycyclohexyl]aminopyrrolidin-1-yl)-2-oxoethyl]-3-(trifluoromethyl)benzamide To a 1-neck round-bottom flask charged with isopropanol (6 mL) was added 4-(5-bromopyridin-2-yl)-4-hydroxycyclohexanone (497.6 mg, 1.85 mmol), N-2-[(3S)-3-aminopyrrolidin-1-yl]-2-oxoethyl-3-(trifluoromethyl)-benzamide hydrochloride (651 mg, 1:85 mol), and triethylamine (0.851 mL, 6.11 mol). The resulting mixture was stirred for 30 minutes at 25° C. Then to it was added sodium triacetoxyborohydride (619 mg, 2.78 mmol) and the mixture was stirred at room temperature overnight. The reaction mixture was concentrated, and the residue was chromatographed on SiO₂, eluting with acetone/methanol (100% to 90%/10%) to give two fractions, F1 (404 mg) and F2 (368 mg) in a total of 73% yield. LCMS: (M+H)⁺ 571.1/569.1 for both isomers. Isomer 1 ¹H NMR (CD₃OD) δ 8.65 (t, 1H), 8.21 (s, 1H), 8.14 (d, 1H), 8.03 (dt, 1H), 7.88 (d, 1H), 7.69 (m, 2H), 4.23 (dd, 1H), 4.16 (s, 1H), 4.10 (m, 2H), 3.90 (m, 2H), 3.70 (m, 2H), 3.60 (dd, 1H), 3.52 (m, 2H), 2.55 (m, 1H), 2.42 (m, 2H), 2.22 (m, 3H), 1.80 (m, 4H).

Example 33

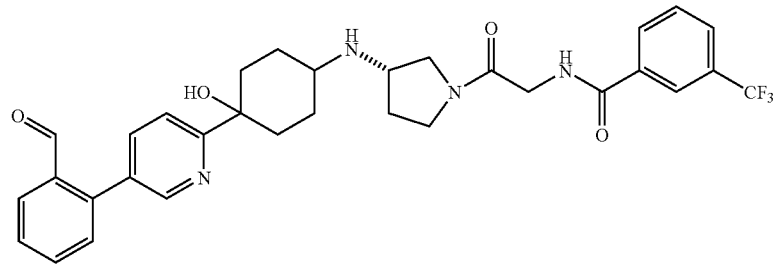

N-{2-[(3S)-3-({4-[5-(2-formylphenyl)pyridin-2-yl]-4-hydroxycyclohexyl}-amino)pyrrolidin-1-yl]-2-oxoethyl}-3-(trifluoromethyl)benzamide A solution of N-[2-((3S)-3-[4-(5-bromopyridin-2-yl)-4-hydroxycyclohexyl]aminopyrrolidin-1-yl)-2-oxoethyl]-3-(trifluoromethyl)benzamide (30.0 mg, 0.0527 mmol) and (2-formylphenyl)boronic acid (8.6 mg, 0.052 mmol) in DMF (0.60 mL) and aqueous sodium carbonate (2M, 0.198 mL) was degassed with N₂ for 5 minutes. Then [1,1'-bis(diphenylphosphino)ferrocene]-dichloropalladium(II), complex with dichloromethane (1:1) (2.2 mg, 0.0026 mmol) was added in under N₂ flush. The reaction mixture was degassed with N₂ for another 5 minutes and then the tube was sealed. The reaction mixture was heated under microwave at 130° C. for 5 minutes. After cooling down, the reaction mixture was filtered through a short pad of silica gel and washed with CH₃CN. The resulting solution was acidified with TFA to pH 1~2, then was subjected to purification on Prep-HPLC. The appropriate fractions were lypholized to give the product (23 mg, 53%) as a white powder. MS: (M+H)⁺ 595.

Example 34

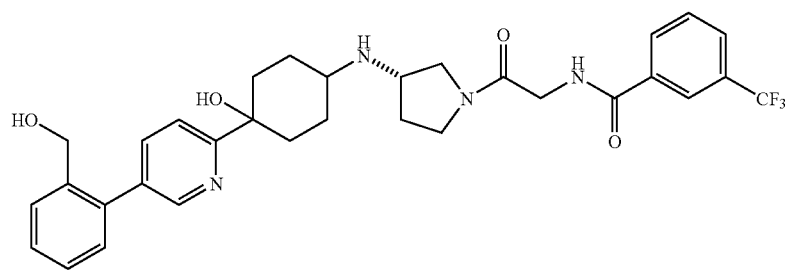

N-(2-(3S)-3-[(4-Hydroxy-4-5-[2-(hydroxymethyl) phenyl]pyridin-2-ylcyclohexyl)amino]pyrrolidin-1-yl-2-oxoethyl)-3-(trifluoromethyl)benzamide bis (trifluoroacetate)

To a solution of N-2-[(3S)-3-(4-[5-(2-formylphenyl)pyridin-2-yl]-4-hydroxycyclohexylamino)pyrrolidin-1-yl]-2-oxoethyl-3-(trifluoromethyl)benzamide bis(trifluoroacetate) (salt) (3.3 mg, 0.004 mmol) in methanol (0.50 mL) at 0° C. was added sodium borohydride (0.455 mg, 0.0120 mmol). The reaction mixture was allowed to warm up to room temperature and stirred at room temperature for 60 minutes and then at 60° C. for 60 minutes. The mixture was purified by prep-HPLC to afford the product as a TFA salt (1.1 mg, 33%). LCMS: (M+H)⁺ 597.2.

Example 35

Step A

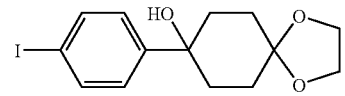

8-(4-Iodo-phenyl)-1,4-dioxa-spiro[4.5]decan-8-ol

To a solution of 1,4-diiodobenzene (16.5 g, 50 mmol) in THF (350 mL) at −78° C. was added n-BuLi (2.5 M, 24 mL) over 1 hour. After being stirred additional 30 minutes, a solution of 1,4-dioxa-spiro[4.5]decan-8-one (7.8 g, 50 mmol) in THF (30 mL) was added in and the resulting mixture was stirred for 3 hours. To the mixture was added TMSCl (5.4 g, 50 mmol) and the resulting mixture was allowed to warm to room temperature and stirred at room temperature for 18 hours. The reaction mixture was neutralized to pH 6.0, and extracted with ethyl acetate (3×50 mL). The organic extracts were combined, washed with saline solution (2×50 mL), dried over sodium sulfate, and concentrated in vacuo. The residue was chromatographed on silica gel, eluting with hexane/ethyl acetate (95/5 to 100/0). The appropriate fractions were combined to give 8-(4-Iodo-phenyl)-1,4-dioxa-spiro[4.5]decan-8-ol (12 g, 66.6%) with LCMS: 361.2 (M+H$^+$, 100%) and {[8-(4-iodophenyl)-1,4-dioxaspiro[4.5]dec-8-yl]oxy}(trimethyl)silane (6 g, 27%) with LCMS: 433.1 (M+H$^+$, 100%).

Step B

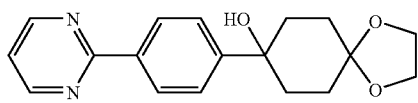 [SMILES: OC1(c2ccc(-c3ncccn3)cc2)CCC2(CC1)OCCO2]

8-(4-pyrimidin-2-ylphenyl)-1,4-dioxaspiro[4.5]decan-8-ol

To a solution of 8-(4-iodo-phenyl)-1,4-dioxa-spiro[4.5]decan-8-ol (450.0 mg, 1.249 mmol) in THF (1.0 mL) at room temperature was added dropwise isopropylmagnesium chloride (2.0 M in THF, 1.37 mL) and the reaction mixture was stirred at room temperature for 30 mins. To another flask charged with nickel acetylacetonate (20 mg, 0.06 mmol) and 1,3-bis(diphenylphosphino)-propane (26 mg, 0.062 mmol) suspended in THF (3 mL) under N$_2$ was added 2-bromopyrimidine (199 mg, 1.25 mmol). The resulting mixture was stirred at room temperature until it is clear. This mixture was transferred into the degassed Grignard solution prepared above. The resulting mixture was stirred at room temperature overnight. The reaction mixture was diluted with EtOAc, quenched with water, washed with brine, dried over Na$_2$SO$_4$, and concentrated. The residue was columned on silica gel, eluting with hexane/EtOAc (2/1), to gave the desired compound (270 mg, 69%) as a white solid. LCMS: 313.1, (M+H, 100%). $^1$H NMR (CDCl$_3$): δ 8.86 (d, 2H), 8.46 (dd, 2H), 7.71 (dd, 2H), 7.24 (t, 1H), 4.05 (d, 4H), 2.30 (dt, 2H), 2.18 (dt, 2H), 1.90 (m, 2H), 1.78 (m, 2H).

Step C

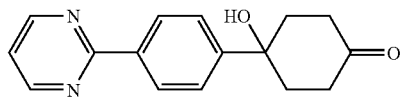

4-Hydroxy-4-(4-pyrimidin-2-ylphenyl)cyclohexanone

The title compound was prepared by treating the ketal of step B with HCl in water following the procedure described in step B of Example 2. MS (M+H)$^+$ 269.

Step D

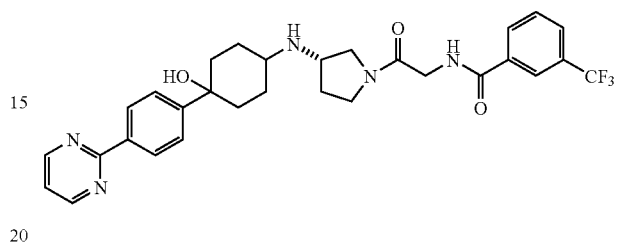

N-[2-((3S)-3-[4-hydroxy-4-(4-pyrimidin-2-ylphenyl)cyclohexyl]aminopyrrolidin-1-yl)-2-oxoethyl]-3-(trifluoromethyl)benzamide bis(trifluoroacetate) (salt)

To a 1-neck round-bottom flask charged with methylene chloride (1 mL) was added 4-hydroxy-4-(4-pyrimidin-2-ylphenyl)cyclohexanone (50.0 mg, 0.186 mmol), N-2-[(3S)-3-aminopyrrolidin-1-yl]-2-oxoethyl-3-(trifluoromethyl)benzamide hydrochloride (65.5 mg, 0.186 mmol), and triethylamine (85.7 uL, 0.615 mmol). The resulting mixture was stirred at 25° C. for 30 minutes, and to it was added sodium triacetoxyborohydride (62.4 mg, 0.28 mmol) in portion. The reaction mixture was stirred at room temperature overnight and concentrated. The residue was chromatographed on SiO2, eluting with acetone/methanol (100% to 90%/10%) to give two fractions, which were further purified on prep-LCMS separately to afford F1 (24.2 mg) and F2 (25.9 mg) as white powder in a total of 34% yield. LCMS: 568.2 (M+H, 100%) for both isomers.

The following Examples 36-37 were prepared in a similar manner.

Example 36

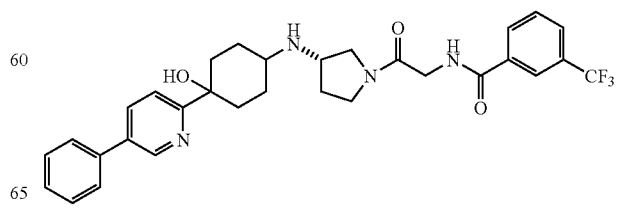

N-[2-((3S)-3-{[4-Hydroxy-4-(5-phenylpyridin-2-yl)cyclohexyl]amino}pyrrolidin-1-yl)-2-oxoethyl]-3-(trifluoromethyl)benzamide

MS (M+H)⁺ 567.

Example 37

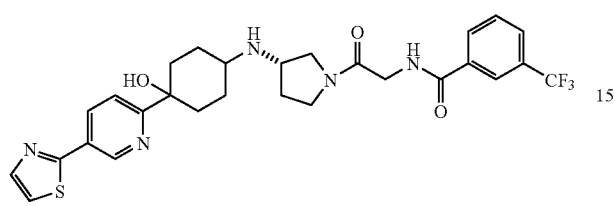

N-{2-[(3S)-3-({4-Hydroxy-4-[5-(1,3-thiazol-2-yl)pyridine-2-yl]cyclohexyl}amino)pyrrolidin-1-yl]-2-oxoethyl}-3-(trifluoromethyl)benzamide

MS (M+H)⁺ 574.

Example 38

Step A

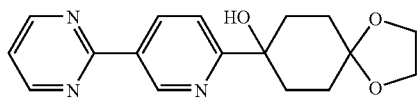 [SMILES: OC1(c2ccc(-c3ncccn3)cn2)CCC2(CC1)OCCO2]

8-(5-Pyrimidin-2-ylpyridin-2-yl)-1,4-dioxaspiro[4.5]decan-8-ol

A solution of 8-(5-bromopyridin-2-yl)-1,4-dioxaspiro[4.5]decan-8-ol (168.5 g, 0.5363 mol) in THF (2000 mL) was degassed with nitrogen for 30 minutes. A 2.0 M solution of isopropylmagnesium chloride in THF (563 mL) was added dropwise over 70 mins at room temperature to the above solution. The reaction mixture (light brownish color) was stirred for 180 minutes at 25° C.

Into another flask was charged with THF (500 mL) that was degassed with nitrogen for 10 min. To it were added Nickel acetylacetonate (6.9 g, 0.027 mol) and 1,2-bis(diphenylphosphino)-ethane (11 g, 0.027 mol) under nitrogen flush, and 10 minutes later 2-iodopyrimidine (113 g, 0.536 mol). After being stirred for 30 minutes at 25° C., the resulting light green suspension was transferred to the above solution. The reaction mixture was stirred at room temperature overnight and the reaction was found to be complete by HPLC. LC-MS: found (M+H) 314.20 for desired product. The reaction mixture was directly used for next reaction.

Step B

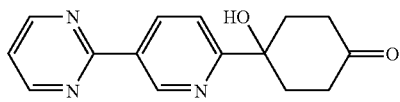

4-Hydroxy-4-(5-pyrimidin-2-ylpyridin-2-yl)cyclohexanone

About half of the THF in the reaction mixture from step A was removed by evaporation under reduced pressure. To the remaining reaction mixture was added a 4.00 M solution of HCl in water (900 mL). After being stirred for 1 hour, the mixture was diluted with 1000 mL water and neutralized with solid Na₂CO₃ to pH 8~9. Large amount of yellow solid precipitated out. The solid was filtered off and washed with ethyl acetate containing 1% aqueous NH₄OH (about 2000 mL) until no desired product was detected by TLC. The filtrate was partitioned and the aqueous layer was extracted with ethyl acetate (1200 mL×3). The combined organic layers were washed with brine, dried over magnesium sulfate and concentrated to half of the volume. The solid precipitating out was filtered and dissolved in dichloromethane (600 mL). The resulting solution was heated to reflux for 30 minutes and filtered. The filtrate was cooled in an ice bath. The solid precipitating out was collected by filtration to give 30 g of pure product. The mother liquids from the two crystallizations were combined and evaporated. The residue was taken into acetonitrile (500 mL). The resulting solution was heated to reflux until all solid was dissolved. Once insolubles were filtered off, the filtrate was allowed to stand at room temperature and solid was precipitated out. The solid was filtered and suspended in dichloromethane (700 mL). After being heated to reflux, the solution was filtered, evaporated to half of the volume, and cooled in an ice bath. The light brownish solid precipitating out was collected by filtration to give the second batch of solid (58 g). MS (M+H) 270.2.

Step C

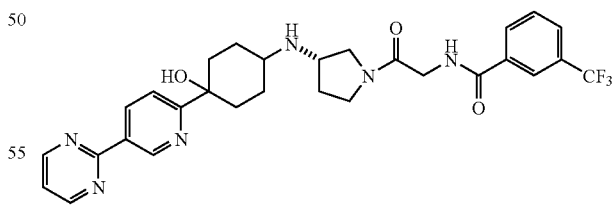

N-[2-((3S)-3-{[4-Hydroxy-4-(5-pyrimidin-2-ylpyridin-2-yl)cyclohexyl]amino}pyrrolidin-1-yl)-2-oxoethyl]-3-(trifluoromethyl)benzamide To a solution of N-{2-[(3S)-3-aminopyrrolidin-1-yl]-2-oxoethyl}-3-(trifluoromethyl)benzamide hydrochloride (22.10 g, 47.1 mmol) and 4-hydroxy-4-(5-pyrimidin-2-ylpyridin-2-yl)cyclohexanone (12.7 g, 47.1 mmol) in isobutyl alcohol (80.0 mL) was added triethylamine (19.7 mL, 141 mmol). The reaction mixture was cooled in an ice bath and stirred for 30 minutes. To it was added sodium triacetoxyborohydride (11.0 g, 51.8 mmol) in portion. After being stirred at room temperature for 4 hours, the solvent was removed by evaporation under reduced pressure. Saturated aqueous NaHCO₃ solution was added and the solution was extracted with ethyl acetate (150×3). The combined extracts were washed with brine, dried (Na₂SO₄), filtered, and concentrated. The residue was columned on silica gel, eluting with ethyl acetate (1% NH₄OH aqueous solution)/methanol (95/5 to 80/20). The appropriate fractions were combined and concentrated to give the title compound as a white powder (17.77 g). MS (M+H) 569.

The following examples were prepared in a similar manner.

Example 39

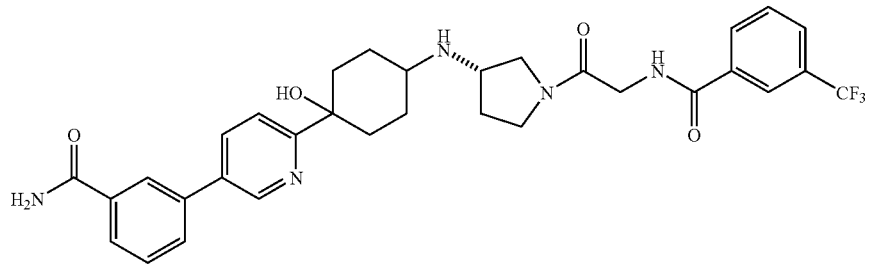

N-(2-{(3S)-3-[1(4-{5-[3-(Aminocarbonyl)phenyl]pyridin-2-yl}-4-hydroxycyclohexyl)-amino]pyrrolidin-1-yl}-2-oxoethyl)-3-(trifluoromethyl)benzamide

MS (M+H)⁺ 610.

Example 40

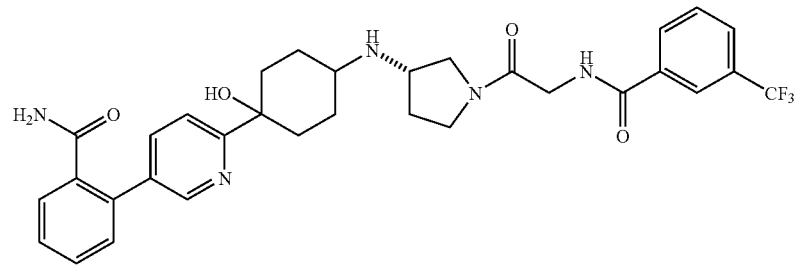

N-(2-{(3S)-3-[(4-{5-[2-(Aminocarbonyl)phenyl]pyridin-2-yl}-4-hydroxycyclohexyl)amino]pyrrolidin-1-yl}-2-oxoethyl)-3-(trifluoromethyl)benzamide

MS (M+H)⁺ 610.

Example 41

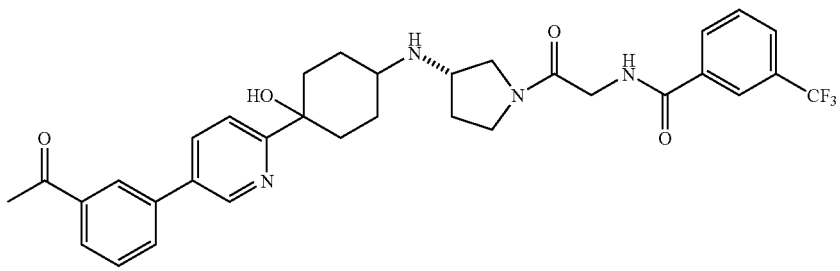

N-{2-[(3S)-3-({4-[5-(3-Acetylphenyl)pyridin-2-yl]-4-hydroxycyclohexyl}amino)-pyrrolidin-1-yl]-2-oxoethyl}-3-(trifluoromethyl)benzamide

MS (M+H)+ 609.

Example 42

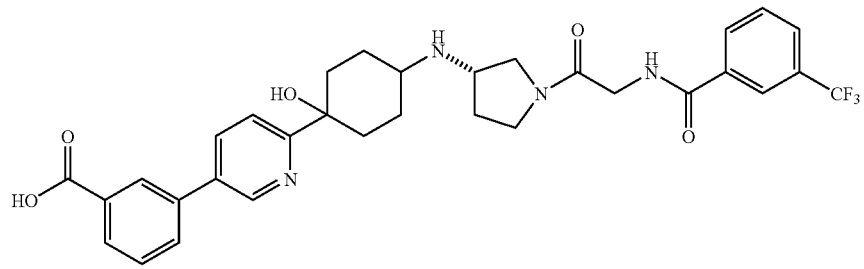

3-[6-(1-Hydroxy-4-{[(3S)-1-({[3-(trifluoromethyl)benzoyl]amino}acetyl)-pyrrolidin-3-yl]amino}cyclohexyl)pyridin-3-yl]benzoic acid

MS (M+H)+ 611.

Example 43

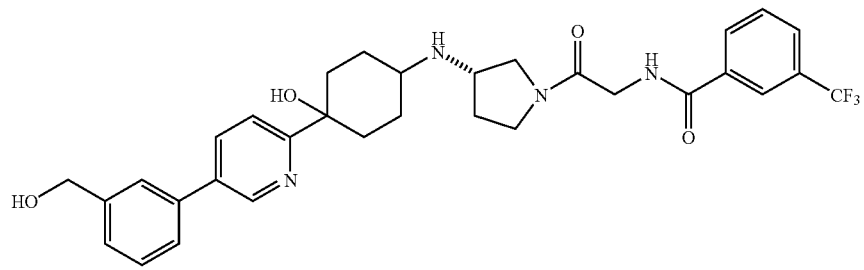

N-(2-{(3S)-3-[(4-Hydroxy-4-{5-[3-(hydroxymethyl)phenyl]pyridin-2-yl}cyclohexyl)amino]pyrrolidin-1-yl}-2-oxoethyl)-3-(trifluoromethyl)benzamide

MS (M+H)+ 597.

Example 44

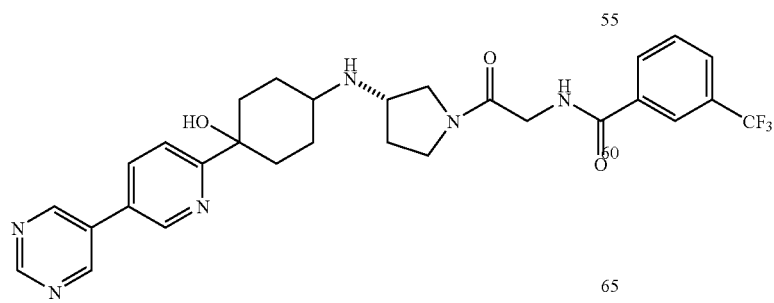

N-[2-((3S)-3-{[4-Hydroxy-4-(5-pyrimidin-5-ylpyridin-2-yl)cyclohexyl]amino}-pyrrolidin-1-yl)-2-oxoethyl]-3-(trifluoromethyl)benzamide
MS (M+H)+ 569.
Example 45
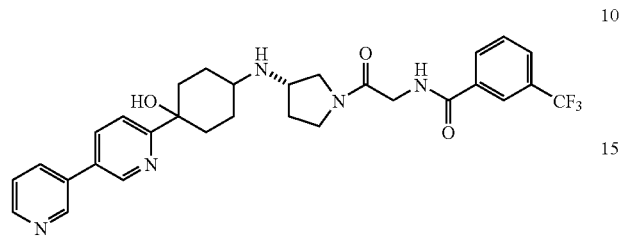
N-[2-((3S)-3-{[4-(3,3'-Bipyridin-6-yl)-4-hydroxycyclohexyl]amino}pyrrolidin-1-yl)-2-oxoethyl]-3-(trifluoromethyl)benzamide
MS (M+H)+ 568.
Example 46
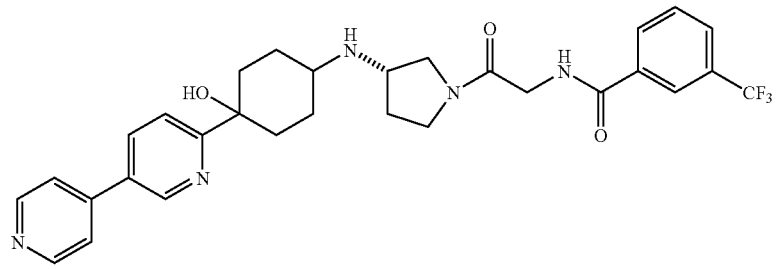
N-[2-((3S)-3-{[4-(3,4'-Bipyridin-6-yl)-4-hydroxycyclohexyl]amino}pyrrolidin-1-yl)-2-oxoethyl]-3-(trifluoromethyl)benzamide
MS (M+H)+ 568.
Example 47
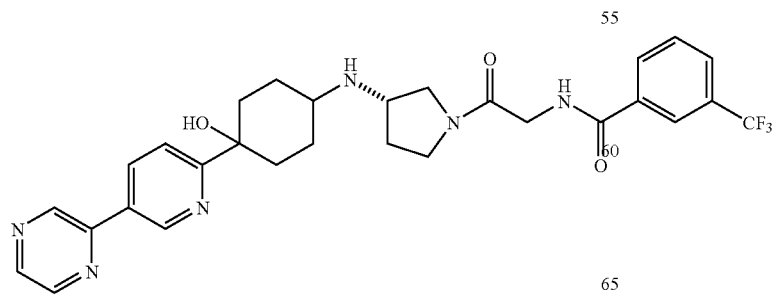

N-[2-((3S)-3-{[4-Hydroxy-4-(5-pyrazin-2-ylpyridin-2-yl)cyclohexyl]amino}pyrrolidin-1-yl)-2-oxoethyl]-3-(trifluoromethyl)benzamide

MS (M+H)+ 569.

Example 48

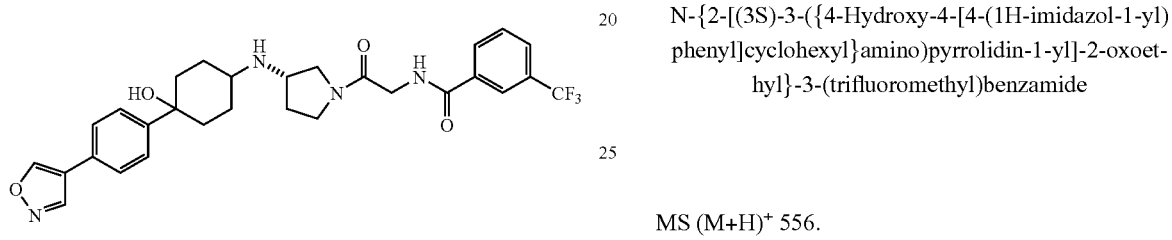

N-{2-[(3S)-3-({4-Hydroxy-4-[4-(1H-imidazol-1-yl)phenyl]cyclohexyl}amino)pyrrolidin-1-yl]-2-oxoethyl}-3-(trifluoromethyl)benzamide

MS (M+H)+ 556.

Example 50

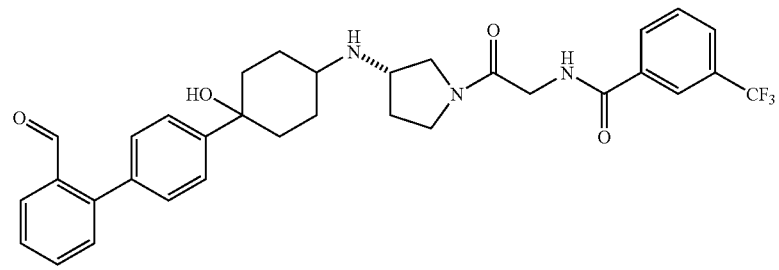

N-[2-((3S)-3-{[4-Hydroxy-4-(4-isoxazol-4-ylphenyl)cyclohexyl]amino}pyrrolidin-1-yl)-2-oxoethyl]-3-(trifluoromethyl)benzamide

MS (M+H)+ 557.

Example 49

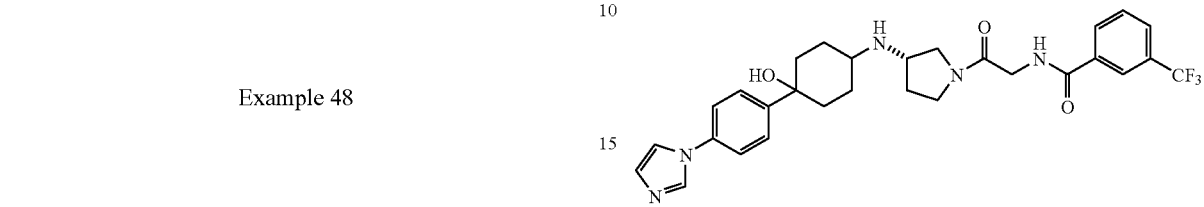

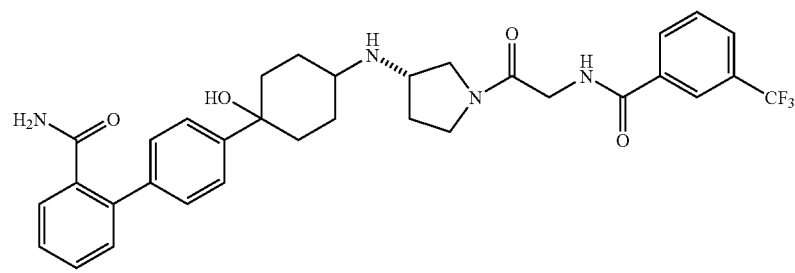

4'-(1-Hydroxy-4-{[(3S)-1-({[3-(trifluoromethyl)benzoyl]amino}acetyl)pyrrolidin-3-yl]amino}cyclohexyl)biphenyl-2-carboxamide

MS (M+H)+ 609.

Example 51

N-[2-((3S)-3-{[4-(2'-Formylbiphenyl-4-yl)-4-hydroxycyclohexyl]amino}-pyrrolidin-1-yl)-2-oxoethyl]-3-(trifluoromethyl)benzamide

MS (M+H)⁺ 594.

Example 52

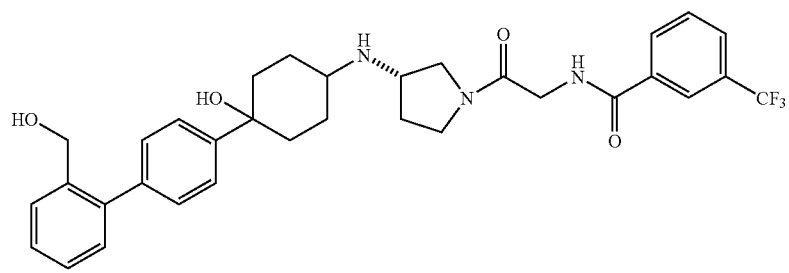

N-{2-[(3S)-3-({4-Hydroxy-4-[2'-(hydroxymethyl)biphenyl-4-yl]cyclohexyl}amino)-pyrrolidin-1-yl]-2-oxoethyl}-3-(trifluoromethyl)benzamide

MS (M+H)⁺ 596.

Example 53

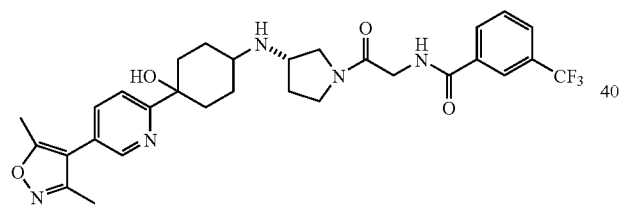

N-{2-[(3S)-3-({4-[5-(3,5-Dimethylisoxazol-4-yl)pyridin-2-yl]-4-hydroxycyclohexyl}-amino)pyrrolidin-1-yl]-2-oxoethyl}-3-(trifluoromethyl)benzamide

MS (M+H)⁺ 586.

Example 54

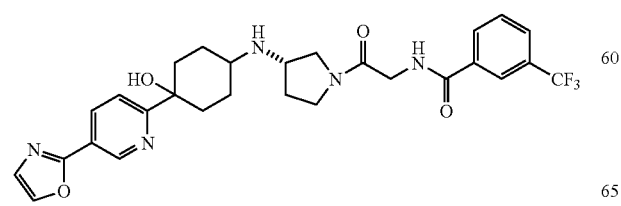

N-{2-[(3S)-3-({4-Hydroxy-4-[5-(1,3-oxazol-2-yl)pyridin-2-yl]cyclohexyl}amino)pyrrolidin-1-yl]-2-oxoethyl}-3-(trifluoromethyl)benzamide

MS (M+H)⁺ 574.

Example 55

Step A

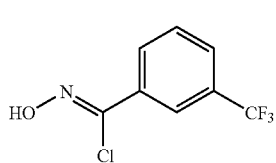 [SMILES: O/N=C(\Cl)c1cccc(C(F)(F)F)c1]

3-(Trifluoromethyl)benzaldehyde oxime

To a flask containing 3-trifluorobenzaldehyde (1.74 g, 10 mmol) and hydroxylamine hydrochloride (0.76 g, 11 mmol) in methanol (25 mL) was added TEA (0.65 g, 11 mmol). The reaction mixture was heated to reflux for 3 h, neutralized to pH 6.0, and extracted with ethyl acetate (3×20 mL). The organic extracts were combined, washed with saline solution (20 mL), dried over sodium sulfate, concentrated in vacuo to give the oxime (1.9 g) as a colorless oil. LCMS: (M+H)⁺ 190.2.

Step B

3-(Trifluoromethyl)benzaldehyde oxime

To a dried flask containing 3-(trifluoromethyl)benzaldehyde oxime (1.89 g, 10 mmol) in methylene chloride (100 mL) was added N-chlorosuccinimide (1.40 g, 10.5 mmol) slowly at 0° C. The reaction mixture was warmed to 45° C. for 2 h, poured over ice, diluted with $H_2O$ (20 mL), and extracted with EtOAc (100 mL). The organic phase was washed with $H_2O$ (2×25 mL) and saline solution (25 mL), dried over sodium sulfate, concentrated in vacuo to give the oxime (2 g, 90%). LCMS: $(M+H)^+$ 224.4.

Step C

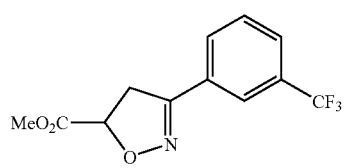 [SMILES: COC(=O)C1CC(c2cccc(C(F)(F)F)c2)=NO1]

Methyl 3-[3-(Trifluoromethyl)phenyl]-4,5-dihydroisoxazole-5-carboxylate

To a flask containing N-hydroxy-3-(trifluoromethyl)benzenecarboximidoyl chloride (2.0 g, 8.9 mmol) and methyl acrylate (0.7 g, 8 mmol) in methylene chloride (100 mL) at 0° C. under an inert atmosphere was added TEA (0.90 g, 8.8 mmol). The reaction mixture was slowly warmed to ambient temperature, stirred for 20 h, quenched with water (30 mL), and extracted with methylene chloride (2×50 mL). The organic extracts were combined, washed with saline solution (50 mL), dried over sodium sulfate, concentrated in vacuo, and chromatographed on silica gel, eluting with methylene chloride/methanol (100/1 to 95/5). The appropriate fractions were combined and concentrated in vacuo to give the title compound (2.3 g, 100%): LCMS: $(M+H)^+$ 274.2. $^1H$ NMR: ($CDCl_3$) δ 8.03 (s, 1H), 7.92 (d, 1H), 7.71 (d, 1H), 7.59 (dd, 1H), 5.28 (dd, 1H), 3.86 (s, 3H), 3.71 (dd, 2H).

Step D

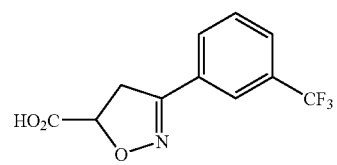 [SMILES: O=C(O)C1CC(c2cccc(C(F)(F)F)c2)=NO1]

3-[3-(Trifluoromethyl)phenyl]-4,5-dihydroisoxazole-5-carboxylic Acid

To a solution of methyl 3-[3-(trifluoromethyl)phenyl]-4,5-dihydroisoxazole-5-carboxylate (2.3 g, 8.4 mmol) in THF (10 mL) was added a 2 M solution of sodium hydroxide in water (10 mL) at 0° C. The reaction mixture was slowly warmed to ambient temperature, stirred for 2 h, neutralized with 2 N HCl to pH 7, and extracted with ethyl acetate (2×50 mL). The organic extracts were combined, washed with saline solution (50 mL), dried over sodium sulfate, and concentrated in vacuo. The residue was chromatographed on silica gel, eluting with methylene chloride/methanol (95/5 to 80/20). The appropriate fractions were combined and concentrated in vacuo to give the title compound (2.18 g, 100%) as a white crystalline solid. LCMS: $(M-H)^-$ 258.2.

Step E

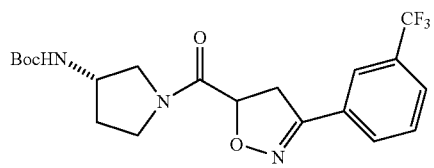 [SMILES: CC(C)(C)OC(=O)N[C@H]1CCN(C(=O)C2CC(c3cccc(C(F)(F)F)c3)=NO2)C1]

tert-Butyl [(3S)-1-(3-[3-(Trifluoromethyl)phenyl]-4,5-dihydroisoxazol-5-ylcarbonyl)pyrrolidin-3-yl]carbamate To a solution of 3-[3-(trifluoromethyl)phenyl]-4,5-dihydroisoxazole-5-carboxylic acid (259 mg, 1 mmol) and tert-butyl (3S)-pyrrolidin-3-ylcarbamate (186 mg, 1 mmol) in DMF (0.5 mL) and methylene chloride (5 mL) at 0° C. was added triethylamine (120 mg, 1.2 mmol) and benzotriazol-1-yloxytris(dimethylamino)-phosphonium hexafluorophosphate (442 mg, 1 mmol). The mixture was allowed to warm to room temperature over 1 h and stirred at room temperature for 1 h. The mixture was concentrated in vacuo, and the residue was chromatographed on silica gel, eluting with 1% $NH_4OH$ in ethyl acetate to give the desired coupling intermediate (410 mg) as a white solid. LCMS: $(M+H)^+$ 428.4.

Step F

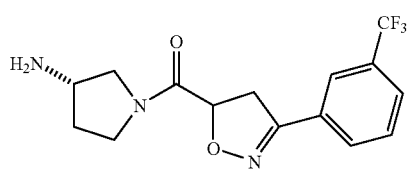 [SMILES: N[C@H]1CCN(C(=O)C2CC(c3cccc(C(F)(F)F)c3)=NO2)C1]

(3S)-1-(3-[3-(Trifluoromethyl)phenyl]-4,5-dihydroisoxazol-5-ylcarbonyl)-pyrrolidin-3-amine hydrochloride To a solution of the intermediate of step E in methylene chloride (5 mL) was added 4 M HCl in dioxane (5 mL). After stirred at room temperature for 2 h, the resulting solution was concentrated in vacuo to give the HCl salt (350 mg) of the amine as a white solid. LCMS: (M+H)+ 364.4.

Step G

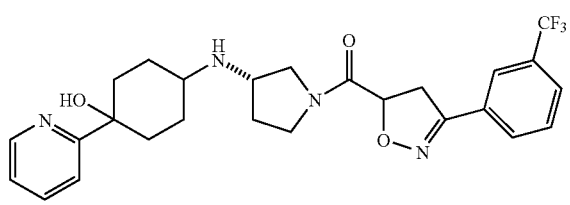 [SMILES: O=C(C1CC(c2cccc(C(F)(F)F)c2)=NO1)N1CC[C@H](NC2CCC(O)(c3ccccn3)CC2)C1]

1-Pyridin-2-yl-4-[(3S)-1-(3-[3-(trifluoromethyl)phenyl]-4,5-dihydroisoxazol-5-ylcarbonyl)pyrrolidin-3-yl]aminocyclohexanol To a solution of (3S)-1-(3-[3-(trifluoromethyl)phenyl]-4,5-dihydroisoxazol-5-ylcarbonyl)pyrrolidin-3-amine hydrochloride (178 mg, 0.489 mmol) and 4-hydroxy-4-pyridin-2-yl-cyclohexanone (95.1 mg, 0.498 mmol) in methylene chloride (6 mL) was added triethylamine (50.3 mg, 0.498 mmol) and then NaBH(OAc)$_3$ (120 mg, 0.54 mmol). After being stirred at room temperature for 2 h, the reaction mixture was neutralized with 1 N NaOH to pH 7, and extracted with ethyl acetate (2×25 mL). The organic extracts were combined, washed with saline solution (20 mL), dried over sodium sulfate, concentrated in vacuo, and chromatographed on silica gel, eluting with 1% NH$_4$OH in ethyl acetate/methanol (95/5 to 80/20). The appropriate fractions were combined and concentrated in vacuo to give two fractions of the desired compounds: peak 1 (100 mg) and peak 2 (85 mg). Both fractions were further purified by HPLC on a C18 column, eluting with 1% NH$_4$OH in water/acetonitrile, to give peak 1 (68 mg) and peak 2 (65 mg) as white solids. Both compounds have LCMS: (M+H)+ 503.3. Peak 1 shows two peaks in a 1 to 1 ratio in a chiral analytical column. Peak 2 shows two peaks in a 1 to 10 ratio in a chiral analytical column.

The following Examples 56-58 were prepared in a fashion similar to Example 55.

Example 56

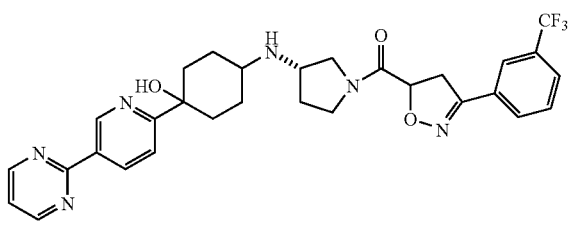 [SMILES: O=C(C1CC(c2cccc(C(F)(F)F)c2)=NO1)N1CC[C@H](NC2CCC(O)(c3ccc(-c4ncccn4)cn3)CC2)C1]

1-(5-Pyrimidin-2-ylpyridin-2-yl)-4-{[(3S)-1-({3-[3-(trifluoromethyl)phenyl]-4,5-dihydroisoxazol-5-yl}carbonyl)pyrrolidin-3-yl]amino}cyclohexanol

MS (M+H)+ 581.

Example 57

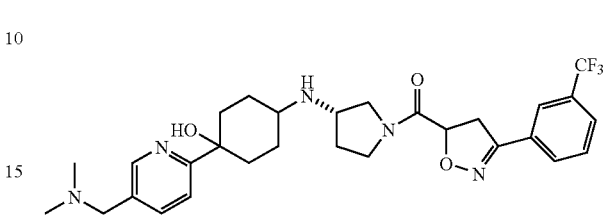

1-{5-[(Dimethylamino)methyl]pyridin-2-yl}-4-{[(3S)-1-({3-[3-(trifluoromethyl)phenyl]-4,5-dihydroisoxazol-5-yl}carbonyl)pyrrolidin-3-yl]amino}cyclohexanol

MS (M+H)+ 560.

Example 58

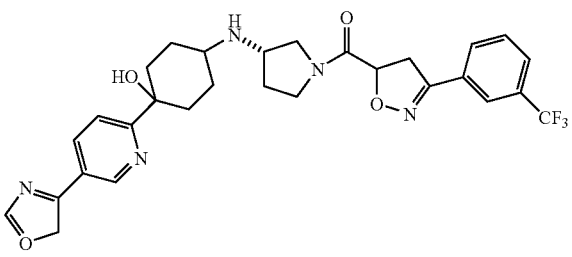

1-[5-(1,3-Oxazol-2-yl)pyridin-2-yl]-4-{[(3S)-1-({3-[3-(trifluoromethyl)phenyl]-4,5-dihydroisoxazol-5-yl}carbonyl)pyrrolidin-3-yl]amino}cyclohexanol

MS (M+H) 570.3.

Example 59

Step A

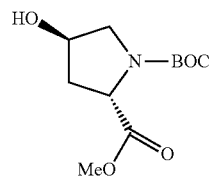

Methyl (2S,4R)—N-tert-Butoxycarbonyl-4-hydroxy-2-pyrrolidinecarboxylate

L-trans-4-Hydroxyproline methyl ester hydrochloride (25.00 g, 138.0 mmol) was dissolved in dichloromethane (300 mL) and triethylamine (58.0 mL, 413 mmol). The solution was cooled to 0° C. and then di-tert-butyldicarbonate (33.00 g, 151.0 mmol) was added in small portions. After stirring at room temperature overnight, the mixture was concentrated to a thick white sludge. The residue was dissolved in ethyl acetate and the organic layer was washed successively with $NH_4Cl/H_2O$, $NaHCO_3/H_2O$ and brine. The organic extracts were dried over $MgSO_4$, filtered, and concentrated to give 33.0 g (99%) of desired product as a colorless oil. LC/MS $(M+Na)^+$ m/z=267.9. $^1H$ NMR ($CDCl_3$) δ 4.50 (m, 1H), 4.40 (m, 1H), 3.75 (s, 3H), 3.43-3.68 (m, 2H), 2.30 (m, 1H), 1.95-2.15 (m, 2H), 1.42 and 1.45 (s, 9H).

Step B

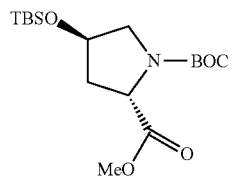 [SMILES: COC(=O)[C@@H]1C[C@@H](O[Si](C)(C)C(C)(C)C)CN1C(=O)OC(C)(C)C]

1-tert-Butyl 2-Methyl (2S,4R)-4-{[tert-butyl(dimethyl)silyl]oxy}pyrrolidine-1,2-dicarboxylate Methyl (2S,4R)—N-tert-butoxycarbonyl-4-hydroxy-2-pyrrolidinecarboxylate (22.1 g, 82.6 mmol) was dissolved in dry DMF (100 mL) under nitrogen. Imidazole (16.8 g, 248 mmol) was added and the mixture cooled to 0° C. tert-Butyldimethylsilyl chloride (13.1 g, 86.7 mmol) was added in small portions and then the mixture was allowed to warm to room temperature. After stirring overnight, the mixture was diluted with 300 mL ethyl acetate and washed with water three times (500 mL, 200 mL, 200 mL). The organic extracts were washed one final time with brine and then dried over $MgSO_4$, filtered and concentrated to give 29.5 g (99%) of desired product as a colorless oil. LC/MS $(M-Boc+H)^+$ m/z=260.2. $^1H$ NMR ($CDCl_3$) δ 4.30-4.47 (m, 2H), 3.73 and 3.75 (s, 3H), 3.60 (m, 1H), 3.28-3.45 (m, 1H), 2.18 (m, 1H), 2.03 (m, 1H), 1.42 and 1.47 (s, 9H), 0.87 (s, 9H), 0.06 (s, 6H).

Step C

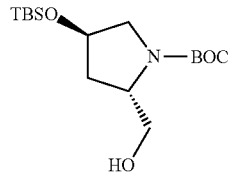 [SMILES: CC(C)(C)OC(=O)N1C[C@H](O[Si](C)(C)C(C)(C)C)C[C@H]1CO]

tert-Butyl (2S,4R)-4-{[tert-Butyl(dimethyl)silyl]oxy}-2-(hydroxymethyl)-pyrrolidine-1-carboxylate 1-tert-Butyl 2-methyl (2S,4R)-4-{[tert-butyl(dimethyl)silyl]-oxy}pyrrolidine-1,2-dicarboxylate (5.00 g, 13.91 mmol) was dissolved in dry THF (50 mL) under nitrogen and cooled to −78° C. Diisobutylaluminum hydride solution (31.0 mL, 31.0 mmol, 1.0 M in toluene) was added dropwise over 30 minutes. After stirring for ten minutes, the mixture was slowly warmed to room temperature at which point TLC indicated complete conversion. The mixture was diluted with ethyl acetate (200 mL) and saturated aqueous sodium potassium tartrate (200 mL). The mixture was stirred vigorously for 30 minutes until two phases were apparent. The aqueous layer was then extracted twice with ethyl acetate and washed with brine. The organic layer was dried over $MgSO_4$, filtered and concentrated to give 4.91 g of the crude alcohol as a pale yellow oil. LC/MS $(M-Boc+H)^+$ m/z=232.2. $^1H$ NMR ($CDCl_3$) δ 4.88 (d, 1H), 4.27 (bs, 1H), 4.14 (m, 1H), 3.69 (t, 1H), 3.54 (m, 1H), 3.42 (d, 1H), 3.34 (dd, 1H), 1.96 (m, 1H), 1.58 (m, 1H), 1.47 (s, 9H), 0.87 (s, 9H), 0.06 (s, 6H).

Step D

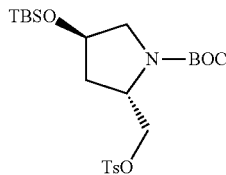 [SMILES: Cc1ccc(S(=O)(=O)OC[C@@H]2C[C@@H](O[Si](C)(C)C(C)(C)C)CN2C(=O)OC(C)(C)C)cc1]

tert-Butyl (2S,4R)-4-{[tert-Butyl(dimethyl)silyl]oxy}-2-({[(4-methylphenyl)-sulfonyl]-oxy}methyl)pyrrolidine-1-carboxylate tert-Butyl (2S,4R)-4-{[tert-butyl(dimethyl)silyl]oxy}-2-(hydroxymethyl)pyrrolidine-1-carboxylate (4.91 g, 14.8 mmol) was dissolved in dichloromethane (70 mL) under nitrogen. Triethylamine (5.8 mL, 41.7 mmol) was added followed by p-toluenesulfonyl chloride (3.18 g, 16.7 mmol) and the mixture was stirred at room temperature overnight. TLC revealed about half conversion. Pyridine (3.4 mL, 41 mmol) was added to the mixture which turned dark orange after 20 minutes. After two more days, the mixture was diluted with ethyl acetate and the organic layer was washed successively with $NaHCO_3/H_2O$, $NH_4Cl/H_2O$, water, and brine. The organic extract was dried over $MgSO_4$, filtered and concentrated to a red oil which was chromatographed on silica gel (10% to 20% ethyl acetate/hexane). Pure fractions were combined to give the tosylate as a yellow oil, 6.32 g (93%, 2 steps). $^1H$ NMR ($CDCl_3$) δ 7.77 (d, 2H), 7.34 (t, 2H), 4.30 (m, 2H), 4.10 (m, 2H), 3.30 (m, 2H), 2.45 (s, 3H), 1.97 (m, 2H), 1.41 and 1.37 (s, 9H), 0.85 (s, 9H), 0.06 (s, 6H).

Step E

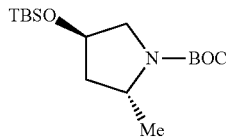 [SMILES: C[C@@H]1C[C@@H](O[Si](C)(C)C(C)(C)C)CN1C(=O)OC(C)(C)C]

tert-Butyl (2R,4R)-4-{[tert-Butyl(dimethyl)silyl]oxy}-2-methylpyrrolidine-1-carboxylate tert-Butyl (2S,4R)-4-{[tert-butyl(dimethyl)silyl]oxy}-2-({[(4-methylphenyl)-sulfonyl]-oxy}methyl)pyrrolidine-1-carboxylate (6.32 g, 13.01 mmol) was dissolved in THF (50 mL) under nitrogen and cooled to 0° C. Lithium triethylborohydride solution (Super Hydride, 14.3 mL, 1.0 M in THF) was added dropwise and the mixture was then slowly warmed to room temperature. After 2 hours, TLC revealed half conversion. More lithium triethylborohydride solution (12.0 mL) was added and the solution stirred at room temperature overnight. Diluted with NaHCO$_3$/H$_2$O and extracted twice with ethyl acetate. Washed organic layer with NH$_4$Cl/H$_2$O and brine. Dried organic extracts over MgSO$_4$, filtered and concentrated to give a colorless oil. Chromatographed on silica gel eluting with 10% ethyl acetate/hexane. Pure fractions were combined to give the desired product as a colorless oil, 3.74 g (91%). LC/MS (M+Na)$^+$ m/z=338.2. $^1$H NMR (CDCl$_3$) δ 4.34 (m, 1H), 3.95 (m, 1H), 3.35 (m, 2H), 1.98 (m, 1H), 1.65 (m, 1H), 1.47 (s, 9H), 1.20 (bs, 3H), 0.87 (s, 9H), 0.06 (s, 6H).

Step F

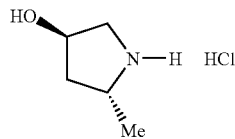

(3R,5R)-5-Methylpyrrolidin-3-ol hydrochloride tert-Butyl (2R,4R)-4-{[tert-butyl(dimethyl)silyl]oxy}-2-methylpyrrolidine-1-carboxylate (3.74 g, 11.85 mmol) was dissolved in dry THF (20 mL) under nitrogen. Hydrogen chloride solution (40 mL, 4.0 M solution in 1,4-dioxane) was added and the mixture was stirred at room temperature for four hours. The solution was concentrated on the rotovap to an oil which was azeotroped with toluene and pumped under vacuum to provide the hydrochloride salt as an off white solid, 80 g (100%) which was used for the next step without further purification. $^1$H NMR (CD$_3$OD) δ 4.54 (m, 1H), 3.95 (m, 1H), 3.44 (dd, 1H), 3.18 (d, 1H), 2.19 (dd, 1H), 1.76 (m, 1H), 1.44 (d, 3H).

Step G

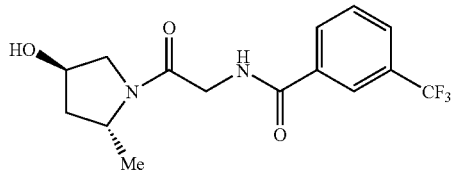 [SMILES: C[C@@H]1C[C@@H](O)CN1C(=O)CNC(=O)c1cccc(C(F)(F)F)c1]

N-{2-[(2R,4R)-4-Hydroxy-2-methylpyrrolidin-1-yl]-2-oxoethyl}-3-(trifluoro-methyl)benzamide (3R,5R)-5-Methylpyrrolidin-3-ol hydrochloride (1.80 g, 13 mmol) was dissolved in dichloromethane (50 mL) and diisopropylethylamine (2.1 mL, 12.0 mmol) under nitrogen. (3-Trifluoromethyl-benzoylamino)-acetic acid (2.93 g, 11.85 mmol) was added followed by EDC (3.41 g, 17.8 mmol) and the mixture was stirred at room temperature for four hours. The mixture was diluted with NH$_4$Cl/H$_2$O and extracted twice with ethyl acetate. The combined extracts were washed with NaHCO$_3$/H$_2$O and brine, dried over MgSO$_4$, filtered and concentrated to give a dark orange oil. Chromatography on silica gel eluting with ethyl acetate to 5% methanol/ethyl acetate gave the coupled product as a pale orange solid, 3.19 g (81%, 2 steps). LC/MS (M+H)$^+$ m/z=331.1. $^1$H NMR (CDCl$_3$, major rotamer) δ 8.12 (s, 1H), 8.01 (d, 1H), 7.76 (d, 1H), 7.57 (t, 1H), 7.50 (m, 1H), 4.56 (m, 1H), 4.34 (m, 1H), 4.23 (m, 1H), 4.11 (m, 1H), 3.61 (dd, 1H), 3.51 (d, 1H), 2.71 (d, 1H), 2.17 (m, 1H), 1.81 (m, 1H), 1.32 (d, 3H).

Step H

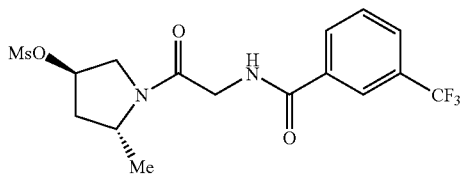 [SMILES: C[C@@H]1C[C@@H](OS(C)(=O)=O)CN1C(=O)CNC(=O)c1cccc(C(F)(F)F)c1]

(3R,5R)-5-Methyl-1-({[3-(trifluoromethyl)benzoyl]amino}acetyl)pyrrolidin-3-yl methanesulfonate To a solution of N-{2-[(2R,4R)-4-hydroxy-2-methylpyrrolidin-1-yl]-2-oxoethyl}-3-(trifluoromethyl)benzamide (1.50 g, 4.54 mmol) in dichloromethane (30 mL) and pyridine (1.83 mL, 22.7 mmol) under nitrogen at 0° C. was added methanesulfonyl chloride (0.42 mL, 5.45 mmol) dropwise. After being stirred at 0° C. for two hours, the reaction was allowed to slowly warm to room temperature and stirred overnight. The mixture was diluted with NaHCO$_3$/H$_2$O and extracted with ethyl acetate. The organic layer was washed with NH$_4$Cl/H$_2$O and brine, dried over MgSO$_4$, filtered and concentrated to give the mesylate as a brown oil, 1.87 g (100%). LC/MS (M+H)$^+$ m/z=409.0. $^1$H NMR (CDCl$_3$, major rotamer) δ 8.12 (s, 1H), 8.01 (d, 1H), 7.78 (d, 1H), 7.59 (t, 1H), 7.29 (bs, 1H), 5.33 (m, 1H), 4.37 (m, 1H), 4.18 (m, 2H), 3.86 (d, 1H), 3.76 (dd, 1H), 3.08 (s, 3H), 2.51 (m, 1H), 1.94 (m, 1H), 1.38 (d, 3H).

Step I

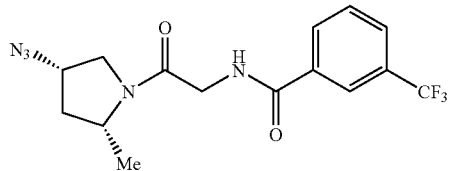 [SMILES: C[C@@H]1C[C@H](N=[N+]=[N-])CN1C(=O)CNC(=O)c1cccc(C(F)(F)F)c1]

N-{2-[(2R,4S)-4-Azido-2-methylpyrrolidin-1-yl]-2-oxoethyl}-3-(trifluoromethyl)benzamide To a solution of the crude mesylate (1.87 g) in dry DMF (20 mL) was added sodium azide (1.50 g, 22.7 mmol). The mixture was stirred at 60-65° C. for five hours, then 50° C. for twenty hours. Ethyl acetate was added. The organic layer was separated, washed twice with water and then with brine, dried over MgSO$_4$, filtered and concentrated to an orange oil. Chromatography on silica gel eluting with 80% ethyl acetate/hexane gave the azide as a yellow oil, 1.33 g (82%). LC/MS (M+H)$^+$ m/z=356.1. $^1$H NMR (CDCl$_3$, major rotamer) δ 8.12

(s, 1H), 8.00 (t, 1H), 7.77 (d, 1H), 7.58 (t, 1H), 7.37 (bs, 1H), 4.35 (m, 2H), 4.17 (m, 2H), 3.73 (dd, 1H), 3.50 (d, 1H), 2.39 (m, 1H), 1.87 (d, 1H), 1.43 (d, 3H).

Step J

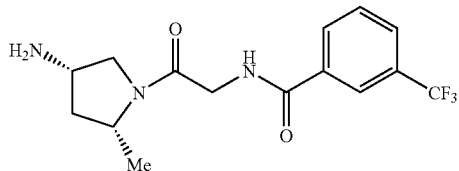 [SMILES: C[C@@H]1C[C@H](N)CN1C(=O)CNC(=O)c1cccc(C(F)(F)F)c1]

N-{2-[(2R,4S)-4-Amino-2-methylpyrrolidin-1-yl]-2-oxoethyl}-3-(trifluoromethyl)benzamide N-{2-[(2R,4S)-4-Azido-2-methylpyrrolidin-1-yl]-2-oxoethyl}-3-(trifluoromethyl)benzamide (1.33 g, 3.74 mmol) was dissolved in ethanol (50 mL) and then 10% Pd—C (130 mg) was added to the solution. The flask was purged with hydrogen and then stirred under an atmosphere of hydrogen using a balloon for four hours at which point, TLC indicated complete consumption of starting material. The reaction was then flushed with nitrogen and filtered through Celite on a glass frit and washed with methanol. The filtrate was concentrated to give the desired amine as a dark brown oil, 1.21 g (98%). LC/MS (M+H)$^+$ m/z=330.1. $^1$H NMR (CDCl$_3$) δ 8.12 (s, 1H), 8.02 (d, 1H), 7.77 (d, 1H), 7.58 (t, 1H), 7.37 (bs, 1H), 4.16 (m, 3H), 3.72 (m, 1H), 3.61 (m, 1H), 3.15 (m, 1H), 2.44 (m, 1H), 1.70-1.20 (m, 3H), 1.43 (d, 3H); $^{19}$F NMR (CDCl$_3$) δ −63.12 (s).

Step K

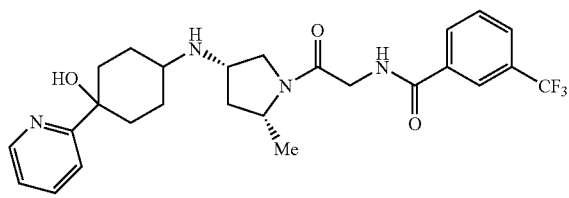 [SMILES: C[C@@H]1C[C@H](NC2CCC(O)(c3ccccn3)CC2)CN1C(=O)CNC(=O)c1cccc(C(F)(F)F)c1]

N-(2-{(2R,4S)-4-[(4-Hydroxy-4-pyridin-2-ylcyclohexyl)amino]-2-methyl-pyrrolidin-1-yl}-2-oxoethyl)-3-(trifluoromethyl)benzamide N-{2-[(2R,4S)-4-Amino-2-methylpyrrolidin-1-yl]-2-oxoethyl}-3-(trifluoromethyl)benzamide (200 mg, 0.607 mmol) and 4-hydroxy-4-pyridin-2-yl-cyclohexanone (116 mg, 0.607 mmol) were dissolved in 2-propanol (10 mL). After stirring for 30 minutes, sodium triacetoxyborohydride (257 mg, 1.21 mmol) was added and the mixture was stirred at room temperature overnight. TLC indicated complete conversion to desired products in about a 1:1 ratio of two isomers. The reaction mixture was chromatographed on silica gel eluting with dichloromethane to 10% methanol/dichloromethane/0.5% ammonium hydroxide to give 229 mg (75%) as a mixture of isomers. $^1$H NMR (CDCl$_3$, mixture of isomers) δ 8.53 (m, 1H), 8.13 (bs, 1H), 8.02 (d, 1H), 7.75 (m, 2H), 7.58 (t, 1H), 7.40 (m, 2H), 7.22 (m, 1H), 4.05-4.38 (m, 3H), 3.80 (m, 1H), 3.56 (m, 1H), 3.42 (m, 1H), 3.19 (m, 1H), 3.04 (m, 1H), 2.65 (m, 1H), 2.47 (m, 1H), 2.16 (m, 2H), 1.40-2.00 (m, 7H), 1.43 (d, 3H). LCMS (M+H)$^+$: Higher Rf isomer m/z 505.2; Lower Rf isomer m/z=505.2.

Example 60

Step A

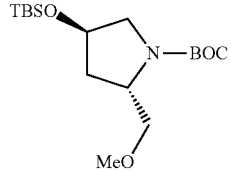 [SMILES: COC[C@@H]1C[C@@H](O[Si](C)(C)C(C)(C)C)CN1C(=O)OC(C)(C)C]

tert-Butyl (2S,4R)-4-{[tert-Butyl(dimethyl)silyl]oxy}-2-(methoxymethyl)-pyrrolidine-1-carboxylate Iodomethane (0.85 mL, 13.6 mmol) was added to a solution of tert-butyl (2S,4R)-4-{[tert-butyl(dimethyl)silyl]oxy}-2-(hydroxymethyl)pyrrolidine-1-carboxylate (1.50 g, 4.52 mmol) in dry DMF (15 mL) under nitrogen. Sodium hydride (0.22 g, 5.42 mmol, 60% dispersion in mineral oil) was added in portions and the mixture was stirred overnight at room temperature. The mixture was diluted with ethyl acetate. The organic layer was separated, washed twice with water and then brine, dried over MgSO$_4$, filtered and concentrated to give 1.51 g (96%) of methyl ether as a yellow oil. LC/MS (M-Boc+H)$^+$ m/z=246.2. $^1$H NMR (CDCl$_3$) δ 4.38 (m, 1H), 4.05 (m, 1H), 3.50 (m, 2H), 3.25-3.45 (m, 2H), 3.34 (s, 3H), 1.87-2.06 (m, 2H), 1.47 (s, 9H), 0.87 (s, 9H), 0.06 (s, 6H).

Step B

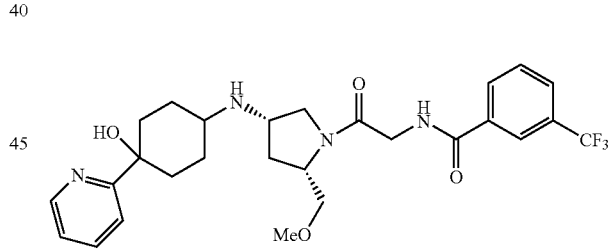

N-{2-[(2S,4S)-4-[(4-Hydroxy-4-pyridin-2-ylcyclohexyl)amino]-2-(methoxymethyl)pyrrolidin-1-yl]-2-oxoethyl}-3-(trifluoromethyl)benzamide The title compound was prepared from the intermediate of step A following the procedures described for Example 59. Higher Rf isomer: LCMS m/z=535.2 (M+H); $^1$H NMR (CDCl$_3$) δ 8.53 (d, 1H), 8.12 (s, 1H), 8.03 (d, 1H), 7.77 (m, 1H), 7.72 (m, 1H), 7.58 (t, 1H), 7.47 (m, 1H), 7.34 (m, 1H), 7.21 (m, 1H), 4.90 (m, 1H), 4.12-4.47 (m, 4H), 3.89 (dd, 1H), 3.79 (dd, 1H), 3.54 (m, 2H), 3.38 (s, 3H), 3.03 (m, 1H), 2.40 (m, 1H), 2.18 (m, 3H), 1.90 (m, 1H), 1.75 (m, 1H), 1.60 (m, 2H), 1.50 (m, 2H); $^{19}$F NMR (CDCl$_3$) δ −63.11 (s). Lower Rf isomer: LCMS (M+H)$^+$ m/z=535.2; $^1$HNMR (CDCl$_3$) δ 8.53 (d, 1H), 8.12 (s, 1H), 8.02 (d, 1H), 7.78 (m, 1H), 7.72 (m, 1H), 7.58 (t, 1H), 7.42 (m, 1H), 7.34 (m, 1H), 7.21 (m, 1H), 4.12-4.48 (m, 4H), 3.83 (m, 2H), 3.68 (m, 1H), 3.56 (m, 1H), 3.38 (s, 3H), 2.72 (m, 1H), 2.38 (m, 1H), 1.60-2.20 (m, 10H); $^{19}$F NMR (CDCl$_3$) δ −63.12 (s).

Example 61

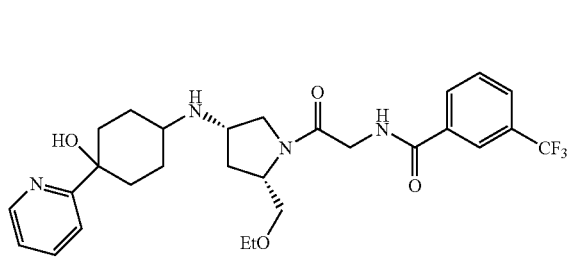 [SMILES: CCOC[C@@H]1C[C@H](NC2CCC(O)(c3ccccn3)CC2)CN1C(=O)CNC(=O)c1cccc(C(F)(F)F)c1]

N-(2-{(2S,4S)-2-(Ethoxymethyl)-4-[(4-hydroxy-4-pyridin-2-ylcyclohexyl)-amino]pyrrolidin-1-yl}-2-oxoethyl)-3-(trifluoromethyl)benzamide The title compound was prepared following the procedures described for Example 60. Higher Rf isomer: LCMS (M+H)$^+$ m/z=549.1; $^1$H NMR (CDCl$_3$) δ 8.51 (m, 1H), 8.10 (m, 1H), 7.99 (m, 1H), 7.70 (m, 2H), 7.32-7.60 (m, 3H), 7.18 (m, 1H), 4.03-4.47 (m, 3H), 3.22-3.91 (m, 5H), 3.04 (m, 1H), 1.70-2.47 (m, 7H), 1.51 (m, 4H), 1.21 (m, 4H).

Lower Rf isomer: LCMS (M+H)$^+$ m/z=549.1; $^1$H NMR (CDCl$_3$) δ 8.52 (m, 1H), 8.11 (m, 1H), 8.00 (m, 1H), 7.73 (m, 2H), 7.55 (m, 1H), 7.39 (m, 2H), 7.20 (m, 1H), 4.11-4.48 (m, 3H), 3.46-3.88 (m, 5H), 3.21 (m, 1H), 2.63 (m, 1H), 2.38 (m, 1H), 1.55-1.98 (m, 10H), 1.20 (m, 3H).

Example 62

Step A

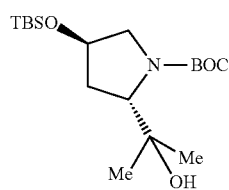 [SMILES: CC(C)(C)OC(=O)N1C[C@H](O[Si](C)(C)C(C)(C)C)C[C@H]1C(C)(C)O]

tert-Butyl (2S,4R)-4-{[tert-Butyl(dimethyl)silyl]oxy}-2-(1-hydroxy-1-methylethyl)pyrrolidine-1-carboxylate To a solution of 1-tert-butyl 2-methyl (2S,4R)-4-{[tert-butyl(dimethyl)silyl]oxy}pyrrolidine-1,2-dicarboxylate (1.00 g, 2.78 mmol) in dry THF (20 mL) at 0° C. was dropwise added methylmagnesium bromide solution (2.0 mL, 6.0 mmol, 3.0 M in ether) over 5 minutes. After stirring for four hours, the mixture was warmed to room temperature and quenched with NH$_4$Cl/H$_2$O and extracted twice with ethyl acetate. The organic extracts were dried over MgSO$_4$, filtered and concentrated to give 1.00 g (100%) of the title compound as a white solid. $^1$H NMR (CDCl$_3$) δ 5.85 (s, 1H), 4.25 (s, 1H), 4.08 (t, 1H), 3.67 (d, 1H), 3.18 (d, 1H), 1.94 (m, 1H), 1.60 (m, 1H), 1.45 (s, 9H), 1.15 (s, 3H), 1.05 (s, 3H), 0.87 (s, 9H), 0.06 (s, 6H).

Step B

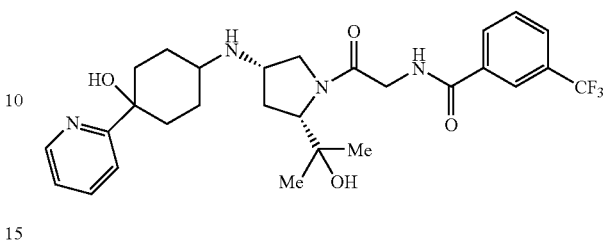

N-(2-{(2S,4S)-2-(1-Hydroxy-1-methylethyl)-4-[(trans-4-hydroxy-4-pyridin-2-ylcyclohexyl)amino]pyrrolidin-1-yl}-2-oxoethyl)-3-(trifluoromethyl)benzamide The title compound was prepared from the alcohol of step A following the procedures described for Example 59. Higher Rf isomer: LCMS (M+H)$^+$ m/z=549.3; $^1$H NMR (CDCl$_3$) δ 8.53 (m, 1H), 8.13 (s, 1H), 8.01 (d, 1H), 7.78 (d, 1H), 7.74 (t, 1H), 7.59 (t, 1H), 7.48 (d, 1H), 7.32 (m, 1H), 7.22 (m, 1H), 4.19-4.40 (m, 3H), 3.98 (dd, 1H), 3.49 (m, 2H), 3.29 (m, 1H), 3.08 (m, 1H), 2.10-2.45 (m, 8H), 1.71 (m, 2H), 1.24 (s, 3H), 1.21 (s, 3H); $^{19}$F NMR (CDCl$_3$) δ −63.12 (s). Lower Rf isomer: LCMS (M+H)$^+$ m/z=549.3; $^1$H NMR (CDCl$_3$) δ 8.52 (d, 1H), 8.12 (s, 1H), 8.01 (d, 1H), 7.77 (d, 1H), 7.73 (m, 1H), 7.59 (t, 1H), 7.40 (d, 1H), 7.37 (m, 1H), 7.22 (m, 1H), 5.14 (bs, 1H), 4.39 (m, 1H), 4.33 (m, 1H), 4.20 (m, 1H), 3.97 (m, 1H), 3.72 (m, 1H), 3.40 (m, 1H), 2.74 (m, 1H), 1.70-2.35 (m, 12H), 1.24 (s, 3H), 1.21 (s, 3H); $^{19}$F NMR (CDCl$_3$) δ −63.12 (s).

Example 63

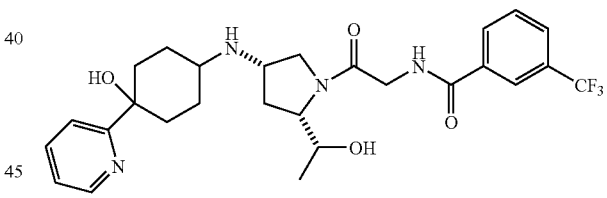

N-(2-{(2S,4S)-2-[1-Hydroxyethyl]-4-[(4-hydroxy-4-pyridin-2-ylcyclohexyl)-amino]pyrrolidin-1-yl}-2-oxoethyl)-3-(trifluoromethyl)benzamide The title compound was prepared in a manner similar to that for Example 62. MS (M+H)$^+$ 535.

Example 64

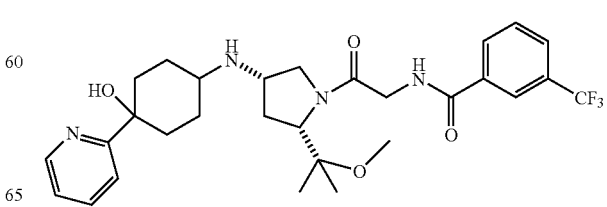

N-{2-[(2S,4S)-4-[(4-Hydroxy-4-pyridin-2-ylcyclohexyl)amino]-2-(1-methoxy-1-methylethyl)pyrrolidin-1-yl]-2-oxoethyl}-3-(trifluoromethyl)benzamide The title compound was prepared starting from tert-butyl (2S,4R)-4-{[tert-butyl(dimethyl)silyl]oxy}-2-(1-hydroxy-1-methylethyl)pyrrolidine-1-carboxylate following the procedures described for Example 60. Higher Rf isomer: LC/MS (M+H)+ m/z=563.3; $^1$H NMR (CDCl$_3$) δ 8.55 (m, 1H), 8.14 (m, 1H), 8.04 (m, 1H), 7.74 (m, 2H), 7.38-7.63 (m, 3H), 7.22 (m, 1H), 5.42-5.80 (bs, 1H), 4.84 (bs, 1H), 4.15-4.43 (m, 3H), 3.96 (m, 1H), 3.42 (m, 1H), 3.22 (m, 4H), 3.02 (m, 11-1), 1.89-2.34 (m, 6H), 1.46-1.67 (m, 4H), 1.22 (m, 6H). Lower Rf isomer: LC/MS (M+H)+ m/z=563.3; $^1$H NMR (CDCl$_3$) δ 8.53 (m, 1H), 8.15 (m, 1H), 8.03 (m, 1H), 7.74 (m, 2H), 7.35-7.61 (m, 3H), 7.22 (m, 1H), 3.87-4.43 (m, 4H), 3.50 (m, 1H), 3.21 (m, 4H), 2.64 (m, 1H), 2.27 (m, 1H), 1.67-1.98 (m, 9H), 1.22 (m, 6H).

Example 65

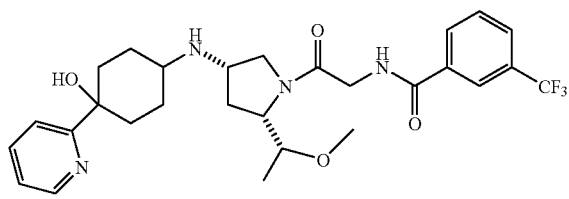

N-(2-{(2S,4S)-4-[(4-Hydroxy-4-pyridin-2-ylcyclohexyl)amino]-2-[(1S)-1-methoxyethyl]pyrrolidin-1-yl}-2-oxoethyl)-3-(trifluoromethyl)benzamide The title compound was prepared in a fashion similar to that for Example 64. MS (M+H)+ 549.

Example 66

Part A

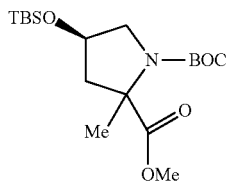 [SMILES: COC(=O)C1(C)C[C@@H](O[Si](C)(C)C(C)(C)C)CN1C(=O)OC(C)(C)C]

1-tert-Butyl 2-Methyl (4R)-4-{[tert-butyl(dimethyl)silyl]oxy}-2-methylpyrrolidine-1,2-dicarboxylate To a solution of 1-tert-butyl 2-methyl (2S,4R)-4-{[tert-butyl(dimethyl)silyl]oxy}pyrrolidine-1,2-dicarboxylate (5.11 g, 14.2 mmol) in dry THF (60 mL) at −78° C. was dropwise added lithium bistrimethylsilylamide (17.0 mL, 17.0 mmol, 1.0 M in THF). After being stirred for 30 minutes, iodomethane (1.77 mL, 28.4 mmol) was then added. The mixture was stirred at −78° C. for one hour, warmed to 0° C. for one hour and finally quenched with NaHCO$_3$/H$_2$O. The resulting mixture was extracted twice with ethyl acetate. The combined extracts were dried over MgSO$_4$, filtered and concentrated. The residue was chromatographed on silica gel eluting with hexane to 5% ethyl acetate/hexane to provide 2.66 g (50%) of a mixture of product isomers as a colorless oil. LC/MS (M-Boc+H)+ m/z=274.1. $^1$H NMR (CDCl$_3$) δ 4.38 (m, 1H), 3.71 (m, 4H), 3.36 (m, 1H), 1.84-2.35 (m, 2H), 1.61 (m, 3H), 1.44 (m, 9H), 0.88 (m, 9H), 0.07 (m, 6H).

Step B

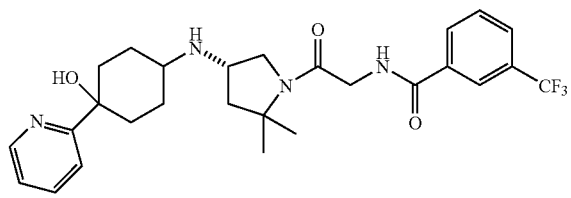

N-(2-{(4S)-4-[(4-Hydroxy-4-pyridin-2-ylcyclohexyl)amino]-2,2-dimethyl-pyrrolidin-1-yl}-2-oxoethyl)-3-(trifluoromethyl)benzamide The title compound was prepared from 1-tert-butyl 2-methyl (4R)-4-{[tert-butyl(dimethyl)silyl]oxy}-2-methylpyrrolidine-1,2-dicarboxylate following the procedures described for Example 59. Higher Rf isomer: LC/MS (M+H)+ m/z=519.2; $^1$H NMR (CD$_3$OD, bis-trifluoroacetate salt) δ 8.51 (m, 1H), 8.18 (m, 2H), 7.63-7.90 (m, 4H), 7.27 (m, 1H), 4.15 (dd, 2H), 3.98 (m, 1H), 3.55 (m, 1H), 3.28 (m, 2H), 2.92 (m, 1H), 2.38 (m, 2H), 1.96-2.20 (m, 3H), 1.50-1.79 (m, 7H), 1.42 (s, 3H). Lower Rf isomer: LC/MS (M+H)+ m/z=519.2; $^1$H NMR (CD$_3$OD, bis-trifluoroacetate salt) δ 8.49 (m, 1H), 8.21 (m, 1H), 8.14 (m, 1H), 7.65-7.90 (m, 4H), 7.25 (m, 1H), 4.10 (m, 3H), 3.72 (m, 1H), 3.28 (m, 2H), 2.73 (m, 1H), 2.10 (m, 3H), 1.82 (m, 2H), 1.73 (m, 4H), 1.58 (s, 3H), 1.45 (s, 3H).

Example 67

Step A

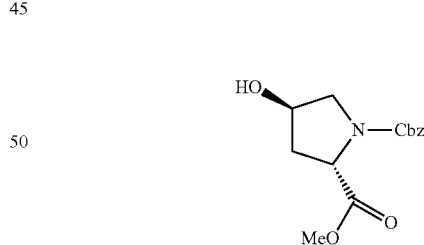

1-Benzyl 2-Methyl (2S,4R)-4-hydroxypyrrolidine-1,2-dicarboxylate

L-trans-4-Hydroxyproline methyl ester hydrochloride (9.70 g, 54.0 mmol) was dissolved in dry THF (180 mL) and triethylamine (7.53 mL, 54.0 mmol). N-(Benzyloxycarbonyloxy)succinimide (13.5 g, 54.0 mmol) dissolved in THF (70 mL) was slowly added to the solution. After stirring at room temperature overnight, the mixture was diluted with ethyl acetate and the organic layer was washed successively with water and brine. The organic extracts were dried over Na$_2$SO$_4$, filtered, and concentrated. The residue was chromatographed on silica gel (30% to 70% ethyl acetate/hexane) to provide 12.8 g (85%) of desired product as a colorless oil. LC/MS (M+H)$^+$ m/z=280.0; $^1$H NMR (CDCl$_3$) δ 7.33 (m, 5H), 5.00-5.25 (m, 21-1), 4.52 (m, 2H), 3.69 (m, 2H), 3.56 and 3.78 (s, 3H), 2.05-2.40 (m, 2H).

Step B

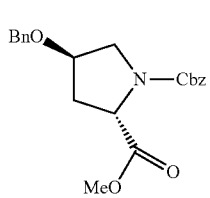 [SMILES: COC(=O)[C@@H]1C[C@@H](OCc2ccccc2)CN1C(=O)OCc1ccccc1]

1-Benzyl 2-Methyl (2S,4R)-4-(benzyloxy)pyrrolidine-1,2-dicarboxylate

1-Benzyl 2-methyl (2S,4R)-4-hydroxypyrrolidine-1,2-dicarboxylate (6.60 g, 23.6 mmol) was dissolved in dry THF (100 mL) and cooled to 0° C. under nitrogen. Sodium hydride (1.04 g, 26.0 mmol, 60% dispersion in mineral oil) was added in portions and the mixture was stirred for 15 minutes. Tetra-n-butylammonium iodide (0.40 g, 1.0 mmol) and benzyl bromide (3.15 mL, 26.0 mmol) were added and the mixture stirred for one hour at 0° C. and then one hour at room temperature. The mixture was diluted with ethyl acetate. The organic layer was washed with water and then brine, dried over MgSO$_4$, filtered, and concentrated. The residue was chromatographed on silica gel (20% to 50% ethyl acetate/hexane) to give 4.21 g (48%) of benzyl ether. LC/MS (M+H)$^+$ m/z=370.2; $^1$H NMR (CDCl$_3$) δ 7.34 (m, 10H), 5.13 (m, 2H), 4.51 (m, 3H), 4.20 (m, 1H), 3.68 (m, 2H), 3.54 and 3.78 (s, 3H), 2.45 (m, 1H), 2.11 (m, 1H).

Step C

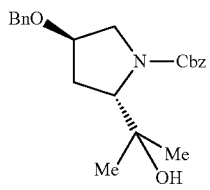 [SMILES: CC(C)(O)[C@@H]1C[C@@H](OCc2ccccc2)CN1C(=O)OCc1ccccc1]

Benzyl (2S,4R)-4-(Benzyloxy)-2-(1-hydroxy-1-methylethyl)pyrrolidine-1-carboxylate 1-Benzyl 2-methyl (2S,4R)-4-(benzyloxy)pyrrolidine-1,2-dicarboxylate (4.21 g, 11.4 mmol) was dissolved in dry THF (20 mL) under nitrogen and cooled to 0° C. Methylmagnesium bromide solution (8.4 mL, 25 mmol, 3.0 M in ether) was added dropwise. After stirring for twelve hours at 0° C., the mixture was warmed to room temperature and quenched with NH$_4$Cl/H$_2$O and extracted twice with ethyl acetate. The organic extracts were washed with brine, dried over Na$_2$SO$_4$, filtered and concentrated. The residue was chromatographed on silica gel (20% to 30% ethyl acetate/hexane) to give 2.47 g (59%) of the alcohol as a viscous oil. LC/MS (M+H)$^+$ m/z=370.1; $^1$H NMR (CDCl$_3$) δ 7.33 (m, 10H), 5.55 (bs, 1H), 5.20 (s, 2H), 4.50 (s, 2H), 4.19 (m, 1H), 4.05 (m, 2H), 3.31 (m, 1H), 2.27 (m, 1H), 1.73 (m, 1H), 1.21 (s, 3H), 1.13 (s, 3H).

Step D

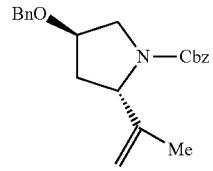 [SMILES: C=C(C)[C@@H]1C[C@@H](OCc2ccccc2)CN1C(=O)OCc1ccccc1]

Benzyl (2S,4R)-4-(Benzyloxy)-2-isopropenylpyrrolidine-1-carboxylate

Benzyl (2S,4R)-4-(benzyloxy)-2-(1-hydroxy-1-methylethyl)pyrrolidine-1-carboxylate (2.22 g, 6.01 mmol) was dissolved in toluene (40 mL) and triethylamine (10.0 mL, 72 mmol) under nitrogen. The mixture was cooled to −50° C. and thionyl chloride (0.44 mL, 6.0 mmol) was added dropwise. After stirring for three hours at −30° C., the mixture was quenched by addition of water. The resulting mixture was extracted twice with ethyl acetate and the organic extracts were washed with brine, dried over Na$_2$SO$_4$, filtered and concentrated. The residue was chromatographed on silica gel (10% to 20% ethyl acetate/hexane) to give 1.10 g (52%) of the olefin as a pale yellow oil. LC/MS (M+H)$^+$ m/z=352.2; $^1$H NMR (CDCl$_3$) δ 7.35 (m, 10H), 5.16 (m, 2H), 4.84 (m, 2H), 4.52 (m, 3H), 4.16 (m, 1H), 3.87 (m, 1H), 3.58 (m, 1H), 2.29 (m, 1H), 1.94 (m, 1H), 1.69 (m, 3H).

Step E

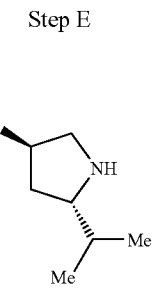

(2S,4R)-4-(Benzyloxy)-2-isopropylpyrrolidine

Benzyl (2S,4R)-4-(benzyloxy)-2-isopropenylpyrrolidine-1-carboxylate (1.00 g, 2.84 mmol) was dissolved in ethanol (40 mL) and then 5% Pd—C (100 mg) was added to the solution. The flask was purged with hydrogen and then shaken on a Parr under 53 psi atmosphere of hydrogen for 17 hours. The reaction was then flushed with nitrogen and filtered through Celite on a glass frit and washed with methanol. The filtrate was concentrated and chromatographed on silica gel (1% triethylamine/10% methanol/89% ethyl acetate) to furnish the amine as a pale yellow oil, 0.53 g (85%). LC/MS (M+H)$^+$ m/z=220.2; $^1$H NMR (CDCl$_3$) δ 7.33 (m, 5H), 4.49

(m, 2H), 4.12 (m, 1H), 3.19 (dd, 1H), 3.00 (m, 2H), 2.05 (m, 1H), 1.96 (bs, 1H), 1.49 (m, 2H), 1.00 (d, 3H), 0.91 (d, 3H).

Step F

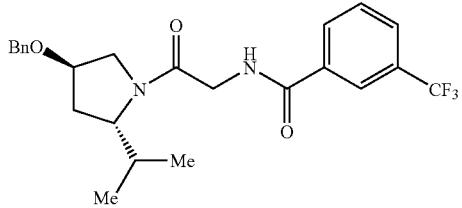 [SMILES: CC(C)[C@@H]1C[C@@H](OCc2ccccc2)CN1C(=O)CNC(=O)c1cccc(C(F)(F)F)c1]

N-{2-[(2S,4R)-4-Benzyloxy-2-isopropylpyrrolidin-1-yl]-2-oxoethyl}-3-(trifluoromethyl)benzamide (2S,4R)-4-(Benzyloxy)-2-isopropylpyrrolidine (0.410 g, 1.90 mmol) was dissolved in dichloromethane (30 mL) under nitrogen. (3-Trifluoromethyl-benzoylamino)-acetic acid (0.462 g, 1.90 mmol) was added followed by EDC (0.394 g, 2.06 mmol) and the mixture was stirred at room temperature-overnight. LC/MS revealed the reaction was not yet complete. More (3-Trifluoromethyl-benzoylamino)-acetic acid (0.12 g, 0.48 mmoles) and more EDC (0.30 g, 1.6 mmoles) were added and stirring continued for 3 hours at room temperature, then at reflux for 1.5 hours. The mixture was chromatographed on silica gel eluting with 30% ethyl acetate/hexane to provide 0.66 g (79%) of the coupled product as a colorless oil. LC/MS (M+H)+ m/z=449.2; 1H NMR (CDCl3) δ 8.03 (m, 1H), 7.76 (m, 1H), 7.58 (m, 2H), 7.34 (m, 5H), 4.52 (m, 2H), 4.03-4.34 (m, 4H), 3.65 (m, 1H), 3.48 (m, 1H), 2.54 (m, 1H), 2.12 (m, 1H), 1.92 (m, 1H), 0.92 (d, 3H), 0.77 (d, 3H).

Step G

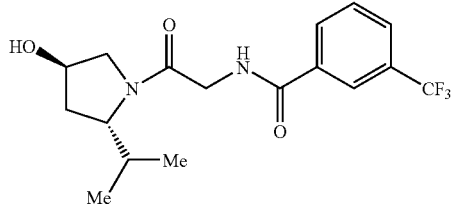 [SMILES: CC(C)[C@@H]1C[C@@H](O)CN1C(=O)CNC(=O)c1cccc(C(F)(F)F)c1]

N-{2-[(2S,4R)-4-Hydroxy-2-isopropylpyrrolidin-1-yl]-2-oxoethyl}-3-(trifluoromethyl)benzamide N-{2-[(2S,4R)-4-Benzyloxy-2-isopropylpyrrolidin-1-yl]-2-oxoethyl}-3-(trifluoromethyl)benzamide (0.630 g, 1.40 mmol) was dissolved in methanol (60 mL) and then palladium hydroxide (90 mg) was added to the solution. The flask was purged with hydrogen and then stirred under an atmosphere of hydrogen using a balloon. After three hours, TLC indicated complete consumption of starting material. The reaction was then flushed with nitrogen and filtered through Celite on a glass frit and washed with methanol. The filtrate was concentrated to give the desired alcohol as a white solid, 0.52 g (100%). LC/MS (M+H)+ m/z=359.2; 1H NMR (CDCl3) δ 8.11 (m, 2H), 7.53-7.82 (m, 3H), 4.04-4.52 (m, 4H), 3.63 (m, 1H), 3.43 (m, 1H), 2.50 (m, 1H), 1.86-2.25 (m, 2H), 0.89 (d, 3H), 0.78 (d, 3H).

Step H

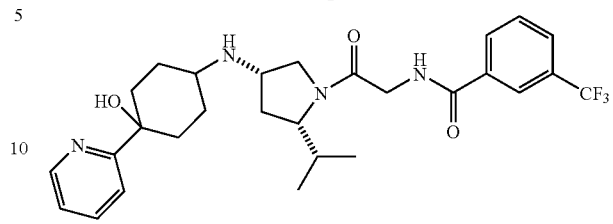

N-(2-{(2S,4S)-4-[(4-Hydroxy-4-pyridin-2-ylcyclohexyl)amino]-2-isopropyl-pyrrolidin-1-yl}-2-oxoethyl)-3-(trifluoromethyl)benzamide The title compound was prepared from the above intermediate following the procedures described for Example 59. Higher Rf isomer: LC/MS (M+H)+ m/z=533.3; 1H NMR (CD3OD, bis-trifluoroacetate salt) δ 8.66 (m, 1H), 8.20 (m, 3H), 7.94 (m, 2H), 7.74 (m, 1H), 7.59 (m, 1H), 4.36 (m, 2H), 4.06-4.27 (m, 2H), 4.00 (m, 1H), 3.63 (m, 1H), 3.46 (m, 1H), 2.63 (m, 1H), 2.50 (m, 1H), 2.34 (m, 4H), 1.76-2.05 (m, 5H), 0.96 (d, 3H), 0.93 (d, 3H); Lower Rf isomer: LC/MS (M+H)+ m/z=533.2; 1H NMR (CD3OD, bis-trifluoroacetate salt) δ 8.66 (m, 1H), 8.24 (m, 3H), 7.96 (m, 2H), 7.72 (m, 2H), 4.00-4.42 (m, 5H), 3.45 (m, 2H), 2.65 (m, 1H), 2.49 (m, 1H), 2.22 (m, 4H), 1.95 (m, 5H), 0.96 (d, 3H), 0.91 (d, 3H).

The following Examples 68-71 were prepared in a manner similar to Example 67.

Example 68

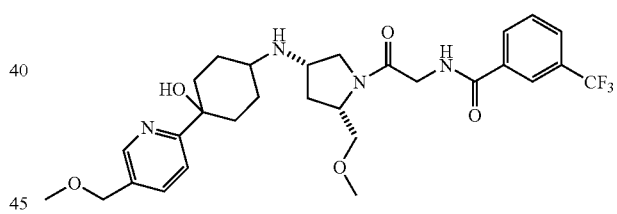

N-{2-[(2S,4S)-4-({4-Hydroxy-4-[5-(methoxymethyl)pyridin-2-yl]cyclohexyl}-amino)-2-(methoxymethyl)pyrrolidin-1-yl]-2-oxoethyl}-3-(trifluoromethyl)benzamide

MS (M+H)+ 579.

Example 69

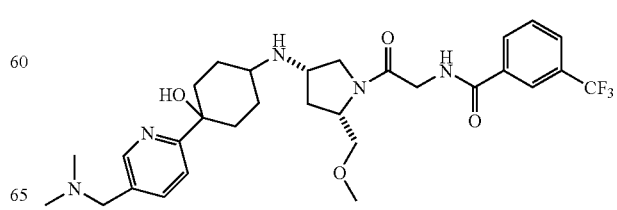

N-{2-[(2S,4S)-4-[(4-{5-[(Dimethylamino)methyl]pyridin-2-yl}-4-hydroxy-cyclohexyl)amino]-2-(methoxymethyl)pyrrolidin-1-yl]-2-oxoethyl}-3-(trifluoromethyl)benzamide

MS (M+H)+ 592.

Example 70

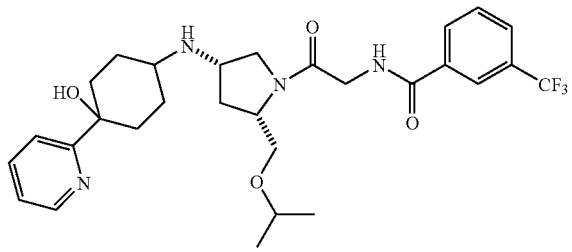 [SMILES: CC(C)OC[C@@H]1C[C@H](NC2CCC(O)(c3ccccn3)CC2)CN1C(=O)CNC(=O)c1cccc(C(F)(F)F)c1]

N-{2-[(2S,4S)-4-[(4-Hydroxy-4-pyridin-2-ylcyclohexyl)amino]-2-(isopropoxy-methyl)pyrrolidin-1-yl]-2-oxoethyl}-3-(trifluoromethyl)benzamide

MS (M+H)+ 563.

Example 71

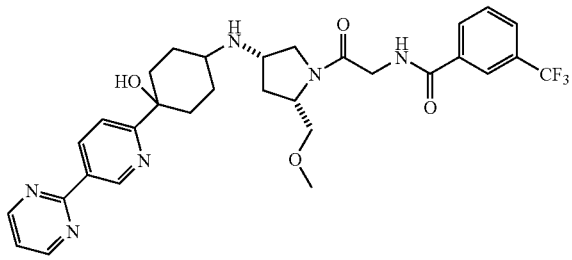 [SMILES: COC[C@@H]1C[C@H](NC2CCC(O)(c3ccc(-c4ncccn4)cn3)CC2)CN1C(=O)CNC(=O)c1cccc(C(F)(F)F)c1]

N-{2-[(2S,4S)-4-{[4-Hydroxy-4-(5-pyrimidin-2-ylpyridin-2-yl)cyclohexyl]amino}-2-(methoxymethyl)pyrrolidin-1-yl]-2-oxoethyl}-3-(trifluoromethyl)benzamide

MS (M+H) 613.3.

Example 72

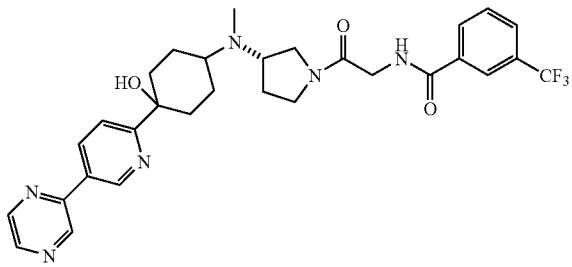 [SMILES: CN(C1CCC(O)(c2ccc(-c3cnccn3)cn2)CC1)[C@H]1CCN(C(=O)CNC(=O)c2cccc(C(F)(F)F)c2)C1]

N-(2-{(3S)-3-[[4-Hydroxy-4-(5-pyrazin-2-ylpyridin-2-yl)cyclohexyl](methyl)amino]pyrrolidin-1-yl}-2-oxoethyl)-3-(trifluoromethyl)benzamide N-[2-((3S)-3-{[4-Hydroxy-4-(5-pyrazin-2-ylpyridin-2-yl)cyclohexyl]amino}pyrrolidin-1-yl)-2-oxoethyl]-3-(trifluoromethyl)benzamide (29.0 mg, 0.051 mmol) and 37% aqueous formaldehyde (21 uL, 0.26 mmol) were dissolved in THF (1.0 mL). The mixture was evaporated to dryness. Then the residue was taken up in THF (1 mL) and sodium triacetoxyborohydride (24 mg, 0.11 mmol) was added. After being stirred at room temperature overnight, the mixture was purified by HPLC to provide the title compound (5.9 mg). MS (M+H) 583.3.

Example 73

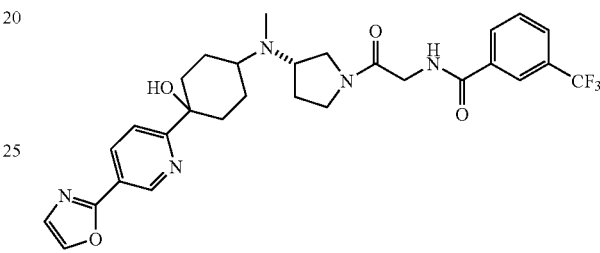

N-(2-{(3S)-3-[{4-Hydroxy-4-[5-(1,3-oxazol-2-yl)pyridin-2-yl]cyclohexyl}(methyl)amino]pyrrolidin-1-yl}-2-oxoethyl)-3-(trifluoromethyl)benzamide N-{2-[(3S)-3-({4-Hydroxy-4-[5-(1,3-oxazol-2-yl)pyridin-2-yl]cyclohexyl}amino)pyrrolidin-1-yl]-2-oxoethyl}-3-(trifluoromethyl)benzamide (45 mg, 0.081 mmol) and 37% aqueous formaldehyde (30 mg, 1.0 mmol) were dissolved in methylene chloride (5.6 mL). The mixture was evaporated to dryness. Then the residue was taken up in THF (1 mL) and sodium triacetoxyborohydride (38 mg, 0.18 mmol) was added. After being stirred at room temperature overnight, the mixture was purified by HPLC to provide the title compound (27 mg). MS (M+H) 572.3.

Example 74

Step A

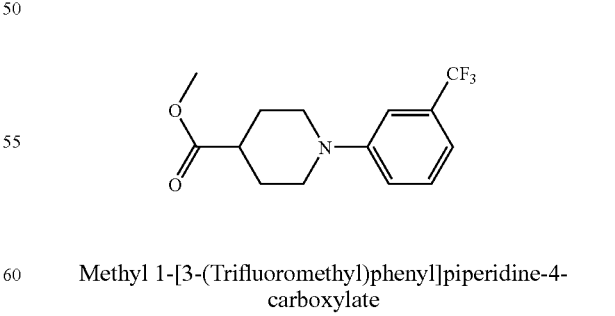

Methyl 1-[3-(Trifluoromethyl)phenyl]piperidine-4-carboxylate

Methyl piperidine-4-carboxylate (2.0 g, 14 mmol), 1-bromo-3-(trifluoromethyl)benzene (1.5 g, 6.8 mmol), and potassium tert-butoxide (0.76 g, 6.8 mmol) in a mixed solvent of toluene (20 mL) and DMF (4 mL) was added [1,1'-bis(diphenylphosphino)ferrocene]dichloropalladium(II), complex with dichloromethane (1:1) (0.3 g, 0.4 mmol) under nitrogen. The mixture was heated at 130° C. in an oil bath overnight. After cooling to room temperature, the mixture was filtered through celite and diluted with EtOAc. The resulting solution was washed with saturated NaHCO₃. The aqueous layer was extracted with EtOAc twice. The combined organic layers were dried (MgSO₄), concentrated and flash chromatographed with EtOAc/hexanes (20% to 40%) to give 0.90 g of product. MS (M+H) 288.2.

Step B

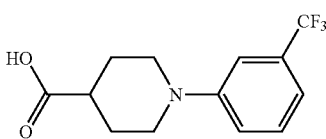 [SMILES: O=C(O)C1CCN(c2cccc(C(F)(F)F)c2)CC1]

1-[3-(Trifluoromethyl)phenyl]piperidine-4-carboxylic Acid

Methyl 1-[3-(trifluoromethyl)phenyl]piperidine-4-carboxylate (0.9 g, 3 mmol) was treated with the mixture of 2 M of sodium hydroxide in water (10 mL), THF (10 mL) and methanol (10 mL) at 50° C. for 1 h. After being neutralized with concentrated HCl (pH=3), the solution was concentrated. The resulting residue was azeotropically treated with benzene for 3 times to give the title compound which was used for the next reaction without purification. MS (M+H) 274.1.

Step C

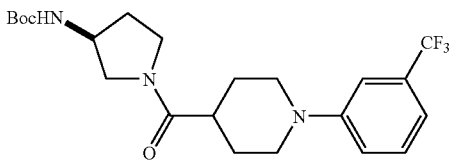 [SMILES: CC(C)(C)OC(=O)N[C@H]1CCN(C(=O)C2CCN(c3cccc(C(F)(F)F)c3)CC2)C1]

tert-Butyl [(3S)-1-({1-[3-(Trifluoromethyl)phenyl]piperidin-4-yl}carbonyl)pyrrolidin-3-yl]carbamate tert-Butyl (3S)-pyrrolidin-3-ylcarbamate (0.65 g, 3.5 mmol), 1-[3-(trifluoromethyl)phenyl]piperidine-4-carboxylic acid (0.80 g, 2.9 mmol), triethylamine (0.82 mL, 5.8 mmol) and benzotriazol-1-yloxytris(dimethylamino)phosphonium hexafluorophosphate (1.4 g, 3.2 mmol) were mixed in dry methylene chloride (10 mL). After being stirred overnight, the reaction mixture was diluted with EtOAc and washed with saturated NaHCO₃. The aqueous layer was extracted with EtOAc three times. The combined organic layers were dried (MgSO₄), concentrated and flash chromatographed (20% EtOAc/hexanes to 40% EtOAc/hexanes) to give 0.975 g of the desired product. MS (M+H) 442.1.

Step D

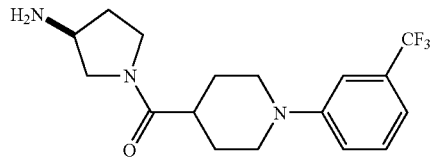 [SMILES: N[C@H]1CCN(C(=O)C2CCN(c3cccc(C(F)(F)F)c3)CC2)C1]

(3S)-1-({1-[3-(Trifluoromethyl)phenyl]piperidin-4-yl}carbonyl)pyrrolidin-3-amine bis(trifluoroacetate)

tert-Butyl [(3S)-1-({1-[3-(trifluoromethyl)phenyl]piperidin-4-yl}carbamate (0.975 g, 2.21 mmol) was treated with trifluoroacetic acid (5 mL) and methylene chloride (5 mL) for 1 h at room temperature. The solution was concentrated to give 1.75 g of product which was used for the next step without purification.

Step E

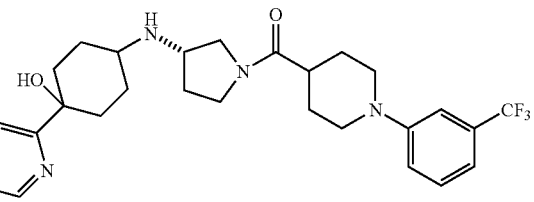

1-Pyridin-2-yl-4-{[(3S)-1-({1-[3-(trifluoromethyl)phenyl]piperidin-4-yl}carbonyl)pyrrolidin-3-yl]amino}cyclohexanol (3S)-1-({1-[3-(Trifluoromethyl)phenyl]piperidin-4-yl}carbonyl)pyrrolidin-3-amine bis(trifluoroacetate) (110 mg, 0.20 mmol), 4-hydroxy-4-pyridin-2-yl-cyclohexanone (45 mg, 0.24 mmol), triethylamine (0.082 mL, 0.59 mmol), and sodium triacetoxyborohydride (83 mg, 0.39 mmol) were mixed in methylene chloride (6 mL). After being stirred overnight, the reaction mixture was diluted with EtOAc and washed with saturated Na₂CO₃. The aqueous layer was extracted with EtOAc three times. The combined organic layers were dried (MgSO₄), concentrated and purified by silica gel column (EtOAc to 1% Et₃N/EtOAc to 5% Et₃N/EtOAc) to provide the title compound. LCMS (M+H)=517.2.

Example 75

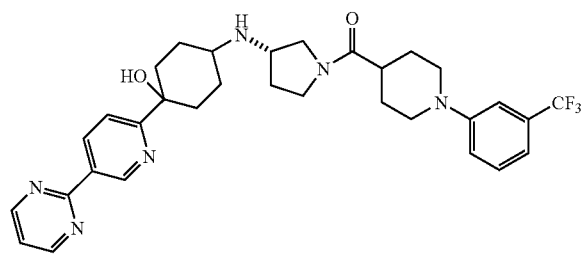

1-(5-pyrimidin-2-ylpyridin-2-yl)-4-{[(3S)-1-({1-[3-(trifluoromethyl)phenyl]piperidin-4-yl}carbonyl)pyrrolidin-3-yl]amino}cyclohexanol The title compound was prepared in a manner analogous to that described for Example 74. MS (M+H) 595.2.

Example 76

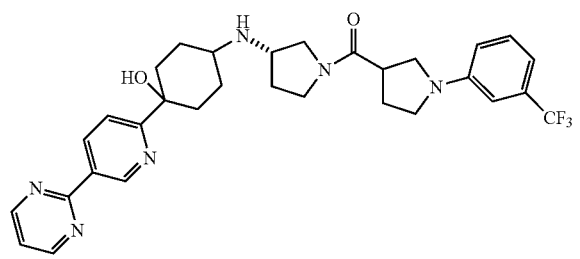

1-(5-Pyrimidin-2-ylpyridin-2-yl)-4-{[(3S)-1-({1-[3-(trifluoromethyl)phenyl]pyrrolidin-3-yl}carbonyl)pyrrolidin-3-yl]amino}cyclohexanol The title compound was prepared in a manner analogous to that described for Example 74. MS (M+H) 581.2.

Example 77

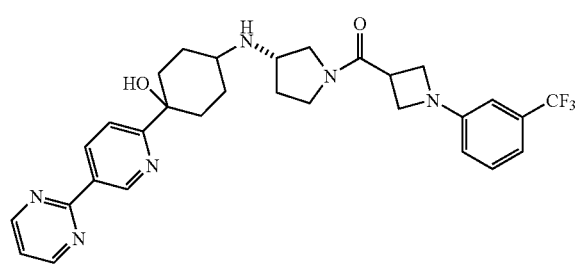

1-(5-Pyrimidin-2-ylpyridin-2-yl)-4-{[(3S)-1-({1-[3-(trifluoromethyl)phenyl]azetidin-3-yl}carbonyl)pyrrolidin-3-yl]amino}cyclohexanol The title compound was prepared in a manner analogous to that described for Example 74. MS (M+H) 567.2.

Example 78

Step A

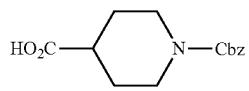

1-[(Benzyloxy)carbonyl]piperidine-4-carboxylic acid

Triethylamine (8.1 mL, 58 mmol) was added to a solution of piperidine-4-carboxylic acid (5 g, 40 mmol) and benzyl chloroformate (7.9 g, 46 mmol) in dichloromethane (100 mL) in an ice-water bath. After being stirred overnight, the solution was washed with concentrated HCl and brine, dried over Na₂SO₄ and concentrated. Chromatography on silica gel gave the title compound (10 g) as an oil. MS (M+H) 264.2.

Step B

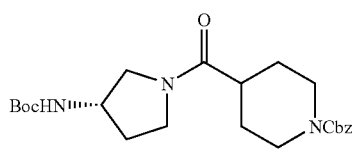 [SMILES: CC(C)(C)OC(=O)N[C@H]1CCN(C(=O)C2CCN(C(=O)OCc3ccccc3)CC2)C1]

Benzyl 4-({(3S)-3-[(tert-Butoxycarbonyl)amino]pyrrolidin-1-yl}carbonyl)piperidine-1-carboxylate A mixture of 1-[(benzyloxy)carbonyl]piperidine-4-carboxylic acid (5 g, 20 mmol), tert-butyl (3S)-pyrrolidin-3-ylcarbamate (3.9 g, 21 mmol), benzotriazol-1-yloxytris(dimethylamino)phosphonium hexafluorophosphate (9.2 g, 21 mmol), and triethylamine (3.8 g, 38 mmol) in dichloromethane (100 mL) was stirred at room temperature overnight. The reaction solution was washed with water, dried over Na₂SO₄, and concentrated. The residue was chromatographed on silica gel to give 7.5 g of product. MS (M+H) 432.2.

Step C

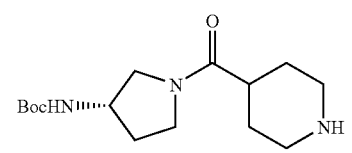 [SMILES: CC(C)(C)OC(=O)N[C@H]1CCN(C(=O)C2CCNCC2)C1]

tert-Butyl [(3S)-1-(Piperidin-4-ylcarbonyl)pyrrolidin-3-yl]carbamate

A mixture of benzyl 4-({(3S)-3-[(tert-butoxycarbonyl)amino]pyrrolidin-1-yl}carbonyl)piperidine-1-carboxylate (7.5 g, 17 mmol) and palladium on carbon (800 mg, 8 mmol) in methanol (100 mL) was shaken under hydrogen at 50 psi overnight. The mixture was filtered through celite and the filtrate was concentrated to give 5.1 g of product as a white solid. MS (M+H) 298.2.

Step D

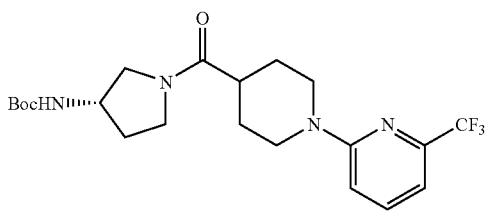 [SMILES: CC(C)(C)OC(=O)N[C@H]1CCN(C(=O)C2CCN(c3cccc(C(F)(F)F)n3)CC2)C1]

tert-Butyl [(3S)-1-({1-[6-(Trifluoromethyl)pyridin-2-yl]piperidin-4-yl}carbonyl)pyrrolidin-3-yl]carbamate A solution of 2-chloro-6-(trifluoromethyl)pyridine (1.8 g, 9.9 mmol), tert-butyl [(3S)-1-(piperidin-4-ylcarbonyl)pyrrolidin-3-yl]carbamate (2.97 g, 10.0 mmol) and triethylamine (4.1 mL, 30 mmol) in DMF (50 mL) was heated at 100° C. for 4 hrs. After cooling down, ethyl acetate was added. The resulting solution was washed with brine several times, dried over Na$_2$SO$_4$ and concentrated. The residue was chromatographed on silica gel to give the title compound (1.3 g) as a yellow solid. MS (M+H) 443.2.

Step E

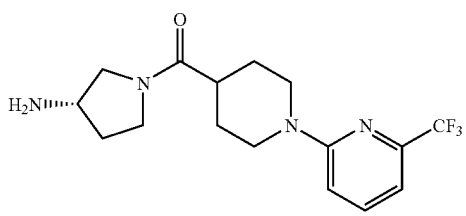 [SMILES: N[C@H]1CCN(C(=O)C2CCN(c3cccc(C(F)(F)F)n3)CC2)C1]

(3S)-1-({-[6-(Trifluoromethyl)pyridin-2-yl]piperidin-4-yl}carbonyl)pyrrolidin-3-amine tert-Butyl [(3S)-1-({1-[6-(trifluoromethyl)pyridin-2-yl]piperidin-4-yl}carbonyl)pyrrolidin-3-yl]carbamate (1.3 g, 2.9 mmol) was dissolved in a 4 M solution of HCl in 1,4-dioxane (10 mL). After being stirred at room temperature for 1 hr, the solution was concentrated to give the desired product as HCl salt (0.6 g). MS (M+H) 343.1.

Step F

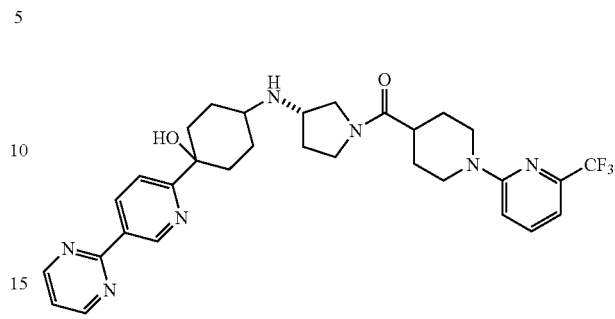

1-(5-Pyrimidin-2-ylpyridin-2-yl)-4-{[(3S)-1-({1-[6-(trifluoromethyl)pyridin-2-yl]piperidin-4-yl}carbonyl)pyrrolidin-3-yl]amino}cyclohexanol A solution of (3S)-1-({1-[6-(trifluoromethyl)pyridin-2-yl]piperidin-4-yl}carbonyl)pyrrolidin-3-amine (40 mg, 0.1 mmol), 4-hydroxy-4-(5-pyrimidin-2-ylpyridin-2-yl)cyclohexanone (47 mg, 0.18 mmol), sodium triacetoxyborohydride (50 mg, 0.23 mmol), and triethylamine (35 mg, 0.35 mmol) in dichloromethane (10 mL) was stirred at room temperature overnight. The reaction mixture was passed through a silica gel pad. The filtrate was concentrated and purified by HPLC to give the cis- and trans-isomers. MS (M+H) 596.2 for both isomers.

The following examples were prepared in a manner analogous to that for Example 78.

Example 79

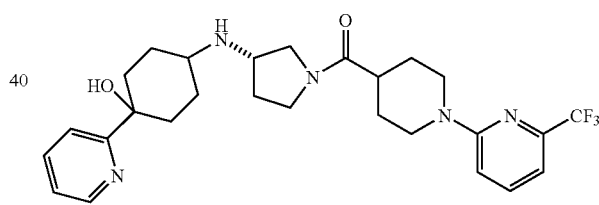

1-Pyridin-2-yl-4-{[(3S)-1-({1-[6-(trifluoromethyl)pyridin-2-yl]piperidin-4-yl}carbonyl)pyrrolidin-3-yl]amino}cyclohexanol

MS (M+H) 518.2.

Example 80

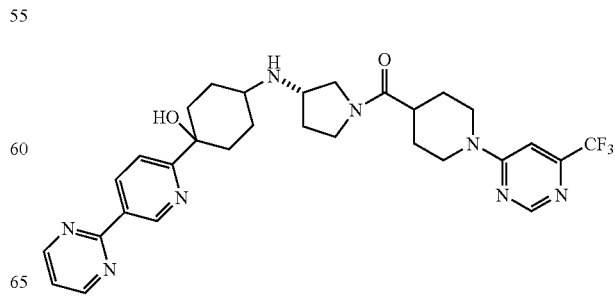

105

1-(6-Pyrimidin-2-ylpyridin-3-yl)-4-{[(3S)-1-({1-[6-(trifluoromethyl)pyrimidin-4-yl]piperidin-4-yl}carbonyl)pyrrolidin-3-yl]amino}cyclohexanol

MS (M+H) 597.3.

Example 81

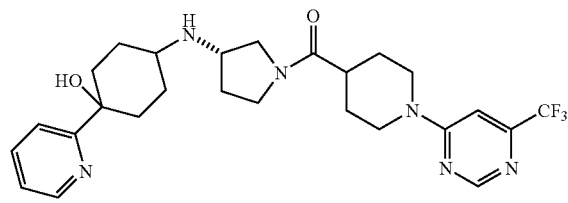

1-Pyridin-2-yl-4-{[(3S)-1-({1-[6-(trifluoromethyl)pyrimidin-4-yl]piperidin-4-yl}carbonyl)pyrrolidin-3-yl]amino}cyclohexanol

MS (M+H) 51.9.2.

Example 82

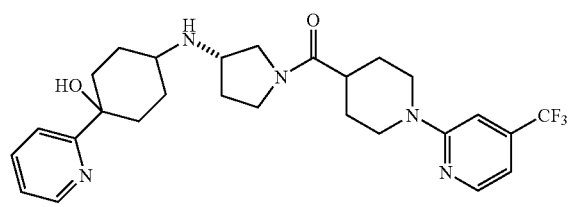

1-Pyridin-2-yl-4-{[(3S)-1-({1-[4-(trifluoromethyl)pyridin-2-yl]piperidin-4-yl}carbonyl)pyrrolidin-3-yl]amino}cyclohexanol

MS (M+H) 518.2.

Example 83

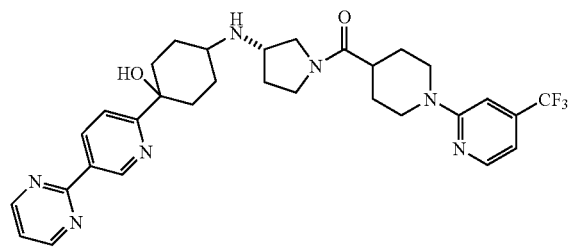

106

1-(5-Pyrimidin-2-ylpyridin-2-yl)-4-{[(3S)-1-({1-[4-(trifluoromethyl)pyridin-2-yl]piperidin-4-yl}carbonyl)pyrrolidin-3-yl]amino}cyclohexanol

MS (M+H) 596.2.

Example 84

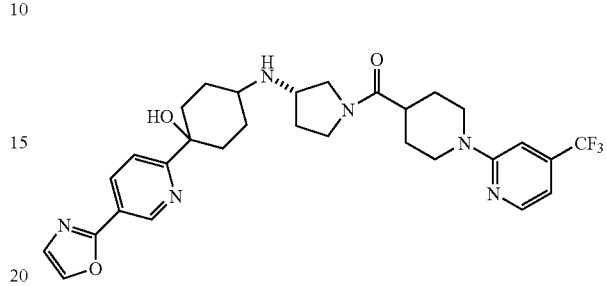

1-[5-(1,3-Oxazol-2-yl)pyridin-2-yl]-4-{[(3S)-1-({1-[4-(trifluoromethyl)pyridin-2-yl]piperidin-4-yl}carbonyl)pyrrolidin-3-yl]amino}cyclohexanol

MS (M+H) 584.2.

Example 85

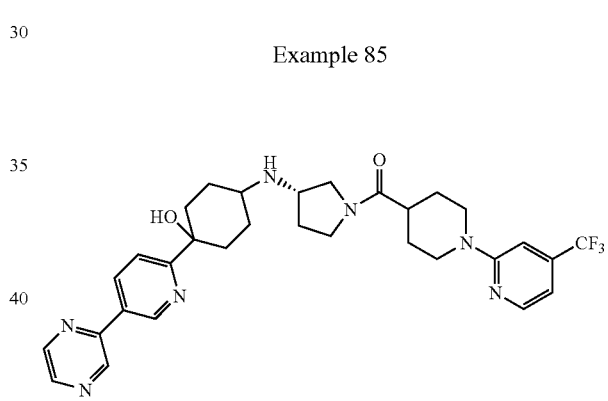

1-(5-Pyrazin-2-ylpyridin-2-yl)-4-{[(3S)-1-({1-[4-(trifluoromethyl)pyridin-2-yl]piperidin-4-yl}carbonyl)pyrrolidin-3-yl]amino}cyclohexanol

MS (M+H) 596.2.

Example 86

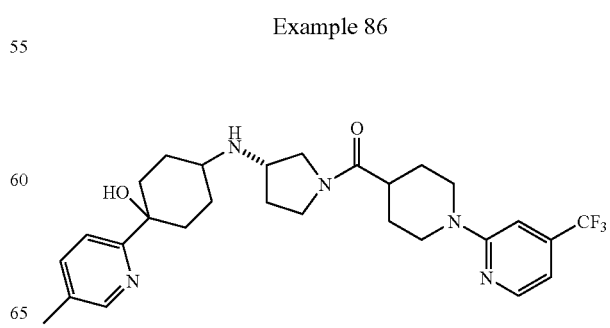

107

1-(5-Methylpyridin-2-yl)-4-{[(3S)-1-({1-[4-(trifluoromethyl)pyridin-2-yl]piperidin-4-yl}carbonyl)pyrrolidin-3-yl]amino}cyclohexanol

MS (M+H) 532.2.

Example 87

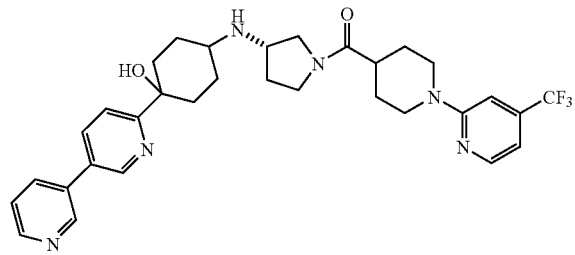

1-(3,3'-Bipyridin-6-yl)-4-{[(3S)-1-({1-[4-(trifluoromethyl)pyridin-2-yl]piperidin-4-yl}carbonyl)pyrrolidin-3-yl]amino}cyclohexanol

MS (M+H) 595.3.

Example 88

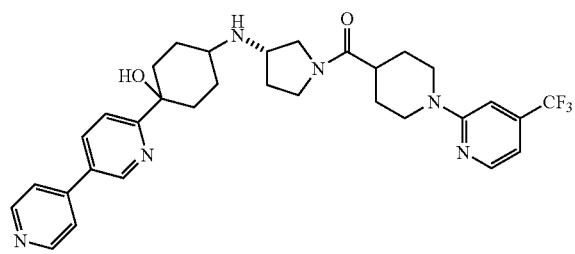

1-(3,4'-Bipyridin-6-yl)-4-{[(3S)-1-({1-[4-(trifluoromethyl)pyridin-2-yl]piperidin-4-yl}carbonyl)pyrrolidin-3-yl]amino}cyclohexanol

MS (M+H) 595.3.

Example 89

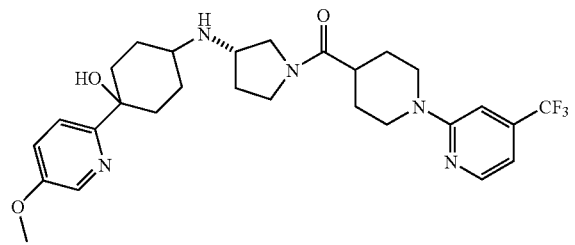

108

1-(5-Methoxypyridin-2-yl)-4-{[(3S)-1-({1-[4-(trifluoromethyl)pyridin-2-yl]piperidin-4-yl}carbonyl)pyrrolidin-3-yl]amino}cyclohexanol

MS (M+H) 548.2.

Example 90

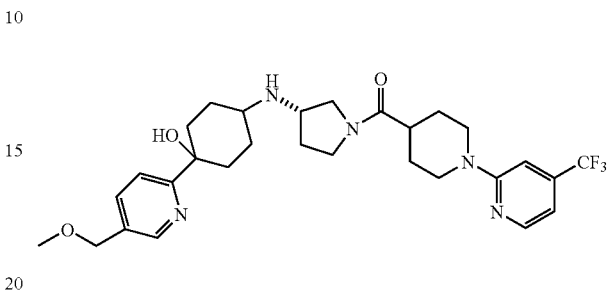

1-[5-(Methoxymethyl)pyridin-2-yl]-4-{[(3S)-1-({1-[4-(trifluoromethyl)pyridin-2-yl]piperidin-4-yl}carbonyl)pyrrolidin-3-yl]amino}cyclohexanol

MS (M+H) 562.2.

Example 91

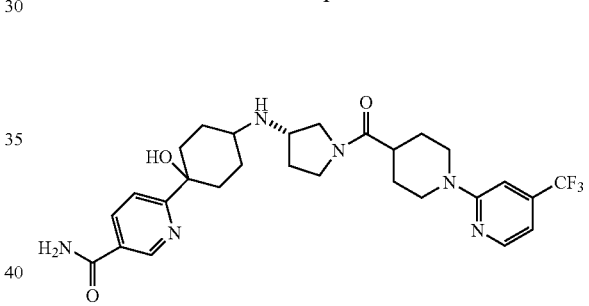

6-(1-Hydroxy-4-{[(3S)-1-({1-[4-(trifluoromethyl)pyridin-2-yl]piperidin-4-yl}carbonyl)pyrrolidin-3-yl]amino}cyclohexyl)nicotinamide

MS (M+H) 561.3.

Example 92

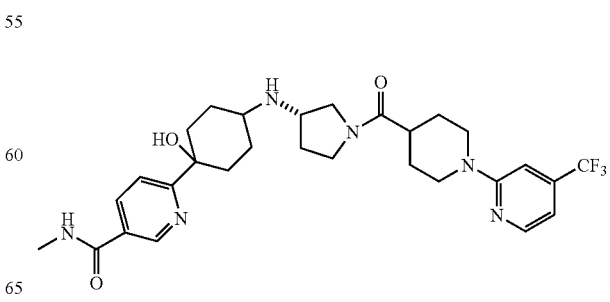

6-(1-Hydroxy-4-{[(3S)-1-({1-[4-(trifluoromethyl)pyridin-2-yl]piperidin-4-yl}carbonyl)pyrrolidin-3-yl]amino}cyclohexyl)-N-methylnicotinamide

MS (M+H) 575.3.

Example 93

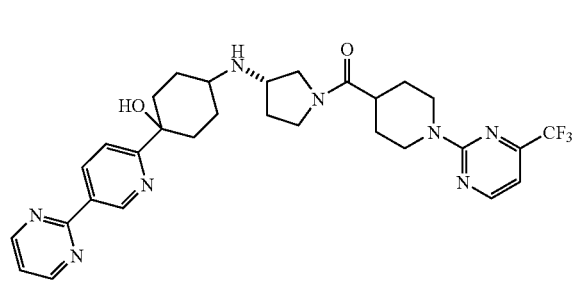

1-(5-Pyrimidin-2-ylpyridin-2-yl)-4-{[(3S)-1-({1-[4-(trifluoromethyl)pyrimidin-2-yl]piperidin-4-yl}carbonyl)pyrrolidin-3-yl]amino}cyclohexanol

MS (M+H) 597.4.

Example 94

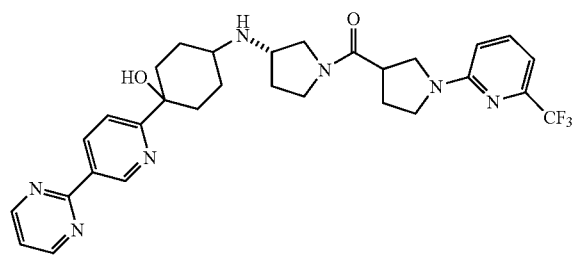

1-(5-Pyrimidin-2-ylpyridin-2-yl)-4-{[(3S)-1-({1-[6-(trifluoromethyl)pyridin-2-yl]pyrrolidin-3-yl}carbonyl)pyrrolidin-3-yl]amino}cyclohexanol

MS (M+H) 582.2.

Example 95

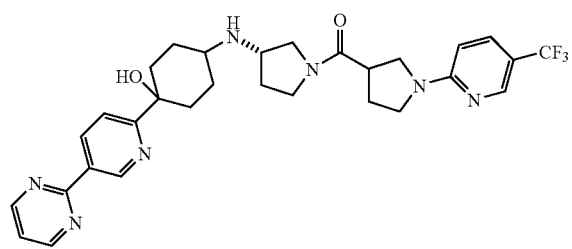

1-(5-Pyrimidin-2-ylpyridin-2-yl)-4-{[(3S)-1-({1-[5-(trifluoromethyl)pyridin-2-yl]pyrrolidin-3-yl}carbonyl)pyrrolidin-3-yl]amino}cyclohexanol

MS (M+H) 582.3.

Example 96

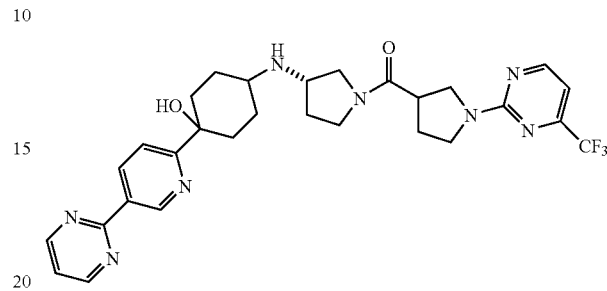

1-(5-Pyrimidin-2-ylpyridin-2-yl)-4-{[(3S)-1-({1-[4-(trifluoromethyl)pyrimidin-2-yl]pyrrolidin-3-yl}carbonyl)pyrrolidin-3-yl]amino}cyclohexanol

MS (M+H) 583.3.

Example 97

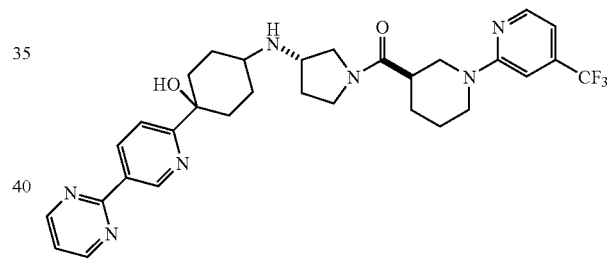

1-(5-Pyrimidin-2-ylpyridin-2-yl)-4-{[(3S)-1-({(3R)-1-[4-(trifluoromethyl)pyridin-2-yl]piperidin-3-yl}carbonyl)pyrrolidin-3-yl]amino}cyclohexanol

MS (M+H) 596.4.

Example 98

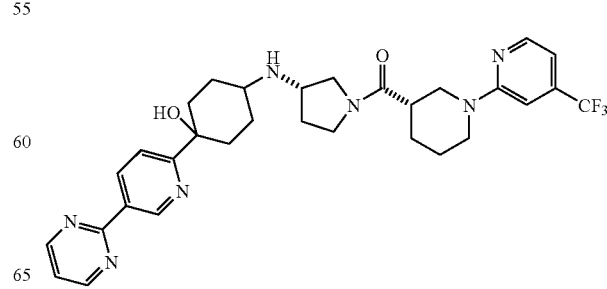

111

1-(5-Pyrimidin-2-ylpyridin-2-yl)-4-{[(3S)-1-({(3S)-1-[4-(trifluoromethyl)pyridin-2-yl]piperidin-3-yl}carbonyl)pyrrolidin-3-yl]amino}cyclohexanol

MS (M+H) 596.4.

Example 99

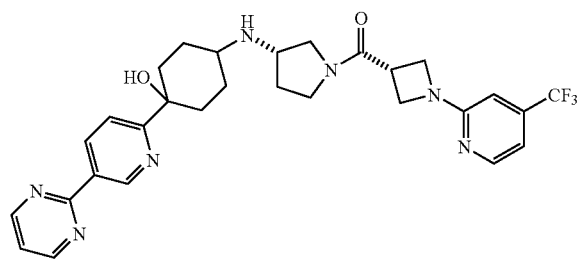

1-(5-Pyrimidin-2-ylpyridin-2-yl)-4-{[(3S)-1-({1-[4-(trifluoromethyl)pyridin-2-yl]azetidin-3-yl}carbonyl)pyrrolidin-3-yl]amino}cyclohexanol

MS (M+H) 568.1.

Example 100

Step A

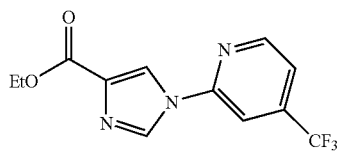

Ethyl 1-[4-(Trifluoromethyl)pyridin-2-yl]-1H-imidazole-4-carboxylate

To a solution of methyl 1H-imidazole-4-carboxylate (417 mg, 3.3 mmol) in DMF (10 mL) was added sodium hydride (130 mg, 3.3 mmol). After being stir for 1 h at room temperature, 2-chloro-4-(trifluoromethyl)pyridine (500 mg, 2.8 mmol) was added. The mixture was stirred at 80° C. overnight. After being cooled to room temperature, ethyl acetate was added. The solution was washed with brine several times, dried (MgSO₄) and concentrated. Chromatography on silica gel eluting with EtOAc/hexanes (1:1) afforded the title compound (120 mg). MS (M+H) 272.1.

Step B

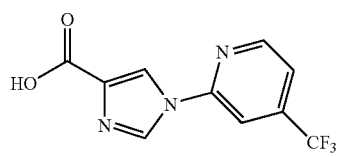 [SMILES: O=C(O)c1cn(-c2cc(C(F)(F)F)ccn2)cn1]

1-[4-(Trifluoromethyl)pyridin-2-yl]-1H-imidazole-4-carboxylic Acid

To a solution of methyl 1-[4-(trifluoromethyl)pyridin-2-yl]-1H-imidazole-4-carboxylate (120 mg, 0.44 mmol) in methanol (2.5 mL) was added a 5 M solution of sodium hydroxide in water (2.5 mL) and the mixture was stirred at room temperature for 1 h. After removal of methanol under vacuum, the resulting solution was acidified with concentrated HCl (pH=5) and concentrated. The residue was taken up in acetone and insolubles were filtered off. The filtrate was evaporated to give the title compound (120 mg). MS (M+H) 258.2.

Step C

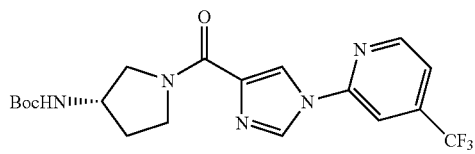 [SMILES: CC(C)(C)OC(=O)N[C@H]1CCN(C(=O)c2cn(-c3cc(C(F)(F)F)ccn3)cn2)C1]

tert-Butyl [(3S)-1-({1-[4-(Trifluoromethyl)pyridin-2-yl]-1H-imidazol-4-yl}carbonyl)pyrrolidin-3-yl]carbamate To a solution of 1-[4-(trifluoromethyl)pyridin-2-yl]-1H-imidazole-4-carboxylic acid (120 mg, 0.47 mmol) and tert-butyl (3S)-pyrrolidin-3-ylcarbamate (87 mg, 0.47 mmol) in DMF (3 mL) was added benzotriazol-1-yloxytris(dimethylamino)phosphonium hexafluorophosphate (210 mg, 0.47 mmol) followed by triethylamine (0.20 mL, 1.4 mmol). The reaction was stirred at room temperature overnight and purified by HPLC to give the title compound. MS (M+H) 426.3.

Step D

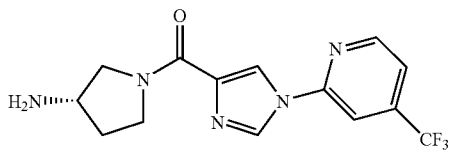 [SMILES: N[C@H]1CCN(C(=O)c2cn(-c3cc(C(F)(F)F)ccn3)cn2)C1]

1-({(3S)-1-[4-(Trifluoromethyl)pyridin-2-yl]-1H-imidazol-4-yl}carbonyl)pyrrolidin-3-amine To a solution of tert-butyl [(3S)-1-({1-[4-(trifluoromethyl)pyridin-2-yl]-1H-imidazol-4-yl}carbonyl)pyrrolidin-3-yl]carbamate (120 mg, 0.28 mmol) in methanol (2 mL) was added a 4.0 M solution of HCl in 1,4-dioxane (3.0 mL). After being stirred for 0.5 h, the solution was concentrated under vacuum to give the title compound. MS (M+H) 326.2.

Step E

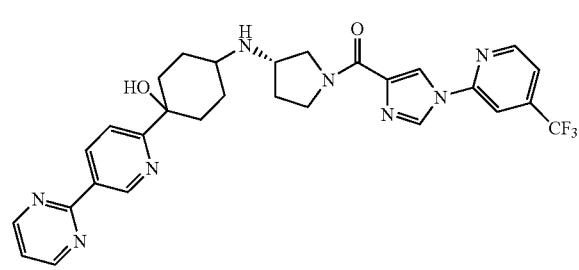 [SMILES: O=C(c1cn(-c2cc(C(F)(F)F)ccn2)cn1)N1CC[C@H](NC2CCC(O)(c3ccc(-c4ncccn4)cn3)CC2)C1]

1-(6-Pyrimidin-2-ylpyridin-3-yl)-4-{[(3S)-1-({1-[4-(trifluoromethyl)pyridin-2-yl]-1H-imidazol-4-yl}carbonyl)pyrrolidin-3-yl]amino}cyclohexanol To a solution of (3S)-1-({1-[4-(trifluoromethyl)pyridin-2-yl]-1H-imidazol-4-yl}carbonyl)pyrrolidin-3-amine (50 mg, 0.15 mmol) and 4-hydroxy-4-(6-pyrimidin-2-ylpyridin-3-yl)cyclohexanone (41 mg, 0.15 mmol) in methylene chloride (3 mL) was added sodium triacetoxyborohydride (36 mg, 0.17 mmol) followed by triethylamine (0.086 mL, 0.61 mmol). After being stirred at room temperature for 2 h, EtOAc (50 mL) was added. The solution was washed with NaHCO₃ solution and water, dried (MgSO₄) and concentrated. Purification by HPLC provided two isomers. MS (M+H) 579.3 for both isomers.

Example 101

Step A

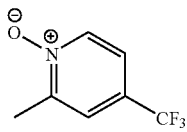

2-Methyl-4-(trifluoromethyl)pyridine 1-Oxide

To a solution of 2-methyl-4-(trifluoromethyl)pyridine (3.9 g, 24 mmol) in methylene chloride (50 mL) was added m-chloroperbenzoic acid (7.0 g, 31 mmol). After being stirred at room temperature overnight, the solution was washed with 50 mL of 1 N NaOH. The water phase was back-extracted with methylene chloride. The combined organic phases were dried over Na₂SO₄ and concentrated under vacuum to give the title compound. MS (M+H) 178.1.

Step B

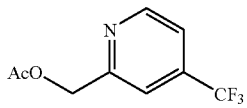

[4-(Trifluoromethyl)pyridin-2-yl]methyl Acetate

2-Methyl-4-(trifluoromethyl)pyridine 1-oxide (4.0 g, 22 mmol) was added to acetic anhydride (12 mL) at 120° C. The mixture was refluxed for 1 h. To it was carefully added 10 mL of ethanol. Reflux was continued for 10 min. The mixture was poured into ice, neutralized with NaHCO₃, and extracted with Et₂O. The organic layer was dried (MgSO₄) and concentrated. Chromatography on silica gel (5:2 hexanes/EtOAc) provided the product (3.4 g) as a brown oil. MS (M+H) 220.1.

Step C

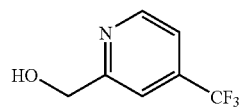 [SMILES: OCc1cc(C(F)(F)F)ccn1]

[4-(Trifluoromethyl)pyridin-2-yl]methanol

To a solution of [4-(trifluoromethyl)pyridin-2-yl]methyl acetate (1.0 g, 3.2 mmol) in methanol (10 mL) was added a 1.0 M solution of sodium hydroxide in water (10 mL). After being stirred at room temperature overnight, the solution was diluted with 20 mL of water and extracted with EtOAc twice. The combined organic layers were dried (MgSO₄) and concentrated under vacuum. Chromatography on silica gel eluting with hexanes/EtOAc (1:1) afforded the title compound (0.34 g) as a clear oil. MS (M+H) 178.1.

Step D

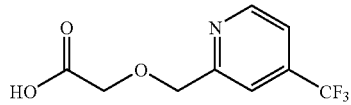 [SMILES: O=C(O)COCc1cc(C(F)(F)F)ccn1]

{[4-(Trifluoromethyl)pyridin-2-yl]methoxy}acetic Acid

To a solution of [4-(trifluoromethyl)pyridin-2-yl]methanol (340 mg, 1.9 mmol) in DMF (10 mL) was added sodium hydride (150 mg, 3.8 mmol). After being stirred at room temperature for 5 min. 1,1-dimethylethyl bromoacetate (0.28 mL, 1.9 mmol) was added. Stirring was continued at room temperature for 1 h. Water (20 mL) was added and the resulting solution was extracted with EtOAc. The water layer was neutralized to pH=5 with HCl and extracted with EtOAc twice. The combined organic layers were dried (MgSO₄) and concentrated under vacuum to give the title compound which was used for the next reaction without purification. MS (M+H) 292.2.

Step E

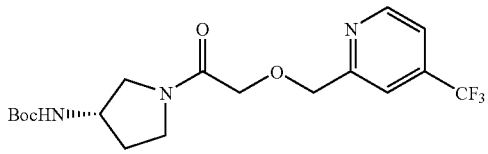 [SMILES: CC(C)(C)OC(=O)N[C@H]1CCN(C(=O)COCc2cc(C(F)(F)F)ccn2)C1]

tert-Butyl [(3S)-1-({[4-(Trifluoromethyl)pyridin-2-yl]methoxy}acetyl)pyrrolidin-3-yl]carbamate To a solution of {[4-(trifluoromethyl)pyridin-2-yl]methoxy}acetic acid (450 mg, 1.9 mmol) and tert-butyl (3S)-pyrrolidin-3-ylcarbamate (360 mg, 1.9 mmol) in DMF (10 mL) was added benzotriazol-1-yloxytris(dimethylamino)phosphonium hexafluorophosphate (880 mg, 2.0 mmol) followed by triethylamine (0.80 mL, 5.7 mmol). After being stirred at room temperature overnight, ethyl acetate was added. The solution was washed with 1 N NaOH and water. Purification on silica gel column eluting with EtOAc provided the title compound (300 mg) as a clear oil. MS (M+H) 404.3.

Step F

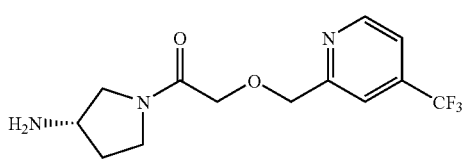 [SMILES: N[C@H]1CCN(C(=O)COCc2cc(C(F)(F)F)ccn2)C1]

1-({[4-(Trifluoromethyl)pyridin-2-yl]methoxy}acetyl)pyrrolidin-3-amine

To a solution of tert-butyl [(3S)-1-({[4-(trifluoromethyl)pyridin-2-yl]methoxy}acetyl)pyrrolidin-3-yl]carbamate (300 mg, 0.74 mmol) in methanol (3 mL) was added a 4.0 M solution of HCl in 1,4-dioxane (6 mL). After being stirred for 0.5 h at room temperature, the solution was concentrated under vacuum to give the title compound. MS (M+H) 304.2.

Step G

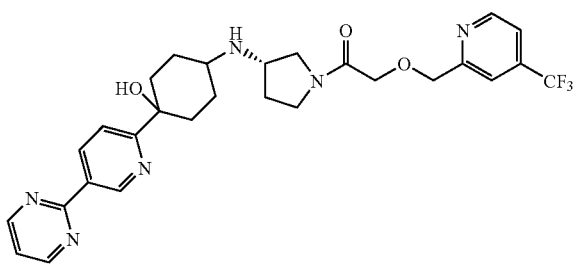 [SMILES: O=C(COCc1cc(C(F)(F)F)ccn1)N1CC[C@H](NC2CCC(O)(c3ccc(-c4ncccn4)cn3)CC2)C1]

1-(5-Pyrimidin-2-ylpyridin-2-yl)-4-{[(3S)-1-({[4-(trifluoromethyl)pyridin-2-yl]methoxy}acetyl)pyrrolidin-3-yl]amino}cyclohexanol To a solution of (3S)-1-({[4-(trifluoromethyl)pyridin-2-yl]methoxy}acetyl)pyrrolidin-3-amine (47 mg, 0.15 mmol) and 4-hydroxy-4-(5-pyrimidin-2-ylpyridin-2-yl)cyclohexanone (41 mg, 0.15 mmol) in methanol (2 mL) and isopropanol (2 mL) was added sodium triacetoxyborohydride (36 mg, 0.17 mmol). After being stirred at room temperature overnight, EtOAc was added. The solution was washed with NaHCO₃ solution and water, dried (MgSO₄) and concentrated. Purification by HPLC provided two isomers of the title compound. MS (M+H) 557.2 for both isomers.

Example 102

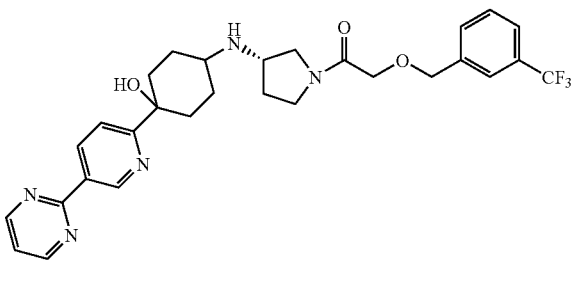 [SMILES: O=C(COCc1cccc(C(F)(F)F)c1)N1CC[C@H](NC2CCC(O)(c3ccc(-c4ncccn4)cn3)CC2)C1]

1-(5-Pyrimidin-2-ylpyridin-2-yl)-4-{[(3S)-1-({[4-(trifluoromethyl)2-phenyl]methoxy}acetyl)pyrrolidin-3-yl]amino}cyclohexanol The title compound was prepared in a manner analogous to that for Example 101. MS (M+H) 556.3.

Pharmaceutical Applications of the Compounds of the Invention

The capacity of the novel compounds of the invention to antagonize CCR2 function can be determined using a suitable screen (e.g., high through-put assay). For example, an agent can be tested in an extracellular acidification assay, calcium flux assay, ligand binding assay or chemotaxis assay (see, for example, Hesselgesser et al., J. Biol. Chem. 273(25):15687-15692 (1998); WO 00/05265 and WO 98/02151).

In a practical assay, a CCR2 protein which can be isolated or recombinantly derived is used which has at least one property, activity or functional characteristic of a mammalian CCR2 protein. The specific property can be a binding property (to, for example, a ligand or inhibitor), a signalling activity (e.g., activation of a mammalian G protein, induction of rapid and transient increase in the concentration of cytosolic free calcium [Ca⁺⁺]i, cellular response function (e.g., stimulation of chemotaxis or inflammatory mediator release by leukocytes), and the like.

In one embodiment, a composition containing a CCR2 protein or variant thereof is maintained under conditions suitable for binding. The CCR2 receptor is contacted with a compound to be tested, and binding is detected or measured.

In alternate embodiments, the assay is a cell-based assay and cells are used which are stably or transiently transfected with a vector or expression cassette having a nucleic acid sequence which encodes the CCR2 receptor. The cells are maintained under conditions appropriate for expression of the receptor and are contacted with an agent under conditions appropriate for binding to occur. Binding can be detected using standard techniques. For example, the extent of binding can be determined relative to a suitable control. Also, a cellular fraction, such as a membrane fraction, containing the receptor can be used in lieu of whole cells.

Detection of binding or complex formation can be detected directly or indirectly. For example, the agent can be labeled with a suitable label (e.g., fluorescent label, label, isotope label, enzyme label, and the like) and binding can be determined by detection of the label. Specific and/or competitive binding can be assessed by competition or displacement studies, using unlabeled agent or a ligand as a competitor.

The CCR2 antagonist activity of test agents (e.g., the 3-cycloakylaminopyrrolidine compounds of formula I or II of the invention) can be reported as the inhibitor concentration required for 50% inhibition ($IC_{50}$ values) of specific binding in receptor binding assays using $^{125}$I-labeled MCP-1, as ligand, and Peripheral Blood Mononuclear Cells (PBMCs) prepared from normal human whole blood via density gradient centrifugation. Specific binding is preferably defined as the total binding (e.g., total cpm on filters) minus the non-specific binding. Non-specific binding is defined as the amount of cpm still detected in the presence of excess unlabeled competitor (e.g., MCP-1).

The human PBMCs described above can be used in a suitable binding assay. For example, 200,000 to 500,000 cells can be incubated with 0.1 to 0.2 nM $^{125}$I-labeled MCP-1, with or without unlabeled competitor (10 nM MCP-1) or various concentrations of compounds to be tested. $^{125}$I-labeled MCP-1, can be prepared by suitable methods or purchased from commercial vendors (Perkin Elmer, Boston Mass.), The binding reactions can be performed in 50 to 250 µl of a binding buffer consisting of 1M HEPES pH 7.2, and 0.1% BSA (bovine serum albumin), for 30 min at room temperature. The binding reactions can be terminated by harvesting the membranes by rapid filtration through glass fiber filters (Perkin Elmer) which can be presoaked in 0.3% polyethyleneimine or Phosphate Buffered Saline (PBS). The filters can be rinsed with approximately 600 µl of binding buffer containing 0.5 M NaCl or PBS, then dried, and the amount of bound radioactivity can be determined by counting on a Gamma Counter (Perkin Elmer).

The capacity of compounds to antagonize CCR2 function can also be determined in a leukocyte chemotaxis assay using suitable cells. Suitable cells include, for example, cell lines, recombinant cells or isolated cells which express CCR2 and undergo CCR2 ligand-induced (e.g., MCP-1) chemotaxis. The assay in use, utilizes human peripheral blood mononuclear cells, in a modified Boyden Chamber (Neuro Probe). 500,000 cells in serum free DMEM media (In Vitrogen) are incubated with or without the inhibitors and warmed to 37° C. The chemotaxis chamber (Neuro Probe) is also prewarmed. 400 ul of warmed 10 nM MCP-1 is added to the bottom chamber in all wells expect the negative control which has DMEM added. An 8 micron membrane filter (Neuro Probe) is place on top and the chamber lid is closed. Cells are then added to the holes in the chamber lid which are associated with the chamber wells below the filter membrane. The whole chamber is incubated at 37° C., 5% CO2 for 30 minutes. The cells are then aspirated off, the chamber lid opened, and the filter gently removed. The top of the filter is washed 3 times with PBS and the bottom is left untouched. The filter is air dried and stained with Wright Geimsa stain (Sigma). Filters are counted by microscopy. The negative control wells serve as background and are subtracted from all values. Antagonist potency can be determined by comparing the number of cell that migrate to the bottom chamber in wells which contain antagonist, to the number of cells which migrate to the bottom chamber in MCP-1 control wells.

When the binding assay protocol is used, the compounds of the present invention have IC50 in the range of about 0.01 to about 500 (nM). In chemotaxis assays the compounds of the invention have IC50's in the range of about 1 to about 3000 (nM).

A method of modulating activity of a chemokine receptor comprising contacting said chemokine receptor with a compound of claim. Chemokine receptors to which the present compounds bind and/or modulate include any chemokine receptor. In some embodiments, the chemokine receptor belongs to the CC family of chemokine receptors including, for example, CCR1, CCR2, CCR3, CCR4, CCR5, CCR6, CCR7, and CCR8. In some embodiments, the chemokine receptor is CCR2. In some embodiments, the chemokine receptor is CCR5. In some embodiments, the chemokine receptor binds and/or modulates both CCR2 and CCR5.

As used herein, the term "contacting" refers to the bringing together of indicated moieties in an in vitro system or an in vivo system. For example, "contacting" the chemokine receptor with a compound of the invention includes the administration of a compound of the present invention to an individual or patient, such as a human, having a chemokine receptor, as well as, for example, introducing a compound of the invention into a sample containing a cellular or purified preparation containing the chemokine receptor.

The compounds of the invention can be selective. By "selective" is meant that a compound binds to or inhibits a chemokine receptor with greater affinity or potency, respectively, compared to at least one other chemokine receptor, or preferably compared to all other chemokine receptors of the same class (e.g., all other CC-type receptors). In some embodiments, the compounds of the invention have binding or inhibition selectivity for CCR2 or CCR5 over any other chemokine receptor. Selectivity can be at least about 10-fold, at least about 20-fold, at least about 50-fold, at least about 100-fold, at least about 200-fold, at least about 500-fold or at least about 1000-fold. Binding affinity and inhibitor potency can be measured according to routine methods in the art, such as according to the assays provided herein.

The present invention further provides methods of treating a chemokine receptor-associated disease or disorder in an individual (e.g., patient) by administering to the individual in need of such treatment a therapeutically effective amount or dose of a compound of the present invention or a pharmaceutical composition thereof. A chemokine receptor-associated disease can include any disease, disorder or condition that is directly or indirectly linked to expression or activity of the chemokine receptor. A chemokine receptor-associated disease can also include any disease, disorder or condition that can be prevented, ameliorated, or cured by modulating chemokine receptor activity. A chemokine receptor-associated disease can further include any disease, disorder or condition that is characterized by binding of an infectious agent such as a virus or viral protein with a chemokine receptor. In some embodiments, the chemokine receptor-associated disease is a CCR5-associated disease such as HIV infection.

As used herein, the term "individual" or "patient," used interchangeably, refers to any animal, including mammals, preferably mice, rats, other rodents, rabbits, dogs, cats, swine, cattle, sheep, horses, or primates, and most preferably humans. The compounds of the invention can be administered to a mammal, such as a human, but can also be other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is a mammal, male or female, in whom modulation of chemokine receptor activity is desired. The term modulation is intended to encompass antagonism (e.g., inhibition), agonism, partial antagonism and/or partial agonism. In some embodiments, compounds of the present invention are antagonists (e.g., inhibitors) of chemokine receptors.

In the present specification, the term "therapeutically effective amount" means the amount of the subject compound that will elicit the biological or medical response of a tissue, system, animal or human that is being sought by the researcher, veterinarian, medical doctor or other clinician.

The compounds of the invention are administered in therapeutically effective amounts to treat a disease for example such as rheumatoid arthritis. A therapeutically effective amount of a compound is that amount which results in the inhibition of one or more of the processes mediated by the binding of a chemokine to a receptor such as CCR2 in a subject with a disease associated with aberrant leukocyte recruitment and/or activation. Typical examples of such processes include leukocyte migration, integrin activation, transient increases in the concentration of intracellular free calcium $[Ca^{2+}]i$ and granule release of proinflammatory mediators. Alternatively, a therapeutically effective amount of a compound is the quantity required to achieve a desired therapeutic and/or prophylactic effect, such as an amount which results in the prevention of or a decrease in the symptoms associated with a disease associated with aberrant leukocyte recruitment and/or activation.

Additional diseases or conditions of human or other species which can be treated with the inhibitors or modulators of chemokine receptor function of the invention, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease, graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, restenosis, certain hematologic malignancies, cytokine-induced toxicity (e.g., septic shock, endotoxic shock), polymyositis, dermatomyositis.

In some embodiments, the chemokine receptor-associated diseases, disorders and conditions include inflammation and inflammatory diseases, immune disorders, cancer, and viral infections. Example inflammatory diseases include diseases having an inflammatory component such as asthma, allergic rhinitis, restenosis, atherosclerosis, multiple sclerosis, Crohn's disease, ulcerative colitis, hypersensitivity lung diseases, neuropathic pain, hypersensitivity pneumonitis, eosinophilic pneumonias, delayed-type hypersensitivity, asthma, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis), eye disorders (e.g., retinal neurodegeneration, choroidal neovascularization, etc.), obesity, and the like. Example immune disorders include rheumatoid arthritis, psoriatic arthritis, systemic lupus erythematosus, myastenia gravis, diabetes (e.g., juvenile onset diabetes), insulin resistance; glomerulonephritis, autoimmune throiditis, organ transplant rejection including allograft rejection and graft-versus-host disease. Example cancers include cancers such as breast cancer, ovarian cancer, multiple myeloma and the like that are characterized by infiltration of macrophages (e.g., tumor associated macrophages, TAMs) into tumors or diseased tissues. Example viral infections include HIV infection.

One or more additional pharmaceutical agents such as, for example, antibodies, anti-inflammatory agents, immunosuppressants, chemotherapeutics can be used in combination with the compounds of the present invention for treatment of chemokine receptor-associated diseases, disorders or conditions. The agents can be combined with the present compounds in a single dosage form, or the agents can be administered simultaneously or sequentially as separate dosage forms.

One or more additional pharmaceutical agents such as, for example, anti-viral agents, antibodies, anti-inflammatory agents, and/or immunosuppressants can be used in combination with the compounds of the present invention for treatment of chemokine receptor-associated diseases, disorders or conditions. The agents can be combined with the present compounds in a single dosage form, or the agents can be administered simultaneously or sequentially as separate dosage forms.

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis (POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6,-diamino-purine dioxolane); and lodenosine (FddA).

Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4(1H,3H)-pyrimidinedione); and (+)-calanolide A (NSC-675451) and B.

Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1549.

Other antiviral agents include hydroxyurea, ribavirin, IL-2, IL-12, pentafuside and Yissum Project No. 11607.

In some embodiments, anti-inflammatory or analgesic agents contemplated for use in combination with the compounds of the present invention can comprise, for example, an opiate agonist, a lipoxygenase inhibitor such as an inhibitor of 5-lipoxygenase, a cyclooxygenase inhibitor such as a cyclooxygenase-2 inhibitor, an interleukin inhibitor such as an interleukin-I inhibitor, an NNMA antagonist, an inhibitor of nitric oxide or an inhibitor of the synthesis of nitric oxide, a non-steroidal antiinflammatory agent, or a cytokine-suppressing antiinflammatory agent, for example, such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds can be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedfine, or levo-desoxyephedrine; an antitussive such as codeine, hydrocodone, caramiphen, carbetapentane, or dextramethorphan; a diuretic; and a sedating or non-sedating antihistamine.

In some embodiments, pharmaceutical agents contemplated for use in combination with the compounds of the present invention can comprise (a) VLA-4 antagonists such as those described in U.S. Pat. No. 5,510,332, WO95/15973, WO96/01644, WO96/06108, WO96/20216, WO96/229661, WO96/31206, WO96/4078, WO97/030941, WO97/022897 WO 98/426567 WO98/53814, WO98/53817, WO98/538185, WO98/54207, and WO98/58902; (b) steroids such as beclornethasone, methylpi-ednisolone, betarnethasone, prednisone, dexamethasone, and hydrocortisone; (c) immunosuppressants such as cyclosporin, tacrolimus, raparnycin and other FK506 type immunosuppressants; (d) antihistamines (HI-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, asternizole, terfenadine, loratadine, cetirizine, fexofenadine, desearboethoxyloratadine, and the like; (e) non-steroidal anti-asthmatics such as terbutaline, metaproterenol, fenoterol, isoethaiine, albuterol, bitolterol, pirbuterol, theophylline, cromolyn sodium, atropine, ipratropium bromide, leukotriene antagonists (e.g., zafirlukast, montelukast, pranlukast, iralukast, pobilukast, SKB-106,203), leukotriene biosynthesis inhibitors (e.g., zileuton, BAY-1005); (f) nonsteroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (e.g., indomethacin, acernetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenarnic acid derivatives (flufenarnic acid, meclofenamic acid, mefenamic acid, niflumic acid and tolfenarnic acid), biphenylearboxylic acid derivatives (diflunisal and flufenisal), oxicarns (isoxicarn, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CXCR-4, CCRI, CCR2, CCR3 and CCR5 (j) cholesterol lowering agents such as HMG-CoA reductase inhibitors (lovastatin, sirrivastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), U.-glucosidase inhibitors (acarbose) and orlitazones (troglitazone and pioglitazone); (1) preparations of interferon beta (interferon beta-lo., interferon beta-1 P); (m) other compounds such as aminosalicylic acids, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient.

Rheumatoid arthritis (RA) patients, treated aggressively with disease modifying agents (methotrexate, antimalarials, gold, penicillamine, sulfasalazine, dapsone, leflunamide, or biologicals), can achieve varying degrees of disease control, including complete remissions. These clinical responses are associated with improvement in standardized scores of disease activity, specifically the ACR criteria which includes: pain, function, number of tender joints, number of swollen joints, patient global assessment, physician global assessment, laboratory measures of inflammation (CRP and ESR), and radiologic assessment of joint structural damage. Current disease-modifying drugs (DMARDs) require continued administration to maintain optimal benefit. Chronic dosing of these agents is associated with significant toxicity and host defense compromise. Additionally, patients often become refractory to a particular therapy and require an alternative regimen. For these reasons, a novel, effective therapy which allows withdrawal of standard DMARDs would be a clinically important advance.

Patients with significant response to anti-TNF therapies (infliximab, etanercept, adalimumab), anti-IL-1 therapy (kinaret) or other disease modifying anti-rheumatic drugs (DMARDs) including but not limited to methotrexate, cyclosporine, gold salts, antimalarials, penicillamine or leflunamide, who have achieved clinical remission of disease can be treated with a substance that inhibits expression and/or activity of CCR2 including, for example, nucleic acids (e.g., antisense or siRNA molecules), proteins (e.g., anti-CCR2 antibodies), small molecule inhibitors (e.g., the compounds disclosed herein and other chemokine receptor inhibitors known in the art).

In some embodiments, the substance that inhibits expression and/or activity of CCR2 is a small molecule CCR2 inhibitor (or antagonist). The CCR2 antagonist can be dosed orally q.d. or b.i.d at a dose not to exceed about 500 mgs a day. The patients can be withdrawn from or have a decrease in the dosage of their current therapy and would be maintained on treatment with the CCR2 antagonist. Treating patients with a combination of CCR2 antagonist and their current therapy can be carried out for, for example, about one to about two days, before discontinuing or dose reducing the DMARD and continuing on CCR2 antagonist.

Advantages of substituting traditional DMARDS with CCR2 antagonists are numerous. Traditional DMARDs have serious cumulative dose-limiting side effects, the most common being damage to the liver, as well as immunosuppressive actions. CCR2 antagonism is expected to have an improved long-term safety profile and will not have similar immunosuppressive liabilities associated with traditional DMARDs.

Additionally, the half-life of the biologicals is typically days or weeks, which is an issue when dealing with adverse reactions. The half-life of an orally bioavailable CCR2 antagonist is expected to be on the order of hours so the risk of continued exposure to the drug after an adverse event is very minimal as compared to biological agents. Also, the current biologic agents (infliximab, etanercept, adalimumab, kinaret) are typically given either i.v. or s.c., requiring doctor's administration or patient self-injection. This leads to the possibility of infusion reaction or injection site reactions. These are avoidable using an orally administered CCR2 antagonist.

The compounds of the invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the metabolic stability, rate of excretion, drug combination, and length of action of that compound the species, age, sex, health, medical condition, and weight of the recipient; the nature and extent of the symptoms; the kind of concurrent treatment; the frequency of treatment; the specific route of administration, the renal and hepatic function of the patient, and the desired effect. A physician or veterinarian can determine and prescribe the effective amount of the drug required to prevent, counter, or arrest the progress of the specific disorder for which treatment is necessary.

Generally, the daily oral dosage of each active ingredient, when used for the indicated effects, will range between about 0.0001 to 1000 mg/kg of body weight, preferably between about 0.001 to 100 mg/kg of body weight per day, and most preferably between about 0.1 to 20 mg/kg/day. For intravenous use, the most preferred doses will range from about 0.1 to about 10 mg/kg/minute during a constant rate infusion. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

The compounds of the instant invention can also be administered in intranasal form via topical use of suitable intranasal vehicles, or via transdermal routes, e.g., by using transdermal skin patches. When administered in the form of a transdermal delivery system, the dosage administration can be continuous rather than intermittent throughout the dosage regimen.

The compounds of the invention are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. For oral administration in liquid form, the oral drug components can be combined with any oral, non-toxic, pharmaceutically acceptable inert carrier such as ethanol, glycerol, water, and the like. Additionally, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be provided to a patient in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or poly-ethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, and crosslinked or amphipathic block copolymers of hydrogels.

Dosage forms for the compounds of the invention suitable for administration may contain from about 0.1 milligram to about 100 milligrams of active ingredient per dosage unit. In these pharmaceutical compositions the active ingredient will ordinarily be present in an amount of about 0.5-95% by weight based on the total weight of the composition.

Gelatin capsules can also be used as dosage forms and may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

When using liquid dosage forms for oral administration they can contain coloring and flavoring to increase patient acceptance.

Generally, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in the field of pharmacology.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. As used herein, topical application is also meant to include the use of mouth washes and gargles.

The pharmaceutical compositions and methods of the present invention may further comprise other therapeutically active compounds which are usually applied in the treatment of the above mentioned pathological conditions.

Representative useful pharmaceutical dosage-forms for administration of the compounds of this invention can be illustrated as follows:

Capsules

A large number of unit capsules can be prepared by filling standard two-piece hard gelatin capsules each with 50 milligrams of powdered active ingredient, 100 milligrams of lactose, 25 milligrams of cellulose, and 3 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 75 milligrams of the active ingredient. The capsules should be washed and dried.

Tablets

Tablets may be prepared by conventional procedures so that the dosage unit is 75 milligrams of active ingredient, 0.15 milligrams of colloidal silicon dioxide, 4 milligrams of magnesium stearate, 250 milligrams of microcrystalline cellulose, 9 milligrams of starch and 75 milligrams of lactose. Appropriate coatings well known to one skilled in the art may be applied to increase palatability or delay absorption.

Injectable

A parenteral composition suitable for administration by injection may be prepared by stirring 1.0% by weight of active ingredient in 8% by volume propylene glycol and water. The solution should be made isotonic with sodium chloride and sterilized.

Suspension

An aqueous suspension can be prepared for oral administration so that each 5 mL contain 75 mg of finely divided active ingredient, 150 mg of sodium carboxymethyl cellulose, 3.75 mg of sodium benzoate, 0.75 g of sorbitol solution, U.S.P., and 0.015 mL of vanillin.

Example A

This example describes a procedure to evaluate the efficacy of CCR2 antagonists for treatment of rheumatoid arthritis.

An animal model of rheumatoid arthritis can be induced in rodents by injecting them with type II collagen in selected adjuvants. Three series of rodent groups consisting 15 genetically-susceptible mice or rats per group are injected subcutaneously or intra-dermally with type II collagen emulsified in Complete Freund's Adjuvant at days 0 and 21. One series of rodents additionally receives phosphate buffered saline (PBS) and Tween 0.5% i.p. at the initial sensitization, and at different dosing schedules thereafter. A second series consists of groups of rodents receiving different doses of the CCR2 antagonist(s) given either intra-peritoneally, intravenously, subcutaneously, intra-muscularly, orally, or via any other mode of administration at the initial sensitization, and at different dosing schedules thereafter. A third series of rodents, serving as positive control, consists of groups treated with either mouse IL-10 i.p., or anti-TNF antibodies i.p. at the initial sensitization, and at different dosing schedules thereafter.

Animals are monitored from weeks 3 til 8 for the development of swollen joints or paws, and graded on a standard disease severity scale. Disease severity is confirmed by histological analysis of joints.

Another aspect of the present invention relates to radio-labeled compounds of the invention that would be useful not only in radio-imaging but also in assays, both in vitro and in vivo, for localizing and quantitating the chemokine receptor in tissue samples, including human, and for identifying chemokine receptor ligands by inhibition binding of a radio-labeled compound. Accordingly, the present invention includes chemokine receptor assays that contain such radio-labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro chemokine receptor labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$.

Synthetic methods for incorporating radio-isotopes into organic compounds are applicable to compounds of the invention and are well known in the art.

A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the chemokine receptor. Accordingly, the ability of a test compound to compete with the radio-labeled compound for binding to the chemokine receptor directly correlates to its binding affinity.

The present invention also includes pharmaceutical kits useful, for example, in the treatment or prevention of chemokine-associated diseases which include one or more containers containing a pharmaceutical composition comprising a therapeutically effective amount of a compound of Formula I. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

All publications, patents, and patent applications including all cited art and bibliographic references cited herein are hereby incorporated by reference in their entirety for all purposes.

While the many forms of the invention herein disclosed constitute presently preferred embodiments, many others are possible and further details of the preferred embodiments and other possible embodiments are not to be construed as limitations. It is understood that the terms used herein are merely descriptive rather than limiting and that various changes many equivalents may be made without departing from the spirit or scope of the claimed invention.

What is claimed is:

1. A compound of the formula I:

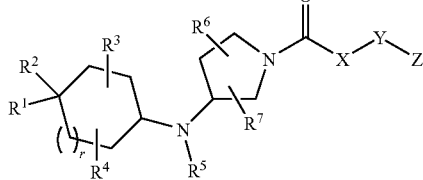

or pharmaceutically acceptable salt thereof, wherein:

X and Y together are selected from the group consisting of:
a) —$CH_2$—NH—(C=O)—;
b) —$CH_2$—O—$CH_2$—;

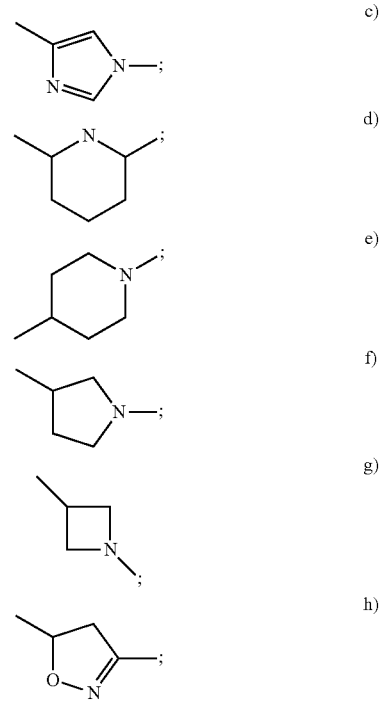

Z is a phenyl, pyridyl or pyrimidinyl group that is substituted with a $CF_3$ group;

$R^1$ is phenyl, pyridyl, thiazole, pyrimidine or pyrazine, wherein said $R^1$ is substituted with 0-3 $R^{1a}$, wherein $R^{1a}$ is independently selected from the group consisting of: $CH_2$—OMe, alkyl amides, pyrollidinyl amides, morpholinyl, alkyl, alkoxy, $CH_2$—$NMe_2$, pyridyl, carboxylate, phenyl bearing a $CH_2$—OH group, pyrimidine, thiazole, oxazole and pyrazine;

$R^2$ is OH;

$R^3$ and $R^4$ are H;

$R^5$ is independently selected from the group consisting of hydrogen, alkyl, and formyl;

$R^6$ and $R^7$ are each independently selected from the group consisting of H, $C_1$-$C_{10}$ alkyl, OH, $CH_2$—OMe and hydroxyalkyl; and r=1.

2. A composition comprising a compound of claim 1 and a pharmaceutically acceptable carrier.

* * * * *